US011833187B2

(12) United States Patent
Ito et al.

(10) Patent No.: US 11,833,187 B2
(45) Date of Patent: Dec. 5, 2023

(54) MATERIALS AND METHODS FOR EXTRACELLULAR VESSICLE-ASSOCIATED DISEASES

(71) Applicant: THE BRIGHAM AND WOMEN'S HOSPITAL, INC., Boston, MA (US)

(72) Inventors: Shinsuke Ito, Tokyo (JP); Elena Aikawa, Chestnut Hill, MA (US); Masanori Aikawa, Chestnut Hill, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 375 days.

(21) Appl. No.: 16/753,359

(22) PCT Filed: Oct. 23, 2018

(86) PCT No.: PCT/US2018/057016
§ 371 (c)(1),
(2) Date: Apr. 3, 2020

(87) PCT Pub. No.: WO2019/083944
PCT Pub. Date: May 2, 2019

(65) Prior Publication Data

US 2020/0330553 A1 Oct. 22, 2020

Related U.S. Application Data

(60) Provisional application No. 62/575,762, filed on Oct. 23, 2017.

(51) Int. Cl.
*A61K 38/17* (2006.01)
*A61K 47/65* (2017.01)
*G01N 33/68* (2006.01)

(52) U.S. Cl.
CPC .......... *A61K 38/1741* (2013.01); *A61K 47/65* (2017.08); *G01N 33/6803* (2013.01)

(58) Field of Classification Search
None
See application file for complete search history.

(56) References Cited

U.S. PATENT DOCUMENTS

| | | | |
|---|---|---|---|
| 2010/0028333 | A1 | 2/2010 | William et al. |
| 2011/0166032 | A1 | 7/2011 | Munck Petersen et al. |
| 2016/0060346 | A1 | 3/2016 | Lundbeck |
| 2017/0014476 | A1 | 1/2017 | Pedersen et al. |

FOREIGN PATENT DOCUMENTS

| | | | |
|---|---|---|---|
| JP | 2011518791 | B2 | 4/2009 |
| WO | 2009/132656 | A2 | 11/2009 |
| WO | 2016/164637 | A1 | 10/2016 |
| WO | 2016164608 | A1 | 10/2016 |

OTHER PUBLICATIONS

Leloup et al. ("Low pH-induced conformation change and dimerization of sortilin triggers endocytosed ligand release" Nature communications 8:1708, Nov. 2017).*
McCormick et al., "Palmitoylation controls recycling in lysosomal sorting and trafficking" Traffiic 9(11) 1984-1987 (2008).
Hermey, "The Vps10p-domain receptor family." Cellular and molecular life sciences 66.16 (2009).
Westergaard et al. "Functional organization of the sortilin Vps10p domain." Journal of Biological Chemistry 279.48 (2004).

* cited by examiner

*Primary Examiner* — Julie Ha
*Assistant Examiner* — Tara L Martinez
(74) *Attorney, Agent, or Firm* — Nixon Peabody LLP; David S. Resnick; Ravinderjit Braich

(57) ABSTRACT

Sortilin is a sorting receptor that directs target proteins to the secretary or endocytic compartments of cells that is found in both extracellular vesicles and cells. Provided herein are methods and compositions for decreasing or inhibiting trafficking of sortilin to an extracellular vesicle, for example by inhibiting the formation of intermolecular sortilin dimers.

9 Claims, 14 Drawing Sheets

Specification includes a Sequence Listing.

FLAG-sortilin
6XHis-sortilin
1
78 80
81
831
SP
PP
FLAG
6XHis
Extracellular domain
TMD
ICD kDa
150
100
50
37
IB: sortilin
IB: 6XHis
IB: FLAG
IB: β-actin
FLAG-sortilin
6X His-sortilin TR-FRET
**
%
200
150
100
50
0
-50
-100
FLAG-sortilin HTRF
*
%
150
100
50
0
-50
FLAG-sortilin FLAG-sortilin Full
FLAG-sortilin ECD+TMD
FLAG-sortilin ICD+TMD
SP
PP
FLAG
Extracellular domain
TMD
ICD
1
78 80
81
755
778
831

Reducing
Control
Full
ECD +TMD
ICD +TMD
kDa
250
150
100
75
50
37
25
20
15
IB: FLAG
IB: β-actin Non-reducing
MU
D
MO BS3:
Control
Full
ECD +TMD
- + - + - +
IB: FLAG
IB: β-actin FLAG-sortilin WT
FLAG-sortilin CD43-TMD
1
78 80
81
754
779
831
SP
PP
FLAG
Extracellular domain
TMD
ICD
CD43-TMD (254-276)

FLAG-sortilin
Control
WT
CD43-TMD
kDa
250
150
100
75
50
37
MU
D
MO
IB: FLAG
IB: β-actin Whole cell lysate
6XHis-sortilin
Control
WT
CD43-TMD
sortilin
IB: 6XHis
IB: FLAG Immunoprecipitation
6XHis-sortilin
Control
WT
CD43-TMD
IP: IgG FLAG IgG FLAG IgG FLAG
IB: 6XHis
IB: FLAG FLAG-sortilin WT
FLAG-sortilin S316E
FLAG-sortilin wp
1
SP
PP
78 80
FLAG
81
316
S
E
Extracellular domain
TMD
ICD
831
1 33 78 80 kDa
250
150
100
75
50
37
Vec WT S316E
Vec WT wp
FLAG-sortilin
MU
D
MO
IB: sortilin
IB: β-actin
Propeptide - +
Cells
Extracellular vesicles
D(HMW)
D(LMW)

MATERIALS AND METHODS FOR EXTRACELLULAR VESSICLE-ASSOCIATED DISEASES

CROSS-REFERENCE TO RELATED APPLICATIONS

This application is a 371 National Phase Entry of International Patent Application No. PCT/US2018/057016, filed on Oct. 23, 2018, which claims benefit under 35 U.S.C. § 119(e) of U.S. Provisional Application No. 62/575,762 filed Oct. 23, 2017, the contents of both of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Nov. 14, 2018, is named 043214-093350WOPT_SL.txt and is 132,509 bytes in size.

TECHNICAL FIELD

The technology provided herein relates to methods and compositions for decreasing or inhibiting trafficking of sortilin to an extracellular vesicle.

BACKGROUND

Extracellular vesicles (EVs) play a critical role in intercellular communication by transferring microRNAs, lipids, and proteins to neighboring cells. Sortilin, a sorting receptor that directs target proteins to the secretary or endocytic compartments of cells, is found in both EVs and cells. In many human diseases, e.g., cancer and cardiovascular diseases, sortilin expression levels are atypically increased. Although recent reports have noted that sortilin is regulated by multiple post-translational modifications, the precise mechanisms of sortilin trafficking has not been elucidated. Dimerization of sortilin regulates trafficking of the receptor to extracellular vesicles. Therefore, inhibiting dimerization of sortilin can act as a new therapeutic strategy for the treatment of EV-associated diseases, including vascular calcification and cancer, among others.

Accordingly, there is a need in the art for methods and compositions for inhibiting, decreasing, and preventing trafficking of sortilin to EVs.

SUMMARY

This invention is based, in part, on the inventor's discovery inter alia that sortilin forms homodimers with an intermolecular disulfide bond at the cysteine 783 ($Cys^{783}$) residue, and that formation of the disulfide bond leads to trafficking of sortilin to extracellular vesicles (EVs). Accordingly, in one aspect, provided herein is a method for inhibiting or reducing trafficking of sortilin to an extracellular vesicle (EV) from a cell. Generally, the method comprises inhibiting covalent intermolecular dimerization of sortilin in the cell. For example, by inhibiting formation of an intermolecular disulfide bond, e.g., an intermolecular disulfide bond at $Cys^{783}$ of sortilin.

Without limitation, the cell can be any cell expressing sortilin. Exemplary cells include, but are not limited to, leukocytes, lymphocytes, macrophages, natural killer cells, dendritic cells, T cells, B cells, osteoblasts, osteoclasts, mesenchymal stem cells, endothelial cells, pancreatic cells (β, α, or γ), pancreatic polypeptide (PP) cells, hepatocytes, adipose cells, and kidney glomerulus parietals, podocytes, or proximal tubule brush border cells. Further, the dimerization can be carried out by administering or contacting the cell with an agent that inhibits, reduces or prevents sortilin dimerization, for example by inhibiting, reducing or preventing formation of an intermolecular disulfide bond.

As discussed herein, inhibiting dimerization of sortilin can be used for treating EV-associated diseases. Thus, in another aspect, provided herein is a method of treating an extracellular vesicle associated disease in subject, comprising inhibiting covalent intermolecular dimerization of sortilin in a subject in need thereof. For example, inhibiting formation of an intermolecular disulfide bond, such as at $Cys^{783}$ of sortilin. decrease, inhibit, reduce, and/or treat calcification in a subject in need thereof.

In another aspect, provided herein is a method for identifying a test agent that modulates dimerization of sortilin. The method comprises contacting a cell with a test agent, wherein the cell expresses a first sortilin polypeptide comprising a first label, and a second sortilin polypeptide comprising a second label. The labels can be same or different, and a distance or contact level between the two labels can be determined. Thus, after the cell is contacted with the test agent, a distance or contact level between the two labels is measured or determined. The distance or contact level is compared to a reference or distance or contact level. The reference or control can be a distance or contact level measured in a cell, i.e., the cell expressing a first sortilin polypeptide comprising a first label, and a second sortilin polypeptide comprising a second label, that is not contacted with the test compound. A change in distance or contact level relative to the control or reference level indicates the agent modulates dimerization of sortilin.

Any method known to one of skill in the art could be used for measuring or detecting the distance or contact level. For example, Fluorescence Resonance Energy Transfer (TR-FRET) can be used to measure the distance or contact level between the two labels. In some embodiments, the two lables can be a FRET donor and acceptor pair. In some embodiments, the ligands that can bind the two lables can be used, where the ligand that binds with the first label can comprise one of the FRET acceptor or donor and the ligand that bind the second label can comprise other of the FRET acceptor or donor.

Furthermore, provided herein is a method for preparing dimeric soluble sortilin. The method comprises expressing a sortilin polypeptide comprising a first label in an extracellular domain from a cell. The expressed sortilin polypeptide can be purified by affinity purification. For example, the affinity purification can be based on affinity for the first label. Generally, the purification is under conditions that reduce separation of sortilin dimers.

BRIEF DESCRIPTION OF THE DRAWINGS

FIG. 1A shows schematic of FLAG-sortilin and 6×His-sortilin. FLAG tag and 6×His tag were inserted following propeptide and 3 amino acids (Ser78-Ala79-Pro80) in sortilin. SP, signal peptide; PP, propeptide; TMD, transmembrane domain; ICD, intracellular domain. FIG. 1B shows overexpression of FLAG-sortilin and 6×His-sortilin in HEK293 cells was validated in western blotting. FIG. 1C-D shows detection of binding of FLAG-sortilin and 6×His-sortilin on the cell surface of HEK293 in TR-FRET assay (FIG. 1C) and HTRF assay (FIG. 1D). Change of FRET signal by expression of 6×His-sortilin was indicated as % change (mean±S.E., 3 independent experiments). t-test, *, $p<0.05$; **, $p<0.01$.

FIG. 2A shows a schematic of FLAG-sortilin full-length (Full), ECD+TMD and ICD+TMD. FIG. 2B-C shows protein expression of FLAG-sortilin Full, ECD+TMD and ICD+TMD was validated in reducing (FIG. 2B) and non-reducing (FIG. 2C) western blotting using anti-FLAG antibody. FLAG-sortilin Full and ECD+TMD forms homodimers and multimers. Empty vector was used as control. FIG. 2D shows HEK293 cells transiently overexpressing FLAG-sortilin Full or ECD+TMD were treated with cross-linker, and the cell lysates were used for reducing western blotting with anti-FLAG antibody, showing dimerization of sortilin Full and ECD+TMD (n=3). FIG. 2E shows HEK293 cells stably overexpressing FLAG-sortilin ICD+TMD (FLAG-sortilin ICD+TMD HEK293 cells) were incubated with DMSO (Control), MG-132 (MG) 20 μmol/L or chloroquine (Chlo) 10 μmol/L for 7 hours, and then reducing western blotting was performed using anti-sortilin antibody. MG-132 increased the protein expression of FLAG-sortilin ICD+TMD, but chloroquine did not (n=3). FIG. 2F shows FLAG-sortilin ICD+TMD HEK293 cells were incubated with MG-132 (2-20 μmol/L) for 7 or 24 hours. MG-132 increased FLAG-sortilin ICD+TMD in a time and concentration-dependent manner. FIG. 2G shows following 16-hour incubation of HEK293 cells (Control) or FLAG-sortilin ICD+TMD HEK293 cells (ICD+TMD) with MG-132 (5 μmol/L) and immunoprecipitation with anti-FLAG antibody, non-reducing western blotting showed dimerization of sortilin ICD+TMD using anti-sortilin antibody. Monomers, homodimers and multimers are abbreviated as MO, D and MU, respectively. IB, immunoblotting.

FIG. 3A-D shows 6×His-sortilin Full, ECD+TMD, and ICD+TMD were transiently overexpressed in HEK293 cells with stably overexpressed FLAG-sortilin Full (FIG. 3A-B) and ECD+TMD (FIG. 3C-D), respectively. Immunoprecipitation with anti-FLAG M2 antibody was performed using the cell lysates. Western blotting was carried out using whole cell lysates (FIG. 3A, C) and immunoprecipitants (FIG. 3B, D). 6×His-sortilin Full, ECD+TMD and ICD+TMD were coprecipitated with FLAG-sortilin Full or ECD+TMD (B, D) (n=2). IB, immunoblotting.

FIG. 4A shows a schematic of FLAG-sortilin CD43-TMD. Transmembrane domain of sortilin was replaced with that of CD43. FIG. 4B shows FLAG-sortilin WT and FLAG-sortilin CD43-TMD were transiently overexpressed in HEK293 cells, and non-reducing Western blotting was carried out using cell lysate with anti-FLAG antibody (n=3). Monomers, homodimers, and multimers are abbreviated as MO, D, and MU, respectively. FIG. 4C-D shows 6×His-sortilin WT or 6×His-sortilin CD43-TMD was transiently overexpressed in HEK293 cells stably overexpressing FLAG-sortilin, and immunoprecipitation was performed using anti-FLAG M2 antibody. Western blotting was carried out using whole cell lysates (FIG. 4C) and immunoprecipitants (FIG. 4D). 6×His-sortilin CD43-TMD coprecipitated with FLAG-sortilin as well as 6×His-sortilin WT. Arrows, sortilin wildtype or sortilin CD43-TMD (n=3).

FIG. 5A shows a schematic of FLAG-sortilin wild-type (WT) and C783A, and 6×His-sortilin ICD TMD WT and C783A. Cysteine 783 was replaced by Alanine. SP, signal peptide; PP, propeptide. FIG. 5B shows expression vector of 6×His-sortilin 10CC TMD was transfected in HEK293 cells. Dimerization of 6×His-sortilin 10 CC TMD was detected in non-reducing Western blotting with anti-6×His antibody (n=3). FIG. 5C-D shows C783A decreased homodimers of sortilin in the cells (FIG. 5C) and extracellular vesicles (FIG. 5D) of HEK293 cells in the non-reducing western blotting (n=3). FIG. 5D-E shows C783A decreased sortilin homodimers of low molecular weight in the cells (FIG. 5D) and extracellular vesicles (FIG. 5E) of HEK293 cells in non-reducing Western blotting (n=3). FIG. 5F-G shows 24-h incubation with 2-FPA, an inhibitor of palmitoylation, increased sortilin homodimers of low molecular weight in HEK293 cells stably overexpressing FLAG-sortilin (FIG. 5F) and their extracellular vesicles (FIG. 5G) (n=3). Monomers and homodimers of high and low molecular weight are abbreviated as MO, D(HMW), and D(LMW), respectively. IB, immunoblotting.

FIG. 6A shows a schematic of FLAG-sortilin WT, S316E and without propeptide (wp). Serine316 was replaced by glutamic acid in sortilin (S316E). Propeptide was removed in FLAG-sortilin wp. SP, signal peptide; PP, propeptide FIG. 6B shows S316E increased dimerization of sortilin in HEK293 cells (n=3). FIG. 6C shows that removal of propeptide increased dimerization of sortilin in HEK293 cells (n=3). FIG. 6D-E shows addition of propeptide (100 nmol/L) decreased dimerization of sortilin in the extracellular vesicles of FLAG-sortilin HEK293 cells (FIG. 6E), whereas a decrease in the cells was not observed (FIG. 6D) (n=2). Monomers and homodimers of high and low molecular weight are abbreviated as MO, D(HMW), D(LMW), respectively. Vex, vector; IB, immunoblotting.

FIG. 7A-B shows orientation of sortilin on the EV membrane was determined using EVs secreted from FLAG-sortilin HEK293 cells (FIG. 7A) and sortilin-3×FLAG HEK293 cells (FIG. 7B). EVs or their lysates were subjected to immunoprecipitation with anti-FLAG M2 antibody, and FLAG-sortilin (FIG. 7A) or sortilin-3×FLAG (FIG. 7B) was detected in western blotting with anti-FLAG antibody (n=3). FIG. 7C-D shows soluble sortilin secreted by HEK293 cells overexpressing FLAG-sortilin Full and FLAG-sortilin ECD+TMD was detected in non-reducing (FIG. 7C) and reducing western blotting (FIG. 7D), showing that they were homodimers and monomers, respectively (n=2). FIG. 7E shows soluble sortilin secreted by HEK293 cells overexpressing FLAG-sortilin Full and FLAG-sortilin ECD+TMD was purified and detected in non-reducing western blotting. IB, immunoblotting.

FIG. 11A shows HCASMCs were lysed 3 days after infection. Sortilin expression was detected by the non-reducing or reducing (cleavage disulfide bounds) western blotting in input sample. FIG. 11B shows the immunoprecipitated sample. Dimer form was decreased in C783A mutant and multimer form was increased in S316E mutant. MO=Monomer, D=dimer and MU=multimer. N=3 donors.

DETAILED DESCRIPTION

Figures 1A, 1B, 1C, 1D:
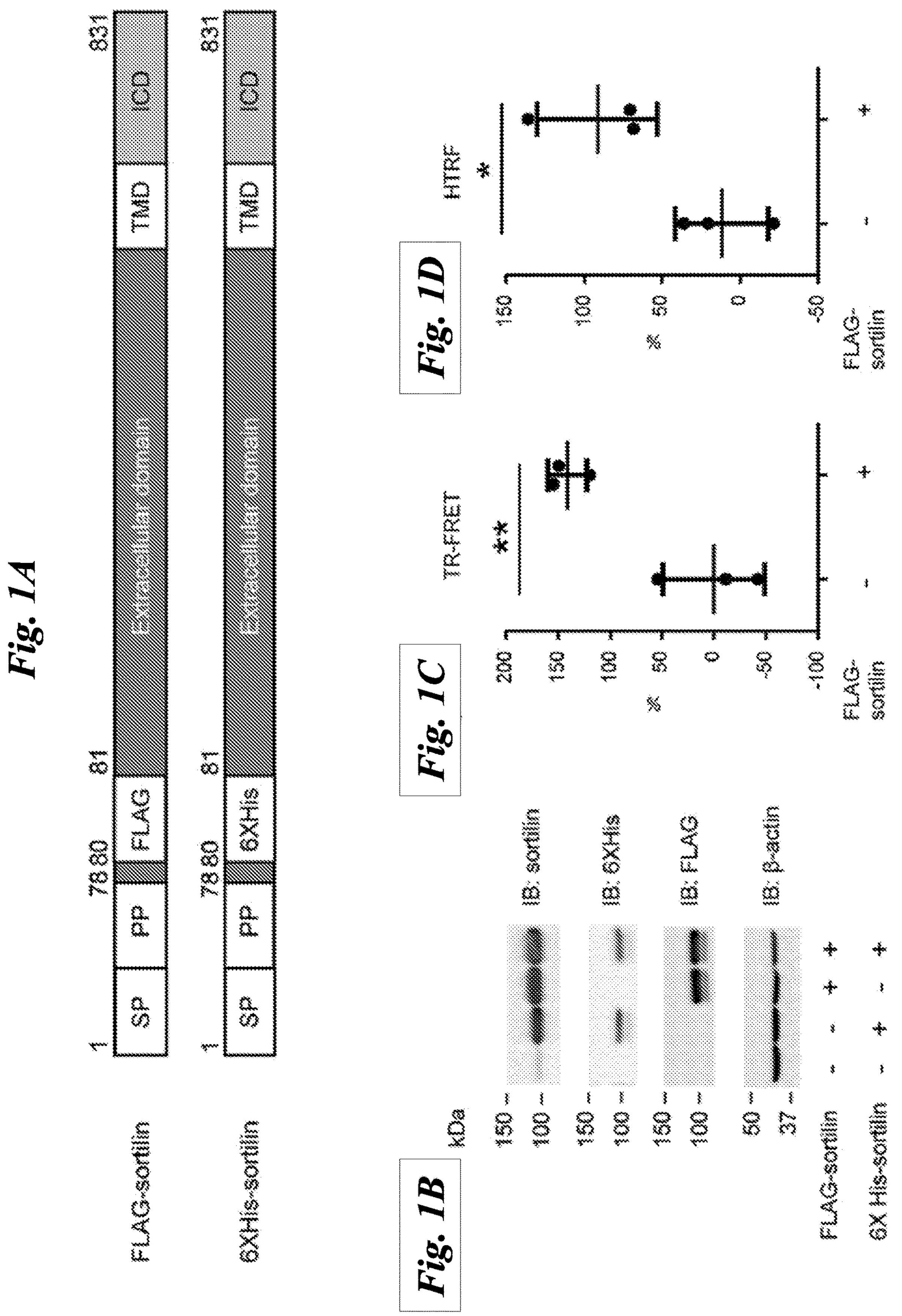
FIG. 1A-D shows that sortilin forms homodimers on the cell surface of HEK293 cells.

As used herein, the term "sortilin" or "sortilin 1" refers to a type I membrane glycoprotein in the vacuolar protein sorting 10 protein (Vps10p) family of sorting receptors that is found within or on the surface of extracellular vesicles and within cells. The protein sequence of sortilin is provided herein as SEQ ID NO: 1. Sortilin is encoded by the SORT1 gene (NCBI Reference Sequence: NG_028280.1). The human SORT1 sequence is provided herein as SEQ ID NO: 3. SORT1 or sortilin can refer to human SORT1, including naturally occurring variants, molecules, and alleles thereof. SORT1 refers to the mammalian SORT1 of, e.g., mouse, rat, rabbit, dog, cat, cow, horse, pig, and the like.

In humans, sortilin is expressed in a wide range of tissues including the brain, heart, skeletal muscle, adrenal gland, thyroid, B-lymphocytes, adipocytes, and the spinal cord. Sortilin is involved in the transport of intracellular proteins between the trans-Golgi network, endosome, lysosome, secretory granules, and between cellular plasma membranes. Exemplary proteins transported by sortilin include but are not limited to tissue non-specific alkaline phosphatase (TNAP), Caveolin-1, beta-secretase 1 (BACE 1), epidermal growth factor receptor (EGFR), tropomyosin receptor kinase B (TrkB), apolipprotein E (APOE), progranulin, amyloid precursor protein (APP), glucose transporter type 4 (GLUT4), low-density lipoprotein (LDL)-cholesterol, very low-density lipoprotein (VLDL), and proprotein convertase subtilisin/kexin type 9 (PCSK9).

In embodiments of the various aspects described herein, intermoleculkar dimerization of sortilin can be by administering or contacting a cell with an agent that inhibits, prevents or reduces intermolecular dimerization. For example, the agent inhibits, prevents or reduces formation of intermolecular disulfide bond(s) in a sortilin polypeptide.

In some embodiments of the various aspects described herein, intermolecular dimerization of sortilin is inhibited by inhibiting formation of an intermolecular disulfide formation at Cys783 of SEQ ID NO: 1.

The agent capable of inhibiting dimerization of sortilin is also referred to as an "inhibitor of sortilin" or "inhibitor" herein. Without limitations, the inhibitor, can be selected from the group consisting of a small molecule, nucleic acid, polypeptide, drug, ion, small organic or inorganic molecules, saccharines, oligosaccharides, polysaccharides, biological macromolecules, e.g., peptides, proteins, and peptide analogs and derivatives; peptidomimetics; antibodies and antigen binding fragments thereof; nucleic acids; nucleic acid analogs and derivatives; an extract made from biological materials such as bacteria, plants, fungi, or animal cells; animal tissues; naturally occurring or synthetic compositions; and any combinations thereof.

In some embodiments of the various aspects disclosed herein, the inhibitor is a peptide. As used herein, the terms "proteins" and "peptides" are used interchangeably herein to designate a series of amino acid residues connected to the other by peptide bonds between the alpha-amino and carboxy groups of adjacent residues. The terms "protein", and "peptide", which are used interchangeably herein, refer to amino acids, including modified amino acids (e.g., phosphorylated, glycated, etc.) and amino acid analogs, regardless of its size or function. Although "protein" is often used in reference to relatively large polypeptides, and "peptide" is often used in reference to small polypeptides, usage of these terms in the art overlaps and varies. The term "peptide" as used herein refers to peptides, polypeptides, proteins and fragments of proteins, unless otherwise noted. The terms "protein" and "peptide" are used interchangeably herein when referring to a gene product and fragments thereof. Thus, exemplary peptides or proteins include gene products, naturally occurring proteins, homologs, orthologs, paralogs, fragments and other equivalents, variants, fragments, and analogs of the foregoing.

In some embodiments of the various aspects disclosed herein, the inhibitor is a sortilin-derived propeptide. As used herein, the term "propeptide" refers to a peptide that is a precursor to a peptide or protein that comprises a post-translational modification such as a cleavage site to become biologically active. In some embodiments, the propeptide comprises the amino acid sequence of SEQ ID NO: 2. In one embodiment, the propeptide comprises at least on amino acid substitution or a conservative substitution of SEQ ID NO: 2. In another embodiment, the sortilin-derived propeptide is amidated, acetylated, cyclized, phosphorylated, glycosylated, nitrosylated, methylated, lipidated, or PEGylated. In another embodiment, the peptide comprises at least one D amino acid, beta amino acid or modified peptide linkage.

The term "conservative substitution," when describing a polypeptide, refers to a change in the amino acid composition of the polypeptide that does not substantially alter the polypeptide's activity, fore examples, a conservative substitution refers to substituting an amino acid residue for a different amino acid residue that has similar chemical properties. Conservative amino acid substitutions include replacement of a leucine with an isoleucine or valine, an aspartate with a glutamate, or a threonine with a serine. "Conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not substantially alter activity. Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984).) In addition, individual substitutions, deletions or additions that alter, add or delete a single amino acid or a small percentage of amino acids in an encoded sequence are also "conservative substitutions." Insertions or deletions are typically in the range of about 1 to 5 amino acids.

In some embodiments of the various aspects disclosed herein, the inhibitor is a small molecule. As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight of less than 5000 Daltons (5 kDa), preferably less than 3 kDa, still more preferably less than 2 kDa, and most preferably less than 1 kDa. In some cases, it is preferred that a small molecule have a molecular weight equal to or less than 700 Daltons.

In some embodiments of the various aspects disclosed herein, the inhibitor is a nucleic acid molecule or an analog or derivate thereof. As used herein, the term "nucleic acid" or "oligonucleotide" or grammatical equivalents herein means at least two nucleotides, including analogs or derivatives thereof that are covalently linked together. Exemplary oligonucleotides include, but are not limited to, single-stranded and double-stranded siRNAs and other RNA interference reagents (RNAi agents or iRNA agents), shRNA (short hairpin RNAs), antisense oligonucleotides, aptamers, ribozymes, and microRNAs (miRNAs). The nucleic acids can be single stranded or double stranded. The nucleic acid can be DNA, RNA or a hybrid, where the nucleic acid contains any combination of deoxyribo- and ribo-nucleotides, and any combination of uracil, adenine, thymine, cytosine and guanine. The nucleic acids can comprise one or more backbone modifications, e.g., phosphoramidate (Beaucage et al., Tetrahedron 49(10):1925 (1993) and references therein; Letsinger, J. Org. Chem. 35:3800 (1970)), phosphorothioate, phosphorodithioate, O-methylphophoroamidite linkages (see Eckstein, Oligonucleotides and Analogues: A Practical Approach, Oxford University Press), or peptide nucleic acid linkages (see Egholm, J. Am. Chem. Soc. 114:1895 (1992); Meier et al., Chem. Int. Ed. Engl. 31:1008 (1992); and Nielsen, Nature, 365:566 (1993), content of all of which is herein incorporated by reference. The nucleic acids can also include modifications to nucleobase and/or sugar moieties of nucleotides. Exemplary sugar modifications at the sugar moiety include replacement of 2'-OH with halogens (e.g., fluoro), O-methyl, 0-methoxyethyl, NH2, SH and S-methyl. In some embodiments, the nucleic acid is a peptide nucleic acid (PNA). Without wishing to be bound by a theory, nucleic acid inhibitors can decrease, inhibit, or reduce the expression or amount of the nucleic acid encoding a component of the complex. Computational and experimental methods, including high throughput screening assays, for producing nucleic acid inhibitors, e.g., antisense oligonucleotides, siRNAs, ribozymes, aptamers, and the like, targeted to any target sequence are known in the art and available to one of skill in the art.

The term "oligonucleotide" as used herein refers to a short nucleic acid polymer, typically with twenty or fewer bases.

The term "shRNA" as used herein refers to short hairpin RNA which functions as RNAi and/or siRNA species but differs in that shRNA species are double stranded hairpin-like structure for increased stability. The term "RNAi" as used herein refers to interfering RNA, or RNA interference molecules are nucleic acid molecules or analogues thereof for example RNA-based molecules that inhibit gene expression. RNAi refers to a means of selective post-transcriptional gene silencing. RNAi can result in the destruction of specific mRNA, or prevents the processing or translation of RNA, such as mRNA.

In some embodiments, the inhibitor is short interfering RNA (siRNA). The term "short interfering RNA" (siRNA), also referred to herein as "small interfering RNA" is defined as an agent which functions to inhibit expression of a target gene, e.g., by RNAi. A siRNA can be chemically synthesized, it can be produced by in vitro transcription, or it can be produced within a host cell. siRNA molecules can also be generated by cleavage of double stranded RNA, where one strand is identical to the message to be inactivated. The term "siRNA" refers to small inhibitory RNA duplexes that induce the RNA interference (RNAi) pathway. These molecules can vary in length (generally 18-30 base pairs) and contain varying degrees of complementarity to their target mRNA in the antisense strand. Some, but not all, siRNA have unpaired overhanging bases on the 5' or 3' end of the sense strand and/or the antisense strand. The term "siRNA" includes duplexes of two separate strands, as well as single strands that can form hairpin structures comprising a duplex region.

In some embodiments, the inhibitor is an antisense oligonucleotide or siRNA molecule comprising a part of (e.g., 10-50, 12-40, 15-30, 16-25, or 18-22 consecutive nucleotides) of the antisense sequence of a nucleic acid encoding sortilin, e.g. SORT 1. Nucleic acid sequence of human sortilin proteins can be accessed by NCBI Reference Gene ID: 6272, NCBI Reference Sequence: NG_028280.1, and SEQ ID NO: 3. In some embodiments, the nucleic acid encoding sortilin is SORT mRNA.

In some embodiments, the inhibitor is an aptamer. As used herein, the term "aptamer" means a single-stranded, partially single-stranded, partially double-stranded or double-stranded nucleotide sequence capable of specifically recognizing a selected non-oligonucleotide molecule or group of molecules. Accordingly, aptamers are nucleic acid or peptide molecules that bind to a particular molecule of interest with high affinity and specificity (Tuerk and Gold, Science 249: 505 (1990); Ellington and Szostak, Nature 346:818 (1990)). DNA or RNA aptamers have been successfully produced which bind many different entities from large proteins to small organic molecules. See Eaton, Curr. Opin. Chem. Biol. 1:10-16 (1997), Famulok, Curr. Opin. Struct. Biol. 9:324-9 (1999), and Hermann and Patel, Science 287:820-5 (2000). Aptamers can be RNA or DNA based. Methods for selecting aptamers for binding to a molecule are widely known in the art and easily accessible to one of ordinary skill in the art. Generally, aptamers are engineered through repeated rounds of in vitro selection or equivalently, SELEX (systematic evolution of ligands by exponential enrichment) to bind to various molecular targets such as small molecules, proteins, nucleic acids, and even cells, tissues and organisms. The aptamer can be prepared by any known method, including synthetic, recombinant, and purification methods, and can be used alone or in combination with other aptamers specific for the same target. Further, as described more fully herein, the term "aptamer" specifically includes "secondary aptamers" containing a consensus sequence derived from comparing two or more known aptamers to a given target. Aptamers can include, without limitation, defined sequence segments and sequences comprising nucleotides, ribonucleotides, deoxyribonucleotides, nucleotide analogs, modified nucleotides and nucleotides comprising backbone modifications, branchpoints and nonnucleotide residues, groups or bridges. In some embodiments, the aptamer recognizes the non-oligonucleotide molecule or group of molecules by a mechanism other than Watson-Crick base pairing or triplex formation.

As used herein, the term "polysaccharide" refers to macromolecular carbohydrates whose molecule consists of a large number of monosaccharide molecules which are joined to one another by glycosidic linkage. The term polysaccharide is also intended to embrace an oligosaccharide. The polysaccharide can be homopolysaccharides or heteropolysaccharides. Whereas the homopolysaccharides contain only one kind of unit, the heteropolysaccharides consist of monomer units of different kinds.

In some embodiments, the inhibitor is an antibody or a fragment thereof. The terms "antibody" and "antibodies" include polyclonal antibodies, monoclonal antibodies, humanized or chimeric antibodies, single chain Fv antibody fragments, Fab fragments, and F(ab)2 fragments. Antibodies having specific binding affinity for sortilin 1 can be produced through standard methods. Alternatively, antibodies can be commercially available, for example, from R&D Systems, Inc., Minneapolis, Minn.

As used herein, the terms "antibody" and "antibodies" include intact antibody, or a binding fragment thereof that competes with the intact antibody for specific binding and includes chimeric, humanized, fully human, and bispecific antibodies. In some embodiments, binding fragments are produced by recombinant DNA techniques. In additional embodiments, binding fragments are produced by enzymatic or chemical cleavage of intact antibodies. Binding fragments include, but are not limited to, Fab, Fab', F(ab')2, Fv, and single-chain antibodies.

Unless it is specifically noted, as used herein a "fragment thereof" in reference to an antibody refers to an immunospecific fragment, i.e., an antigen-specific or binding fragment.

Monoclonal antibodies, which are homogeneous populations of antibodies to a particular epitope contained within an antigen, can be prepared using standard hybridoma technology. In particular, monoclonal antibodies can be obtained by any technique that provides for the production of antibody molecules by continuous cell lines in culture such as described by Kohler, G. et al., Nature, 1975, 256:495, the human B-cell hybridoma technique (Kosbor et al., Immunology Today, 1983, 4:72; Cole et al., Proc. Natl. Acad. Sci. USA, 1983, 80:2026), and the EBV-hybridoma technique (Cole et al., Monoclonal Antibodies and Cancer Therapy, Alan R. Liss, Inc., 1983, pp. 77-96). Such antibodies can be of any immunoglobulin class including IgG, IgM, IgE, IgA, IgD, and any subclass thereof. The hybridoma producing the monoclonal antibodies of the invention can be cultivated in vitro or in vivo.

Polyclonal antibodies are heterogeneous populations of antibody molecules that are specific for a particular antigen, which are contained in the sera of the immunized animals. Polyclonal antibodies are produced using well-known methods. A chimeric antibody is a molecule in which different portions are derived from different animal species, such as those having a variable region derived from a murine monoclonal antibody and a human immunoglobulin constant region. Chimeric antibodies can be produced through standard techniques. Antibody fragments that have specific binding affinity for a component of the complex can be generated by known techniques. For example, such fragments include, but are not limited to, F(ab')2 fragments that can be produced by pepsin digestion of the antibody molecule, and Fab fragments that can be generated by reducing the disulfide bridges of F(ab')2 fragments. Alternatively, Fab expression libraries can be constructed. See, for example, Huse et al., 1989, Science, 246: 1275. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques. See, for example, U.S. Pat. No. 4,946,778.

In some embodiments, the antibody or antigen-binding fragment thereof is murine. In some embodiments, the antibody or antigen-binding fragment thereof is from rabbit. In some embodiments, the antibody or antigen-binding fragment thereof is from rat. In other embodiments, the antibody or antigen binding fragment thereof is human. In some embodiments the antibody or antigen-binding fragment thereof is recombinant, engineered, humanized and/or chimeric.

In some embodiments, an antibody, or antigen binding fragment, variant, or derivative thereof for use in the methods of the invention binds specifically to at least one epitope of target molecule (e.g., sortilin), i.e., binds to such an epitope more readily than it would bind to an unrelated, or random epitope; binds preferentially to at least one epitope of sortilin, i.e., binds to such an epitope more readily than it would bind to a related, similar, homologous, or analogous epitope; competitively inhibits binding of a reference antibody which itself binds specifically or preferentially to an epitope of the target molecule (e.g., sortilin); or binds to at least one epitope of the target molecule (e.g., sortilin) with an affinity characterized by a dissociation constant Kd of about $5\times10^{-2}$ M, about $10^{-2}$ M, about $5\times10^{-3}$ M, about $10^{-3}$M, about $5\times10^{-4}$ M, about $10^{-5}$ M, about $5\times10^{-5}$ M, about $10^{-5}$ M, about $5\times10^{-4}$ M, about $10^{-6}$ M, about $5\times10^{-7}$ M, about $10^{-8}$ M, about $5\times10^{-8}$ M, about $10^{-8}$ M, about $5\times10^{-9}$ M, about $10^{-9}$ M, about $5\times10^{-10}$ M, about $10^{-1}$ M, about $5\times10^{-11}$ M, about $10^{-11}$ M, about $5\times10^{-12}$ M, about $10^{-12}$ M, about $5\times10^{-13}$ M, about $10^{-13}$ M, about $5\times10^{-14}$ M, about $10^{-14}$ M, about $5\times10^{-15}$ M, or about $10^{-15}$ M.

In some embodiments, the antibody or fragment thereof preferentially binds to a human sortilin polypeptide or fragment thereof, relative to a murine sortilin polypeptide or fragment thereof.

As used in the context of antibody binding dissociation constants, the term "about" allows for the degree of variation inherent in the methods utilized for measuring antibody affinity. For example, depending on the level of precision of the instrumentation used, standard error based on the number of samples measured, and rounding error, the term "about $10^{-2}$ M" can include, for example, from 0.05 M to 0.005 M.

In some embodiments, an antibody, or antigen binding fragment, variant, or derivative thereof for use in the methods provided herein binds sortilin polypeptides or fragments or variants thereof with an off rate (k(off)) of less than or equal to about $5\times10^{-2}$ sec-1, about $10^{-2}$ sec-1, about $5\times10^{-3}$ sec-1, about $10^{-3}$ sec-1, about $5\times10^{-4}$ sec-1, about $10^{-4}$ sec-1, about $5\times10^{-4}$ sec-1, about $10^{-4}$ sec-1, about $5\times10^{-5}$ sec-1, about $10^{-5}$ sec-1, about $5\times10^{-6}$ sec-1, about $10^{-6}$ sec-1, about $5\times10^{-7}$ sec-1, or about $10^{-7}$ sec-1.

In other embodiments, an antibody, or antigen-binding fragment, variant, or derivative thereof for use in the methods provided herein binds sortilin polypeptides or fragments or variants thereof with an on rate (k(on)) of greater than or equal to about $10^3$ M-1 sec-1, about $5\times10^3$ M-1 sec-1, $10^4$ M-1 sec-1, about $5\times10^4$ M-1 sec-1, $10^5$ M-1 sec-1, about $5\times10^5$ M-1 sec-1, $10^6$ M-1 sec-1, about $5\times10^6$ M-1 sec-1, $10^7$ M-1 sec-1, or about $5\times10^7$ M-1 sec-1. The binding affinity and dissociation rate of an antibody for use in the methods provided herein can be determined by any method known in the art. For example, the binding affinity can be measured by competitive ELISAs, RIAs, BIACORE™, or KINEXA™ technology. The dissociation rate also can be measured by BIACORE™ or KINEXA™ technology.

In some embodiments, an antibody or an antigen-binding fragment for use in the methods provided herein modulates the binding of a second molecule to sortilin. In some embodiments, the modulation is enhancement of the binding of the second molecule to sortilin. In some embodiments, the modulation is inhibition of the binding of the second molecule to sortilin. The IC50 of such inhibition can be measured by any method known in the art, e.g., by ELISA, RIA, or Functional Antagonism. In some embodiments, the IC50 is between 0.1 and 500 nM. In some embodiments, the IC50 is between 10 and 400 nM. In yet other embodiments, the antibody or portion thereof has an IC50 of between 60 nM and 400 nM.

Antibodies for use in the methods of the invention can be generated by immunization of a suitable host (e.g., vertebrates, including humans, mice, rats, sheep, goats, pigs, cattle, horses, reptiles, fishes, amphibians, and in eggs of birds, reptiles and fish). Such antibodies can be polyclonal or monoclonal. In some embodiments, the host is immunized with an immunogenic sortilin. In other embodiments, the host is immunized with sortilin associated with a cell membrane of an intact or disrupted cell and antibodies for use in the methods of the invention are identified by binding to sortilin.

In some embodiments, the sortilin antigen is administered with an adjuvant to stimulate the immune response. Adjuvants often need to be administered in addition to antigen in order to elicit an immune response to the antigen. These adjuvants are usually insoluble or nondegradable substances that promote nonspecific inflammation, with recruitment of mononuclear phagocytes at the site of immunization. Examples of adjuvants include, but are not limited to, Freund's adjuvant, RIBI (muramyl dipeptides), ISCOM (immunostimulating complexes) or fragments thereof.

For a review of methods for making antibodies, see, e.g., Harlow and Lane, Antibodies, A Laboratory Manual (1988); Yelton, D. E. et al., Ann. Rev. of Biochem. 50:657-80. (1981); and Ausubel et al., Current Protocols in Molecular Biology (New York: John Wiley & Sons) (1989). Determination of immunoreactivity with an immunogenic sortilin polypeptide can be made by any of several methods well known in the art, including, e.g., immunoblot assay and ELISA.

Anti-sortilin antibodies for use in the methods provided herein can be of any isotype. An antibody of any desired isotype can be produced by class switching. For class switching, nucleic acids encoding $V_L$ or $V_H$, that do not include any nucleotide sequences encoding $C_L$ or $C_H$, are isolated using methods well known in the art. The nucleic acids encoding $V_L$ or $V_H$ are then operatively linked to a nucleotide sequence encoding a $C_L$ or $C_H$ from a desired class of immunoglobulin molecule. This can be achieved using a vector or nucleic acid that comprises a $C_L$ or $C_H$ chain, as described above. For example, an anti-sortilin antibody for use in the methods provided herein that was originally IgM can be class switched to an IgG. Further, the class switching can be used to convert one IgG subclass to another, e.g., from IgG1 to IgG2.

The class and subclass of anti-sortilin antibodies can be determined by any method known in the art. In general, the class and subclass of an antibody can be determined using antibodies that are specific for a particular class and subclass of antibody. Such antibodies are available commercially. The class and subclass can be determined by ELISA, Western Blot, as well as other techniques. Alternatively, the class and subclass can be determined by sequencing all or a portion of the constant domains of the heavy and/or light chains of the antibodies, comparing their amino acid sequences to the known amino acid sequences of various class and subclasses of immunoglobulins, and determining the class and subclass of the antibodies.

In certain embodiments, both the variable and constant regions of sortilin antibodies or immunospecific fragments thereof for use in the treatment methods disclosed herein are fully human. Fully human antibodies can be made using techniques that are known in the art and as provided herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140. Other techniques are known in the art. Fully human antibodies can likewise be produced by various display technologies, e.g., phage display or other viral display systems, as described in more detail elsewhere herein.

Antibodies or fragments thereof for use in the treatment methods disclosed herein include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, or derivatization by known protecting/blocking groups, proteolytic cleavage, linkage to a cellular ligand or other protein. Any of numerous chemical modifications can be carried out by known techniques, including, but not limited to, specific chemical cleavage, acetylation, formylation, etc. Additionally, the derivative can contain one or more non-classical amino acids.

In some embodiments, antibody or fragment thereof for use in the methods disclosed herein will not elicit a deleterious immune response in the mammal to be treated, e.g., in a human. In one embodiment, the antibodies or fragments thereof for use in the methods disclosed herein can be modified to reduce their immunogenicity using art-recognized techniques. For example, antibodies can be humanized, primatized, deimmunized, or chimeric antibodies can be made. These types of antibodies are derived from a nonhuman antibody, typically a murine or primate antibody, that retains or substantially retains the antigen-binding properties of the parent antibody, but which is less immunogenic in humans. This can be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., Proc. Natl. Acad. Sci. USA 81:6851-6855 (1984); Morrison et al., Adv. Immunol. 44:65-92 (1988); Verhoeyen et al., Science 239:15341536 (1988); Padlan, Molec. Immun. 28:489-498 (1991); Padlan, Molec. Immun. 31:169-217 (1994), and U.S. Pat. Nos. 5,585,089; 5,693,761; 5,693,762; and 6,190,370, all of which are hereby incorporated by reference in their entirety.

De-immunization can also be used to decrease the immunogenicity of an antibody. As used herein, the term "de-immunization" includes alteration of an antibody to modify T cell epitopes (see, e.g., WO9852976A1, WO0034317A2). For example, VH and VL sequences from the starting antibody are analyzed and a human T cell epitope "map" from each V region showing the location of epitopes in relation to complementarity-determining regions (CDRs) and other key residues within the sequence. Individual T cell epitopes from the T cell epitope map are analyzed in order to identify alternative amino acid substitutions with a low risk of altering activity of the final antibody. A range of alternative VH and VL sequences are designed comprising combinations of amino acid substitutions and these sequences are subsequently incorporated into a range of binding polypeptides, e.g., anti-sortilin antibodies or immunospecific fragments thereof for use in the methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

Completely human antibodies are particularly desirable for therapeutic treatment of human patients. Human antibodies can be made by a variety of methods known in the art including phage display methods using antibody libraries derived from human immunoglobulin sequences. See, for example, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a desired target polypeptide. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety.

Completely human antibodies which recognize a selected epitope can be generated using a technique referred to as "guided selection." In this approach a selected nonhuman monoclonal antibody, e.g., a mouse antibody, is used to guide the selection of a completely human antibody recognizing the same epitope. (Jespers et al., Bio/Technology 12:899-903 (1988)). See also, U.S. Pat. No. 5,565,332. [0162] In another embodiment, DNA encoding desired monoclonal antibodies can be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA can be placed into expression vectors, which are then transfected into prokaryotic or eukaryotic host cells such as *E. coli* cells, simian COS cells, Chinese Hamster Ovary (CHO) cells or myeloma cells that do not otherwise produce immunoglobulins. More particularly, the isolated DNA (which can be synthetic as provided herein) can be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody can be grown up in relatively large quantities to provide clinical and commercial supplies of the immunoglobulin.

Anti-sortilin antibodies can be purchased from Abcam (Cambridge, Mass., USA) or R&D Systems (Minneapolis, Minn., USA). Further, methods for identification and design of ligands capable of binding specifically to Sortilin are described, for example, in US Patent Application Publication No. 2011/1060439, content of which is incorporated herein by reference.

For inhibiting the dimerization of sortilin, the agent, i.e., the inhibitor, can be administered to the cell or contacted with the cell. Without limitations, the agent can be administered to the cell or contacted with the cell in a cell culture e.g., in vitro or ex vivo, or the agent can be administrated to a subject, e.g., in vivo. In some embodiments, the agent can be administrated to a subject to inhibit intermolecular dimerization of sortilin.

The term "contacting" or "contact" as used herein in connection with contacting a cell includes subjecting the cells to an appropriate culture media, which comprises the indicated inhibitor. Where the cell is in vivo, "contacting" or "contact" includes administering the inhibitor in a pharmaceutical composition to a subject via an appropriate administration route such that the inhibitor contacts the cell in vivo.

The term "ex vivo" refers to cells which are removed from a living organism and cultured outside the organism (e.g., in a test tube). If ex vivo methods are employed, cells or tissues can be removed and maintained outside the body according to standard protocols well known in the art. The compositions can be introduced into the cells via methods known or available to one of skill in the art. For example, the cells can be kept in a culture and inhibitor can be added to the culture media. The treated cells can then be infused (e.g., in a pharmaceutically acceptable carrier) or homotopically transplanted back into the subject per standard methods for the cell or tissue type. Standard methods are known for transplantation or infusion of various cells into a subject.

As provided herein, the inhibitor can be administered in a pharmaceutically acceptable carrier and can be delivered to the subject's cells in vivo and/or ex vivo by a variety of mechanisms well known in the art.

Generally, any amount of the agent can be contacted with the cell. In some embodiments, the agent is contacted at a concentration in the range of from about 0.1 nM to about 1000 mM. Preferably the compound is contacted in the range of from about 0.1 μM to about 10 μM. Additionally, the compound can be contacted with the cell for a sufficient time to allow the compound to be taken up by the cell and interact with its target.

As disclosed herein, the cell can be contacted with the inhibitor in a cell culture e.g., in vitro or ex vivo, or the inhibitor can be administrated to a subject, e.g., in vivo. In some embodiments, the inhibitor can be administrated to a subject to decrease, inhibit, reduce, and/or treat calcification.

In some embodiments, the cell is a leukocyte, lymphocyte, macrophage, natural killer cell, dendritic cell, T cell, or B cell. In some embodiments, the cell is an interstitial valvular cell. In some embodiments, the cell is an osteoblast. In some embodiments, the cell is an osteoclast. In some embodiments, the cell is a mesenchymal stem cell. In some embodiments, the cell is an endothelial cell. In some embodiments, the cell is a pancreatic β, α, γ, or pancreatic polypeptide (PP) cell. In some embodiments the cell is a hepatocyte. In some embodiments, the cell is a kidney glomerulus parietal, podocyte, or proximal tubule brush border cell. In some embodiments, the cell is an adipose cell. In some embodiments, the cell is a macrophage. In some embodiments, the cell is a monocyte. In some embodiments, the cell is a dendritic cell. In some embodiments, the cell is a lymphocyte. In some embodiments, the cell is a vascular smooth muscle cell.

In some embodiments, the inhibitor can be administered to a subject in conjunction with surgical and non-surgical treatments. In some embodiments, the methods disclosed herein can be practiced in injunction with dialysis.

As disclosed herein, inhibiting intermolecular dimerization of sortilin can be beneficial for treating EV-associated diseases. Accordingly, in another aspect, provided herein is a method for treating an EV-associated disease in a subject. Generally, the method comprises inhibiting covalent intermolecular dimerization of sortilin subject in need thereof. For example, inhibiting formation of an intermolecular disulfide bond at the $Cys^{783}$ of sortilin. In some embodiments, the method comprises administering an agent to a subject in need thereof, wherein the agent inhibits intermolecular dimerization. In some embodiments, the agent that is administered to the subject is a sortilin propeptide.

As used herein, an "extracellular vesicle-associated disease" or "EV-associated disease" refers to a disease that has been diagnosed, suspected, or has not yet developed in a subject that is caused by aberrant extracellular vesicle trafficking, calcification of extracellular vesicles, or mislocalization of extracellular vesicles that results in at least one symptom and/or characteristic of the disease (e.g. calcification, inflammation, vesicle accumulation, pain, fatigue, shortness of breath, etc). The EV-associated disease can be caused by trafficking of sortilin, a sortilin dimer, or multimer to an extracellular vesicle(s) from a cell. As provided herein, the EV-associated disease can have variable expression of monomers and dimers of soluble sortilin, and the monomer/dimer ratio in serum for these diseases can be used for the diagnosis, prevention, and treatment of the EV-associated disease.

Extracellular vesicles are known in the art to contribute to physiology and pathology of various diseases (See Krohn and Aikawa et al. *Journal of Physiology,* 2016). Furthermore, sortilin has been found to be elevated in serum levels of subjects with aortic calcification and genome wide association studies have shown that sortilin is associated with cardiovascular calcification (See Goettsch, *JCI,* 2016; and Goettsch et al. *Arterioscler. Thromb. Vasc. Biol.,* 2018). Thus, the dimerization and trafficking of sortilin by extracellular vesicles is a characteristic of EV-associated diseases as provided herein.

Non-limiting examples of EV-associated diseases include but are not limited to calcific aortic valve disease, diabetes, systemic lupus erythematosus, ulcerative colitis, pulmonary fibrosis, nan-alcoholic fatty liver disease, osteoporosis, neurodegenerative disorders (e.g. Alzheimer's disease), scleroderma, atherosclerosis, myocardial infarction, hypercholesterolemia, cancer, rheumatoid arthritis, and obesity. In one embodiment, the diabetes is type 1 diabetes, type 2 diabetes, or maturity onset diabetes in the young. In another embodiment, the cancer is lung cancer or pancreatic cancer. In some embodiments, the EV-associated disease is acute kidney injury (AKI) or chronic kidney disease (CKD).

EV-associated diseases can be caused by extracellular vesicle-derived microcalficiations. These microcalcifications contribute to plaque instability (See also Goettsch et al. *Circ Research,* 2013). Identification of extracellular vesicle microcalcification, e.g., of the aortic valve, can be determined by structure illumination methods, zeta potential, confocal microscopy, Fourier-transform infrared spectroscopy (FTIR), X-ray spectroscopy, scanning electron microscopy (SEM), transmission electron microscopy (TEM), finite element analysis (FEA), or any other methods known in the art that can identify various stages of microcalcification (See also Hutechnson et al. *Nature Materials* 2016).

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects provided herein, the subject is a mammal, e.g., a primate, e.g., a human. The terms, "patient" and "subject" are used interchangeably herein.

In some embodiments, the subject is a mammal. The mammal can be a human, non-human primate, mouse, rat, dog, cat, horse, or cow, but are not limited to these examples. Mammals other than humans can be advantageously used as subjects that represent animal models of disorders.

The subject can be initially diagnosed by a licensed physician and/or authorized medical practitioner, and a regimen for prophylactic and/or therapeutic treatment via a method provided herein can be suggested, recommended or prescribed. Thus, in some embodiments, the method comprises selecting a subject for treatment for an EV-associated disease (e.g. vascular calcification).

Animal models that are reliable indicators of EV-associated diseases, that include but are not limited to human atherosclerosis, renal failure, hyperphosphatemia, diabetes, age-related vascular calcification and other conditions associated with vascular calcification are known in the art. For example, an experimental model of calcification of the vessel wall is described by Yamaguchi et al., Exp. Path. 25: 185-190, 1984, content of which is incorporated herein by reference in its entirety.

By "treatment or amelioration" is reversing, alleviating, ameliorating, inhibiting, slowing down or stopping the progression, aggravation or deterioration the progression or severity of a condition. In some embodiments, at least one symptom is alleviated by at least 20%, at least 30%, at least 40%, at least 50%, at least 60%, at least 70%, at least 80%, at least 90%, or at least 95% but not 100%, i.e. not a complete alleviation. In some embodiments, at least one symptom is completely alleviated.

The terms "therapeutic agents" or "agent" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a therapeutic agent can be used which are capable of being released from the subject composition into adjacent tissues or fluids upon administration to a subject. Examples include steroids and esters of steroids (e.g., estrogen, progesterone, testosterone, androsterone, cholesterol, norethindrone, digoxigenin, cholic acid, deoxycholic acid, and chenodeoxycholic acid), boron-containing compounds (e.g., carborane), chemotherapeutic nucleotides, drugs (e.g., antibiotics, antivirals, antifungals), enediynes (e.g., calicheamicins, esperamicins, dynemicin, neocarzinostatin chromophore, and kedarcidin chromophore), heavy metal complexes (e.g., cisplatin), hormone antagonists (e.g., tamoxifen), non-specific (non-antibody) proteins (e.g., sugar oligomers), oligonucleotides (e.g., antisense oligonucleotides that bind to a target nucleic acid sequence (e.g., mRNA sequence)), peptides, proteins, antibodies, photodynamic agents (e.g., rhodamine 123), radionuclides (e.g., I-131, Re-186, Re-188, Y-90, Bi-212, At-211, Sr-89, Ho-166, Sm-153, Cu-67 and Cu-64), toxins (e.g., ricin), and transcription-based pharmaceuticals.

As used herein, the terms "inhibiting," "decreasing," "preventing," and "treating" in connection with an EV-associated disease, are intended to mean preventing, retarding, or reversing formation, translocation of extracellular vesicle and/or the growth or deposition of extracellular matrix hydroxyapatite crystal deposits. Without limitations, the improvement in disorder severity includes the reversal of the disease symptoms, as well as slowing down the progression of the disease.

For example, inhibiting formation of an intermolecular disulfide bond at Cys783 of SEQ ID NO: 1. The Cys783 is indicated within the sequence as bolded and underlined (e.g. C). The dimerization of sortilin can be inhibited by an agent, for example, a sortilin-derived propeptide.

Figure 8:
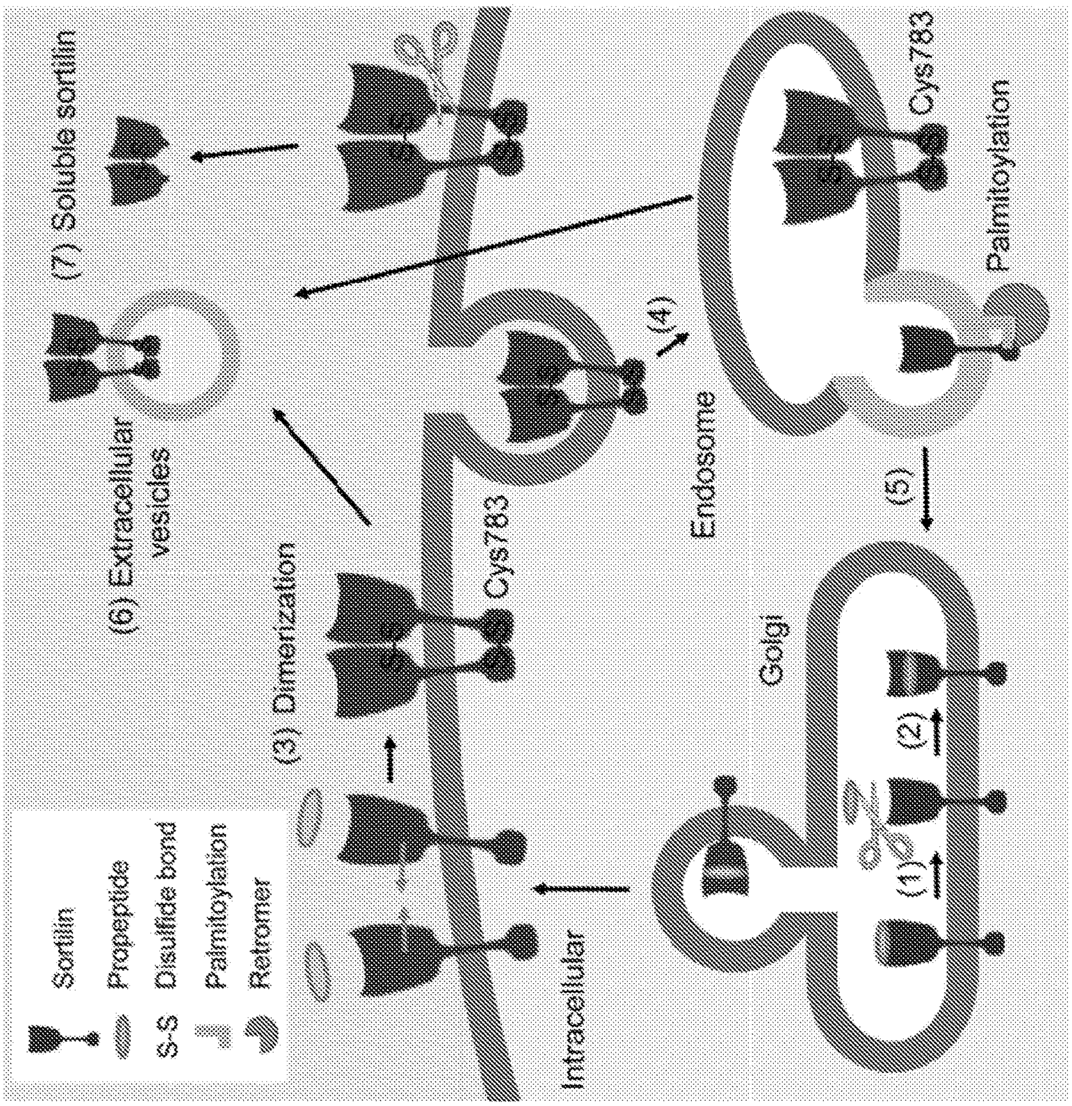
FIG. 8 shows a schematic figure showing involvement of dimerization for trafficking of sortilin and the regulation by propeptide. Dissociation of propeptide from sortilin promoted dimerization. Dimerization with an intermolecular disulfide bond at $Cys^{783}$ facilitated transport of dimerized sortilin to the extracellular vesicles. $Cys^{783}$ is associated with dimerization and palmitoylation. Palmitoylated sortilin is transported back to the Golgi apparatus. (1) Propeptide is cleaved from sortilin. (2) Propeptide binds to sortilin at different location. Then, sortilin is transported through the Golgi apparatus. (3) Sortilin forms homodimers with intermolecular disulfide bonds at 10 CC domain and $Cys^{783}$. (4) Sortilin is incorporated to endosome by endocytosis. (5) Palmitoylated sortilin monomer is transported back to Golgi by interaction with retromer. (6) Sortilin homodimer is secreted by extracellular vesicles (microvesicles and/or exosomes). (4) Sortilin homodimer is shedded and secreted as soluble sortilin.
Figure 9:
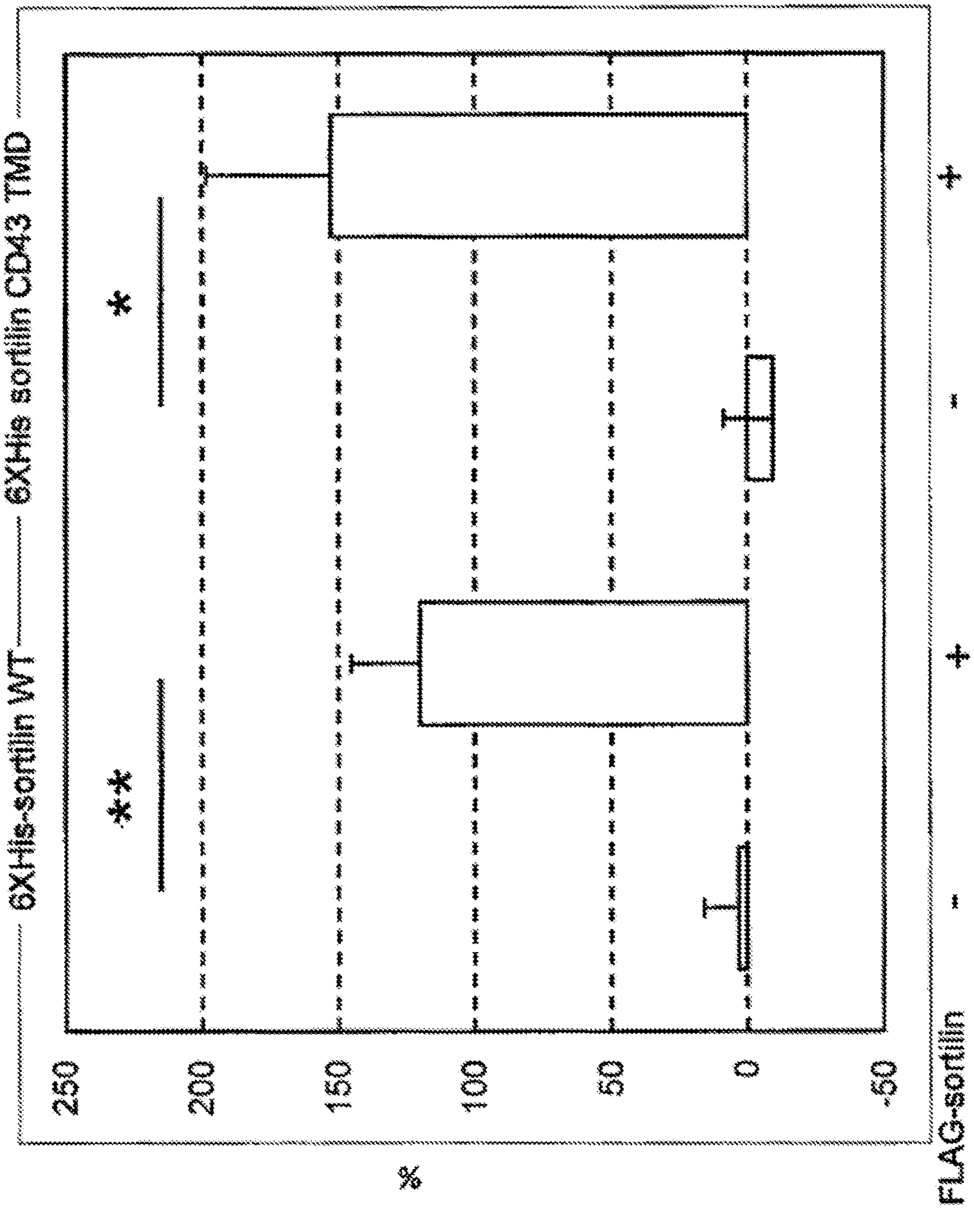
FIG. 9 shows that in FLAG-sortilin HEK293 cells or HEK293 cells, 6×His-sortilin, CD43-TMD was overexpressed. The cells were subjected to TR-FRET assay. Change of FRET signal by expression of 6×His-sortilin wild-type (WT) or CD43-TMD was indicated as % change (mean±S.E., n=4, 1 independent experiment). t-test, *$P<0.05$; **, $p<0.01$.

FIG. 8 shows a schematic of the molecular mechanisms of sortilin cleavage and trafficking to extracellular vesicles. Specifically, the schematic highlights that the dissociation of propeptide from sortilin that promotes dimerization. Dimerization with the intermolecular disulfide bond at $Cys^{783}$ facilitates transport of dimerized sortilin to the extracellular vesicles. Furthermore, $Cys^{783}$ is associated with dimerization and palmitoylation.

Palmitoylated sortilin is transported back to the Golgi apparatus. According to FIG. 8, the steps of sortilin trafficking within a cell comprise: (1) Propeptide is cleaved from sortilin; (2) propeptide binds to sortilin at different location and sortilin is transported through the Golgi apparatus; (3) sortilin forms homodimers with intermolecular disulfide bonds at 10CC domain and $Cys^{783}$; (4) sortilin is incorporated to endosome by endocytosis; (5) palmitoylated sortilin monomer is transported back to Golgi by interaction with retromer; (6) sortilin homodimer is secreted by extracellular vesicles (microvesicles and/or exosomes); and (4) sortilin homodimer is shedded and secreted as soluble sortilin. Thus, the test agents provided herein can inhibit any portion of sortilin dimerization or trafficking as outlined by FIG. 8.

In one aspect, provided herein is a method for inhibiting intermolecular dimerization of sortilin in a subject comprising administering an agent to the subject in need thereof. In some embodiments, the inhibition of sortilin comprises administering a peptide to the subject in need thereof.

As used herein, the term "administer" refers to the placement of a composition into a subject by a method or route which results in at least partial localization of the pharmaceutically active agent at a desired site. The inhibitors can be administered in any suitable manner. The manner of administration can be chosen based on, for example, whether local or systemic treatment is desired, and on the area to be treated. Accordingly, a composition can be administered by any appropriate route which results in effective treatment in the subject, i.e., administration results in delivery to a desired location in the subject where at least a portion of the pharmaceutically active agent is delivered. Exemplary modes of administration include, but are not limited to, implant, injection, infusion, instillation, implantation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion.

In some embodiments, a composition provided herein can be implanted in a subject. As used herein, the term "implanted," and grammatically related terms, refers to the positioning of the composition in a particular locus in the subject, either temporarily, semi-permanently, or permanently. The term does not require a permanent fixation of the composition in a particular position or location.

With respect to duration and frequency of administration or treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the polypeptides. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments, administration is chronic, e.g., one or more doses daily over a period of weeks or months. Examples of dosing schedules are administration once a month, once every two weeks, once a week, once every other day, daily, twice daily, three times daily or four or more times daily over a period of 1 week, 2 weeks, 3 weeks, 4 weeks, 1 month, 2 months, 3 months, 4 months, 5 months, or 6 months or more.

In some embodiments, the sortilin dimerization inhibitor can be co-administered to the subject in combination with a pharmaceutically active agent or therapeutic agent. Without limitations, the inhibitor can be administered before, concurrently, or after administration of the therapeutic agent. Thus, as used herein, the term "co-administer" refers to administration of two or more agents (e.g., the inhibitor and the pharmaceutically active agent) within a 24-hour period of each other, for example, as part of a clinical treatment regimen. In other embodiments, "co-administer" refers to administration within 12 hours, within 6 hours, within 5 hours, within 4 hours, within 3 hours, within 2 hours, within 1 hour, within 45, within 30 minutes, within 20, within 15 minutes, within 10 minutes, or within 5 minutes of each other. In other embodiments, "co-administer" refers to administration at the same time, either as part of a single formulation or as multiple formulations that are administered by the same or different routes. When the inhibitor and the pharmaceutically active agent are administered in different pharmaceutical compositions or at different times, routes of administration can be same or different.

Exemplary pharmaceutically active compound include, but are not limited to, those found in Harrison's Principles of Internal Medicine, 13th Edition, Eds. T. R. Harrison et al. McGraw-Hill N.Y., NY; Physicians' Desk Reference, 50th Edition, 1997, Oradell N.J., Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's The Pharmacological Basis of Therapeutics; and current edition of The Merck Index, the complete contents of all of which are incorporated herein by reference.

In some embodiments, pharmaceutically active agent can include those agents known in the art for treating cardiovascular calcification, such as vitamin D sterols and/or RENAGEL®. Vitamin D sterols can include calcitriol, alfacalcidol, doxercalciferol, maxacalcitol or paricalcitol.

In some embodiments, pharmaceutically active agent can include calcimimetics, vitamins and their analogs, antibiotics, lanthanum carbonate, lipid-lowering agents, such as a statin (e.g. LIPITOR®), other modulators of lipid profile (e.g., HDL-raising drugs), anti-hypertensives, anti-inflammatory agents (steroidal and non-steroidal), inhibitors of pro-inflammatory cytokine (ENBRELOR®, KINERET®), and cardiovascular agents.

In some embodiments, pharmaceutically active agent includes those agents known in the art for treatment of inflammation or inflammation-associated disorders.

In some embodiments, pharmaceutically active agent can by a bisphosphonate (Alendronate, Risendronate, Ibandronate, Zoledronic acid).

In some embodiments, pharmaceutically active agent can by a hormone-related agent.

In some embodiments, the pharmaceutically active agent is an anti-inflammatory agent. Exemplary anti-inflammatory agents include, but are not limited to, non-steroidal anti-inflammatory drugs (NSAIDs—such as aspirin, ibuprofen, or naproxen, coricosteroids (such as presnisone), anti-malarial medication (such as hydrochloroquine), methotrexrate, sulfasalazine, leflunomide, anti-TNF medications, cyclophosphamise, mycophenolate, and inhibitors of pro-inflammatory signaling pathways.

In some embodiments, the pharmaceutically active agent is an immune response modulator. As used herein, the term "immune response modulator" refers to compound (e.g., a small-molecule, antibody, peptide, nucleic acid, or gene therapy reagent) that inhibits autoimmune response in a subject. Without wishing to be bound by theory, an immune response modulator inhibits the autoimmune response by inhibiting the activity, activation, or expression of inflammatory cytokines (e.g., IL-12, IL-23 or IL-27), or STAT-4. Exemplary immune response modulators include, but are not limited to, members of the group consisting of Lisofylline (LSF) and the LSF analogs and derivatives described in U.S. Pat. No. 6,774,130, contents of which are herein incorporated by reference in their entirety.

In some embodiments, the pharmaceutically active agent is an antibiotic agent. The term "antibiotic" is used herein to describe a compound or composition which decreases the viability of a microorganism, or which inhibits the growth or reproduction of a microorganism. As used in this disclosure, an antibiotic is further intended to include an antimicrobial, bacteriostatic, or bactericidal agent. Exemplary antibiotics include, but are not limited to, penicillin, cephalosporins, penems, carbapenems, monobactams, aminoglycosides, sulfonamides, macrolides, tetracyclins, lincosides, quinolones, chloramphenicol, vancomycin, metronidazole, rifampin, isoniazid, spectinomycin, trimethoprim, sulfamethoxazole, and the like.

For administration to a subject, the inhibitor can be formulated in pharmaceutically acceptable compositions which comprise the inhibitor formulated together with one or more pharmaceutically acceptable carriers (additives) and/or diluents. The inhibitors can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; (9) nasally; or (10) local administration (e.g., drug eluting stent, pluronic gel). Additionally, the inhibitors can be implanted into a patient or injected using a drug delivery composition. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (24) C2-C12 alcohols, such as ethanol; (26) lipid nanoparticles; and (27) other non-toxic compatible substances employed in pharmaceutical formulations. The carrier or excipient can include time delay material, such as glyceryl monostearate or glyceryl distearate alone or with a wax, or other materials well known in the art. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Pharmaceutically-acceptable antioxidants include, but are not limited to, (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lectithin, propyl gallate, alpha-tocopherol, and the like; and (3) metal chelating agents, such as citric acid, ethylenediamine tetraacetic acid (EDTA), sorbitol, tartaric acid, phosphoric acids, and the like.

The preparation of pharmaceutical compositions is well known in the art and has been described in many articles and textbooks, see e.g., Remington's Pharmaceutical Sciences, Gennaro A. R. ed., Mack Publishing Co., Easton, Pa., 1990, content of which of which is incorporated herein by reference in its entirety.

The pharmaceutical compositions can be made up in a solid form (including granules, powders or suppositories) or in a liquid form (e.g., solutions, suspensions, or emulsions). The pharmaceutical compositions can be subjected to conventional pharmaceutical operations such as sterilization and/or can contain conventional adjuvants, such as preservatives, stabilizers, wetting agents, emulsifiers, buffers etc.

Solid dosage forms for oral administration can include capsules, tablets, pills, powders, and granules. In such solid dosage forms, the active compound can be admixed with at least one inert diluent such as sucrose, lactose, or starch. Such dosage forms can also comprise, as in normal practice, additional substances other than inert diluents, e.g., lubricating agents such as magnesium stearate. In the case of capsules, tablets, and pills, the dosage forms can also comprise buffering agents. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting, sweetening, flavoring, and perfuming agents.

For purposes of parenteral administration, solutions in sesame or peanut oil or in aqueous propylene glycol can be employed, as well as sterile aqueous solutions of the corresponding water-soluble salts. Such aqueous solutions can be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art methods of preparing various pharmaceutical compositions with a certain amount of active ingredient are known, or will be apparent in light of this disclosure, to those skilled in this art.

The inhibitors can also be administered in controlled release formulations such as a slow release or a fast release formulation. Such controlled release formulations of the combination of this invention can be prepared using methods well known to those skilled in the art. The method of administration will be determined by the attendant physician or other person skilled in the art after an evaluation of the subject's conditions and requirements.

The amount of inhibitor that can be combined with a carrier material to produce a single dosage form will generally be that amount of the inhibitor that produces a therapeutic effect. Generally, out of one hundred percent, this amount will range from about 0.01% to 99% of inhibitor. In some embodiment, amount of the inhibitor in the composition can be selected from the range from about 0.1% to about 99% (w/w), from about 1% to about 90% (w/w), from about 2% to about 80% (w/w), from about 5% to about 75% (w/w), from about 5% to about 50% (w/w), from about 10% (w/w) to about 60% (w/w), from about 0.01% to about 95% (w/v), from about 0.1% to about 90% (w/w), from about 1% to about 85% (w/w), from about 10% to about 50% (w/w), from about 1% to about 99% (w/w), from about 0.05% to about 99% (w/w), from about 0.1% to about 90% (w/w), from about 0.5% to about 85% (w/w), or from about 5% to about 80% (w/w) of the total composition.

In some embodiments, the agent or composition administered to a subject comprises a therapeutically effective amount of the sortilin dimerization inhibitor for the treatment of an extracellular vesicle-associated disease (e.g. cardiovascular calcification).

As used herein, the term "therapeutically effective amount" means an amount of the therapeutic agent which is effective to provide a desired outcome. Determination of a therapeutically effective amount is well within the capability of those skilled in the art. Generally, a therapeutically effective amount can vary with the subject's history, age, condition, sex, as well as the severity and type of the medical condition in the subject, and administration of other agents that inhibit pathological processes in neurodegenerative disorders.

Furthermore, therapeutically effective amounts will vary, as recognized by those skilled in the art, depending on the specific disease treated, the route of administration, the excipient selected, and the possibility of combination therapy. In some embodiments, the therapeutically effective amount can be in a range between the ED50 and LD50 (a dose of a therapeutic agent at which about 50% of subjects taking it are killed). In some embodiments, the therapeutically effective amount can be in a range between the ED50 (a dose of a therapeutic agent at which a therapeutic effect is detected in at least about 50% of subjects taking it) and the TD50 (a dose at which toxicity occurs at about 50% of the cases). Guidance regarding the efficacy and dosage which will deliver a therapeutically effective amount of a compound can be obtained from animal models of condition to be treated.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices are preferred.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized.

The therapeutically effective dose can be estimated initially from cell culture assays. A dose can be formulated in animal models to achieve a circulating plasma concentration range that includes the IC50 (i.e., the concentration of the therapeutic which achieves a half-maximal inhibition of symptoms) as determined in cell culture. Levels in plasma can be measured, for example, by high performance liquid chromatography. The effects of any particular dosage can be monitored by a suitable bioassay. Examples of suitable bioassays include DNA replication assays, transcription based assays, and immunological assays.

The dosage can be determined by a physician and adjusted, as necessary, to suit observed effects of the treatment. Generally, the complex inhibitors are administered so that the inhibitor is given at a dose from 1 μg/kg to 150 mg/kg, 1 μg/kg to 100 mg/kg, 1 μg/kg to 50 mg/kg, 1 μg/kg to 20 mg/kg, 1 μg/kg to 10 mg/kg, 1 μg/kg to 1 mg/kg, 100 μg/kg to 100 mg/kg, 100 μg/kg to 50 mg/kg, 100 μg/kg to 20 mg/kg, 100 μg/kg to 10 mg/kg, 100 μg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like. For protein based inhibitors (such as antibodies) one preferred dosage is 0.1 mg/kg to 100 mg/kg of body weight (generally 10 mg/kg to 20 mg/kg).

The dosage regimen for treating a disease condition, e.g., an EV-associated disease with the combination therapy disclosed herein can be selected in accordance with a variety of factors, including the type, age, weight, sex and medical condition of the patient, the severity of the disease, the route of administration, and the particular compound employed, and thus can vary widely.

In another aspect, provided herein is a method for identifying a test agent that modulates dimerization of sortilin. Generally, the method comprises: (i) contacting a cell with a test agent, wherein the cell expresses a first sortilin polypeptide comprising a first label, and a second sortilin polypeptide comprising a second label; (ii) detecting a distance or contact level between the first and second sortilin polypeptide expressed in the cell, wherein a change in distance or contact level relative to a control or reference level indicates the agent modulates dimerization of sortilin.

In some embodiments, an increase in the distance or contact level relative to a control or reference level indicates the compound inhibits dimerization of sortilin. In some other embodiments, a decrease in distance or contact level relative to a control or reference level indicates the compound increases dimerization of sortilin. In some embodiments, the control or reference level is the distance or contact level in a cell that has not been contacted with the test agent.

Any method available to one of skill in the art for determining distance or contact between two components can be used.

For example, the first and/or the second label can be a detectable label. As used herein, the term "detectable label" refers to a composition capable of producing a detectable signal indicative of the presence of a target. Detectable labels include any composition detectable by spectroscopic, photochemical, biochemical, immunochemical, electrical, optical or chemical means. Suitable labels include fluorescent molecules, radioisotopes, nucleotide chromophores, enzymes, substrates, chemiluminescent moieties, bioluminescent moieties, and the like. As such, a label is any composition detectable by spectroscopic, photochemical, biochemical, immunochemical, electrical, optical or chemical means needed for the methods and devices provided herein.

A wide variety of fluorescent reporter dyes are known in the art. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound.

Exemplary fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein (pH 10); 5-Carboxytetramethylrhodamine (5-TAMRA); 5-FAM (5-Carboxyfluorescein); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); Alexa Fluor350™; Alexa Fluor430™; Alexa Fluor 488™; Alexa Fluor 532™; Alexa Fluor546™; Alexa Fluor568™; Alexa Fluor594™; Alexa Fluor 633™; Alexa Fluor647™; Alexa Fluor660™; Alexa Fluor680™; Alizarin Complexon; Alizarin Red; Allophycocyanin (APC); AMC, AMCA-S; AMCA (Aminomethylcoumarin); AMCA-X; Aminoactinomycin D; Aminocoumarin; Anilin Blue; Anthrocyl stearate; APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); BG-647; Bimane; Bisbenzamide; Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Green-1 Ca2+Dye; Calcium Green-2 Ca2+; Calcium Green-5N Ca2+; Calcium Green-C18 Ca2+; Calcium Orange; Calcofluor White; Carboxy-X-rhodamine (5-ROX); Cascade Blue™; Cascade Yellow; Catecholamine; CFDA; CFP—Cyan Fluorescent Protein; Chlorophyll; Chromomycin A; Chromomycin A; CMFDA; Coelenterazine; Coelenterazine cp; Coelenterazine f; Coelenterazine fcp; Coelenterazine h; Coelenterazine hcp; Coelenterazine ip; Coelenterazine 0; Coumarin Phalloidin; CPM Methylcoumarin; CTC; Cy2™; Cy3.1 8; Cy3.5™; Cy3™; Cy5.1 8; Cy5.5™; CyS™; Cy7™; Cyan GFP; cyclic AMP Fluorosensor (FiCRhR); d2; Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di-16-ASP); DIDS; Dihydorhodamine 123 (DHR); DiO (DiOC18(3)); DiR; DiR (DiIC18(7)); Dopamine; DsRed; DTAF; DY-630-NHS; DY-635-NHS; EBFP; ECFP; EGFP; ELF 97; Eosin; Erythrosin; Erythrosin ITC; Ethidium homodimer-1 (EthD-1); Euchrysin; Europium (III) chloride; Europium; EYFP; Fast Blue; FDA; Feulgen (Pararosaniline); FITC; FL-645; Flazo Orange; Fluo-3; Fluo-4; Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura-2, high calcium; Fura-2, low calcium; Genacryl Brilliant Red B; Genacryl Brilliant Yellow 10GF; Genacryl Pink 3G; Genacryl Yellow SGF; GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indodicarbocyanine (DiD); Indotricarbocyanine (DiR); Intrawhite Cf; JC-1; JO-JO-1; JO-PRO-1; LaserPro; Laurodan; LDS 751; Leucophor PAF; Leucophor SF; Leucophor WS; Lissamine Rhodamine; Lissamine Rhodamine B; LOLO-1; LO-PRO-1; Lucifer Yellow; Mag Green; Magdala Red (Phloxin B); Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Briliant Iavin E8G; Oregon Green™; Oregon Green 488-X; Oregon Green™ 488; Oregon Green™ 500; Oregon Green™ 514; Pacific Blue; Pararosaniline (Feulgen); PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26; PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B 540; Rhodamine B 200; Rhodamine B extra; Rhodamine BB; Rhodamine BG; Rhodamine Green; Rhodamine Phallicidine; Rhodamine Phalloidine;

Rhodamine Red; Rhodamine WT; Rose Bengal; R-phycoerythrin (PE); red shifted GFP (rsGFP, S65T); S65A; S65C; S65L; S65T; Sapphire GFP; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SPQ (6-methoxy-N-(3-sulfopropyl)-quinolinium); Stilbene; Sulphorhodamine B can C; Sulphorhodamine G Extra; Tetracycline; Tetramethylrhodamine; Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC (TetramethylRodamineIsoThioCyanate); True Blue; TruRed; Ultralite; Uranine B; Uvitex SFC; wt GFP; WW 781; XL665; X-Rhodamine; XRITC; Xylene Orange; Y66F; Y66H; Y66W; Yellow GFP; YFP; YO-PRO-1; YO-PRO-3; YOYO-1; and YOYO-3. Many suitable forms of these fluorescent compounds are available and can be used.

Other exemplary detectable labels include luminescent and bioluminescent markers (e.g., biotin, luciferase (e.g., bacterial, firefly, click beetle and the like), luciferin, and aequorin), radiolabels (e.g., 3H, 125I, 35S, 14C, or 32P), enzymes (e.g., galactosidases, glucorinidases, phosphatases (e.g., alkaline phosphatase), peroxidases (e.g., horseradish peroxidase), and cholinesterases), and calorimetric labels such as colloidal gold or colored glass or plastic (e.g., polystyrene, polypropylene, and latex) beads. Patents teaching the use of such labels include U.S. Pat. Nos. 3,817,837, 3,850,752, 3,939,350, 3,996,345, 4,277,437, 4,275,149, and 4,366,241, each of which is incorporated herein by reference.

Means of detecting such labels are well known to those of skill in the art. Thus, for example, radiolabels can be detected using photographic film or scintillation counters, fluorescent markers can be detected using a photo-detector to detect emitted light. Enzymatic labels are typically detected by providing the enzyme with an enzyme substrate and detecting the reaction product produced by the action of the enzyme on the enzyme substrate, and calorimetric labels can be detected by visualizing the colored label.

In some embodiments, the label is a heterologous protein. In some embodiments, the heterologous protein is a tag, such as a fluorescent protein. In some embodiments, the donor or acceptor is a soluble sortilin protein, a sortilin-derived propeptide, or sortilin-derived nucleic acid as provided herein that is conjugated to a fluorescent or protein tag. In some embodiments, the tag is conjugated to the C-terminus of the protein. In some embodiments, the tag is conjugated to the N-terminus of the protein. In some embodiments, the sortilin-derived propeptide is further conjugated to a magnetoresponsive bead for purification.

Such proteins can further facilitate tracking and/or visualization of the sortilin protein, dimers, and multimers. Additional non-limiting examples of heterologous protein tags that can be used in sortilin trafficking assays (e.g. FRET) include Histamine (HIS), sequence motif DYKDDDDK (where D=aspartic acid, Y=tyrosine, and K=lysine) or a FLAG tag, β-galactosidase, human influenza hemagglutinin (HA), OLLAS, c-myc, paramyxovirus of simian virus 5 epitope (V5) or any other protein epitope tag known in the art.

In some embodiments, sortilin dimerization can be detected or measured by analyzing the contacted the cell using Fluorescence Resonance Energy Transfer (FRET), e.g., Time-Resolved Fluorescence Resonance Energy Transfer (TR-FRET) or homogenous time resolved-fluorescence resonance energy transfer (HTRF). See, for example, Maurel et al. *Anal. Biochem* (2004), 253-262.

Fluorescence resonance energy transfer or Förster resonance energy transfer (FRET) is known in the art as a method to detect the proximity of two proteins on a cell surface (Maurel et al. *Anal. Biochem* (2004), 253-262) using a donor and acceptor fluorophore. The donor protein or nucleic acid can be labeled with a different fluorophore, protein tags, or epitope than the acceptor protein or nucleic acid. Thus, as as the donor protein or nucleic acid contacts the acceptor second protein or nucleic acid, the change in fluorescence or a proteolytic cleavage can occur. This allows for detection of changes in the signal from the fluorophores used in this assay.

For example, one of the first or second label FRET donot and the other is a FRET acceptor, and the FRET signal is measured. Alternatively, a first ligand that is capable of binding with the first label and a second ligand that is capable of binding with the second label can be used. One of the first or second ligands can comprise a FRET dononr and the other can comprise a FRET acceptor. The contacted cell is further contacted with the ligands and the FRET signal is measured.

FRET signal is measured in the presence (e.g., in a cell contacted with the test agent) and absence (e.g., in a cell not contacted with the test agent) of the test agent. A change in FRET signal relative to a control or reference level indicating the agent modulates dimerization of sortilin. For example, an increase in FRET signal relative to a control or reference level indicates the compound inhibits dimerization of sortilin. Alternatively, a decrease in FRET signal relative to a control or reference level indicates the compound increases dimerization of sortilin. In some embodiments, the control or reference level is a FRET signal in a cell expressing both the first sortilin polypeptide and the second sortilin polypeptide. In some other embodiments, the control or reference level is a FRET signal in a cell expressing either the first sortilin polypeptide or the second sortilin polypeptide.

Any molecule capable of biding with the label can be used as the ligand. For example, the ligand can be an antibody, antigen binding fragment of an antibody, an aptamer, one part of a binding pair (e.g., biotin and avidin, or biotin and streptavidin). In some embodiments, the first and/or the second ligand is an antibody.

The FRET signal can be determined by a plate reader, confocal microscope, or any other detection method known in the art. For example, the FRET signal can be calculated as the ratio of counts per second (e.g. 665:620)×10,000, and % change of the FRET signal by tagged sortilin (e.g. 6×His-sortilin) expression. The signal can also be compared with an appropriate control tag. Sortlin can be considered to be dimerized when the FRET signal is 80% or more, 90% or more, 100% or more, 110% or more, 115% or more, 120% or more, 130% or more, 140% or more, 150% or more, 160% or more 170% or more, 180% or more, 190% or more, 200% or more and beyond. It is contemplated that these values can vary depending on the conditions of the assays such as the ratio of counts per second, the protein tag, or the control used.

It is contemplated that additional assays can be used to identify dimerization of sortilin which include but are not limited to enzyme-linked immunosorbent assay (ELISA), Western Blot, immunohistochemistry, protein-conjugated quantum dots, proteomics, mass spectrometry, Edman degradation, Matrix Assisted Laser Desorption/Ionization (MALDI), scanning electron microscopy, super resolution microscopy, transmission electron microscopy, or any other assay that identifies proteins, protein structure, composition, interactions, or localization known in the art.

As used herein, the term "test compound" refers to compounds and/or compositions that are to be screened for their ability to inhibit dimerization of sortilin. Test compounds may include a wide variety of different compounds, including chemical compounds, mixtures of chemical compounds, e.g., small organic or inorganic molecules; saccharines; oligosaccharides; polysaccharides; biological macromolecules, e.g., peptides, proteins, and peptide analogs and derivatives; peptidomimetics; nucleic acids; nucleic acid analogs and derivatives; an extract made from biological materials such as bacteria, plants, fungi, or animal cells; animal tissues; naturally occurring or synthetic compositions; and any combinations thereof. In some embodiments, the test compound is a small molecule.

The number of possible test compounds runs into millions. Methods for developing small molecule, polymeric and genome based libraries are described, for example, in Ding, et al. J Am. Chem. Soc. 124: 1594-1596 (2002) and Lynn, et al., J. Am. Chem. Soc. 123: 8155-8156 (2001). Commercially available compound libraries can be obtained from, e.g., ArQule, Pharmacopia, graffinity, Panvera, Vitas-M Lab, Biomol International and Oxford. These libraries can be screened using the screening devices and methods provided herein. Chemical compound libraries such as those from NIH Roadmap, Molecular Libraries Screening Centers Network (MLSCN) can also be used.

Comprehensive list of compound libraries can be found on the web, for example, at www.broad.harvard.edu/chembio/platform/screening/compound_libraries/index.htm.

A chemical library or compound library is a collection of stored chemicals usually used ultimately in high-throughput screening or industrial manufacture. The chemical library can consist in simple terms of a series of stored chemicals. Each chemical has associated information stored in some kind of database with information such as the chemical structure, purity, quantity, and physiochemical characteristics of the compound.

Depending upon the particular embodiment being practiced, the test compounds may be provided free in solution, or may be attached to a carrier, or a solid support, e.g., beads. A number of suitable solid supports may be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods provided herein, test compounds may be screened individually, or in groups. Group screening is particularly useful where hit rates for effective test compounds are expected to be low such that one would not expect more than one positive result for a given group.

Generally, compounds can be tested at any concentration that can inhibit and/or decrease dimerization of sortilin. In some embodiments, compounds are tested at a concentration in the range of from about 0.1 nM to about 1000 mM. Preferably the compound is tested in the range of from about 0.1 μM to about 10 μM.

In some embodiments, screening assay further comprises selecting the compound that inhibits or reduces sortilin dimerization. The test compound can inhibit or reduce sortilin dimerization by at least 10%, 20%, 30%, 40%, 50%, 50%, 70%, 80%, 90%, 95% or more relative to a control.

In some embodiments, the screening method is a high-throughput screening. High-throughput screening (HTS) is a method for scientific experimentation that uses robotics, data processing and control software, liquid handling devices, and sensitive detectors. High-Throughput Screening or HTS allows a researcher to quickly conduct millions of biochemical, genetic or pharmacological tests. High-Throughput Screening are well known to one skilled in the art, for example, those described in U.S. Pat. Nos. 5,976,813; 6,472,144; 6,692,856; 6,824,982; and 7,091,048, and contents of each of which is herein incorporated by reference in its entirety.

HTS uses automation to run a screen of an assay against a library of candidate compounds. An assay is a test for specific activity: usually inhibition or stimulation of a biochemical or biological mechanism. Typical HTS screening libraries or "decks" can contain from 100,000 to more than 2,000,000 compounds. The key labware or testing vessel of HTS is the microtiter plate: a small container, usually disposable and made of plastic, that features a grid of small, open divots called wells. Modern microplates for HTS generally have either 384, 1536, or 3456 wells. These are all multiples of 96, reflecting the original 96 well microplate with 8×12 9 mm spaced wells.

To prepare for an assay, the researcher fills each well of the plate with the appropriate reagents that he or she wishes to conduct the experiment with. After some incubation time has passed to allow the reagent to absorb, bind to, or otherwise react (or fail to react) with the compounds in the wells, measurements are taken across all the plate's wells, either manually or by a machine. Manual measurements are often necessary when the researcher is using microscopy to (for example) seek changes that a computer could not easily determine by itself. Otherwise, a specialized automated analysis machine can run a number of experiments on the wells such as colorimetric measurements, radioactivity counting, etc. In this case, the machine outputs the result of each experiment as a grid of numeric values, with each number mapping to the value obtained from a single well. A high-capacity analysis machine can measure dozens of plates in the space of a few minutes like this, generating thousands of experimental data points very quickly.

In another aspect, the invention provides a compound selected by the screening assay provided herein. It is to be understood that analogs, derivatives, and isomers of the compounds selected by the screening assays provided herein are also claimed herein.

In still another aspect, provided herein is a method for preparing dimeric soluble sortilin. Generally, the method comprises expressing a sortilin polypeptide comprising a first label in an extracellular domain from a cell and purifying the expressed sortilin polypeptide using affinity purification. The affinity purification can be based on the first label, for example, using a ligand capable of binding with the first label.

In some embodiments, the sortilin polypeptide comprises a complete or fragment of the amino acid sequence SEQ ID NO:1 or SEQ ID NO: 2. In some embodiments, the sortilin protein is expressed by an expression vector.

Expression vectors can be constructed from, for example, pcDNA3.1 (+) vectors such as those commercially available from Thermo Fisher Scientific, Inc (Waltham, Mass., USA). The term "vector", as used herein, refers to a nucleic acid construct designed for delivery to a host cell or for transfer between different host cells. As used herein, a vector can be viral or non-viral. A vector can include, but is not limited to, a cloning vector, an expression vector, a plasmid, phage, transposon, cosmid, artificial chromosome, virus, virion, etc.

In some embodiments, the vector is integrative or non-integrative. In some embodiments, the non-integrative vector is an episomal vector, an EBNA1 vector, a minicircle vector, a non-integrative adenovirus, a non-integrative RNA, or a Sendai virus. In some embodiments, the vector is an episomal vector. In some embodiments, the vector is a lentiviral vector.

As used herein, the term "expression vector" refers to a vector that directs expression of an RNA or polypeptide (e.g., a sortilin inhibitor) from nucleic acid sequences contained therein linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

Integrating vectors have their delivered RNA/DNA permanently incorporated into the host cell chromosomes. Non-integrating vectors remain episomal which means the nucleic acid contained therein is never integrated into the host cell chromosomes. Examples of integrating vectors include retroviral vectors, lentiviral vectors, hybrid adenoviral vectors, and herpes simplex viral vector.

One example of a non-integrative vector is a non-integrative viral vector. Non-integrative viral vectors eliminate the risks posed by integrative retroviruses, as they do not incorporate their genome into the host DNA. One example is the Epstein Barr oriP/Nuclear Antigen-1 ("EBNA1") vector, which is capable of limited self-replication and known to function in mammalian cells. As containing two elements from Epstein-Barr virus, oriP and EBNA1, binding of the EBNA1 protein to the virus replicon region oriP maintains a relatively long-term episomal presence of plasmids in mammalian cells. This particular feature of the oriP/EBNA1 vector makes it ideal for generation of integration-free iPSCs. Another non-integrative viral vector is adenoviral vector and the adeno-associated viral (AAV) vector.

Another non-integrative viral vector is RNA Sendai viral vector, which can produce protein without entering the nucleus of an infected cell. The F-deficient Sendai virus vector remains in the cytoplasm of infected cells for a few passages, but is diluted out quickly and completely lost after several passages (e.g., 10 passages).

Another example of a non-integrative vector is a minicircle vector. Minicircle vectors are circularized vectors in which the plasmid backbone has been released leaving only the eukaryotic promoter and cDNA(s) that are to be expressed.

As used herein, the term "viral vector" refers to a nucleic acid vector construct that includes at least one element of viral origin and has the capacity to be packaged into a viral vector particle. The viral vector can contain a nucleic acid encoding a polypeptide as provided herein in place of non-essential viral genes. The vector and/or particle may be utilized for the purpose of transferring nucleic acids into cells either in vitro or in vivo. Numerous forms of viral vectors are known in the art.

Constructs of human sortilin (NM_002959.5) can be generated by inserting a protein tag as provided herein (e.g. FLAG (DYKDDDDK) or 6×His (HHHHHH) tag) into amino acids (e.g. 3 amino acids, S73A1330) behind the furin cleavage site (e.g. R74WRR77) using site-mutagenesis. Methods of cloning and expressing engineered proteins are known in the art. Other constructs of sortilin can be generated, such as sortilin CD43-TMD, by using an overlapping PCR strategy with a CD43 expression vector or an expression vector of sortilin with 3×FLAG at C-terminus.

An EV-deprived culture medium of cells with expressed sortilin (with the protein tag as provided herein) can be subjected to an affinity gel or solid support for purification, e.g., ANTI-FLAG® M2 from Sigma Aldrich (St. Louis, Mo.). Soluble sortilin with a protein tag can be eluted with a peptide. Purified soluble sortilin can then be dialyzed in phosphate buffer solution. Sortilin expression can be determine by Western Blot analysis or any other protein expression assay known in the art. Similarly, protein interactions can be determined by immunoprecipitation of sortilin with additional epitope-tagged proteins.

As provided herein, a "solid support" is any structure that can make contact with the target sortilin, dimeric sortilin, multimeric sortilin, sortilin-derived polypeptides, or epitope polypeptides conjugated to sortilin. The form of the solid support can comprise but are not limited to a scaffold, cartridge, column, filter, resin, or matrix, or bead. Non-limiting classes of materials that the solid support comprises include polymer, metal, ceramic, gels, paper, or glass.

In some embodiments, sortilin is bound directly or indirectly to the solid support. In some embodiments, the solid support comprises materials that include but are not limited to a polymer, metal, ceramic, gels, paper, or glass. The materials of the solid support can further comprise polystyrene, agarose, gelatin, alginate, iron oxide, stainless steel, gold nanobeads or particles, copper, silver chloride, polycarbonate, polydimethylsiloxane, polyethylene, acrylonitrile butadiene styrene, cyclo-olefin polymers, or cyclo-olefin copolymers, Sepharose™ resin.

In some embodiments, the solid support further comprises an element that is magnetoresponsive. In some embodiments, the magnetoresponsive element comprises magnetite, iron (III) oxide, samarium-cobalt, terfenol-D, or any other magnetic element described in the art.

The engineered sortilin protein can further be crosslinked to the membrane of a vesicle or cell to determine localization of the sortilin dimers. Chemical cross-linking can be carried out by incubating cells transiently overexpressing tagged-sortilin with bis (sulfosuccinimidyl) suberate (BS3), water-soluble, non-cleavable cross-linker at room temperature. The cells can be centrifuged at (e.g. at 1,000 rpm for 5 minutes) to remove the buffer including BS3, and washed with phosphate buffer solution. Then the cell can be lysed and prepared for Western blotting or immunoprecipitation as provided herein.

Some Selected Definitions

Unless defined otherwise, all technical and scientific terms used herein have the same meaning as those commonly understood to one of ordinary skill in the art to which this invention pertains. Although any known methods, devices, and materials can be used in the practice or testing of the invention, the methods, devices, and materials in this regard are provided herein.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments of the aspects provided herein, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as provided herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages can mean±1%.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

As used herein, a "reference level" refers to a normal, otherwise unaffected cell population or tissue (e.g., a biological sample obtained from a healthy subject, or a biological sample obtained from the subject at a prior time point, e.g., a biological sample obtained from a patient prior to being diagnosed with an EV-associated disease, or a biological sample that has not been contacted with an agent or composition disclosed herein).

As used herein, an "appropriate control" or "control" refers to an untreated, otherwise identical cell or population (e.g., a biological sample that was not contacted by an agent or composition provided herein, or not contacted in the same manner, e.g., for a different duration, as compared to a non-control cell).

The singular terms "a," "an," and "the" include plural referents unless context clearly indicates otherwise. Similarly, the word "or" is intended to include "and" unless the context clearly indicates otherwise. Thus for example, references to "the method" includes one or more methods, and/or steps of the type provided herein and/or which will become apparent to those persons skilled in the art upon reading this disclosure and so forth.

Although methods and materials similar or equivalent to those provided herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

Some embodiments of the various aspect described herein can be described as in the following paragraphs:

1. A method for inhibiting or reducing trafficking of sortilin to an extracellular vesicle (EV) from a cell, the method comprising inhibiting covalent intermolecular dimerization of sortilin in the cell.
2. The method of paragraph 1, wherein said inhibiting comprises inhibiting formation of an intermolecular disulfide formation at Cys783 of SEQ ID NO: 1.
3. The method of paragraph 1 or 2, wherein said inhibiting comprises administering a peptide to the cell.
4. The method of paragraph 3, wherein said peptide is a sortilin-derived propeptide comprising an amino acid sequence of SEQ ID NO: 2.
5. The method of paragraph 3 or 4, wherein the peptide comprises at least one modification.

6. The method of any one of paragraphs 3-5, wherein the peptide is amidated, acetylated, cyclized, phosphorylated, glycosylated, nitrosylated, methylated, lipidated, or PEGylated.
7. The method of any one of paragraphs 3-6, wherein the peptide comprises at least one D amino acid, beta amino acid or modified peptide linkage.
8. The method of any one of paragraphs 3-7, wherein the peptide comprises at least one substituted amino acid.
9. The method of any one of paragraphs 1-8, wherein the cell is a leukocyte, lymphocyte, macrophage, natural killer cell, dendritic cell, T cell, or B cell.
10. The method of any one of paragraphs 1-9, wherein said inhibiting is in in vitro or ex vivo.
11. The method of any one of paragraphs 1-9, wherein said inhibiting is in vivo.
12. The method of paragraph 11, wherein said inhibiting is in a mammal.
13. The method of paragraph 11 or 12, wherein said inhibiting is in a subject having or suspected of having an extracellular vesicle associated disease (EV-associated disease).
14. The method of paragraph 13, wherein the EV-associated disease is selected from the group consisting of: calcific aortic valve disease, diabetes, systemic lupus erythematosus, ulcerative colitis, pulmonary fibrosis, nan-alcoholic fatty liver disease, osteoporosis, Alzheimer's disease, scleroderma, atherosclerosis, myocardial infarction, hypercholesterolemia, cancer, rheumatoid arthritis, and obesity.
15. The method of paragraph 14, where diabetes is type 1 diabetes, type 2 diabetes, or maturity onset diabetes in the young.
16. The method of paragraph 14, wherein cancer is lung cancer or pancreatic cancer.
17. A method of treating an extracellular vesicle associated disease in subject, comprising inhibiting inhibiting covalent intermolecular dimerization of sortilin in a cell in a subject in need thereof.
18. The method of paragraph 17, wherein said inhibiting comprises inhibiting formation of an intermolecular disulfide formation at Cys783 of SEQ ID NO: 1.
19. The method of paragraph 17 or 18, wherein said inhibiting comprises administering a peptide to the subject in need thereof.
20. The method of paragraph 19, wherein said peptide is a sortilin-derived propeptide comprising an amino acid sequence of SEQ ID NO: 2.
21. The method of paragraph 19 or 20, wherein the peptide comprises at least one modification.
22. The method of any one of paragraphs 19-21, wherein the peptide is amidated, acetylated, cyclized, phosphorylated, glycosylated, nitrosylated, methylated, lipidated, or PEGylated.
23. The method of any one of paragraphs 19-22, wherein the peptide comprises at least one D amino acid, beta amino acid or modified peptide linkage.
24. The method of any one of paragraphs 19-23, wherein the peptide comprises at least one substituted amino acid.
25. The method of any one of paragraphs 17-24, wherein the cell is a leukocyte, lymphocyte, macrophage, natural killer cell, dendritic cell, T cell, or B cell.
26. The method of any one of paragraphs 17-25, wherein said EV-associated disease is selected from the group consisting of calcific aortic valve disease, diabetes, systemic lupus erythematosus, ulcerative colitis, pulmonary fibrosis, nan-alcoholic fatty liver disease, osteoporosis, Alzheimer's disease, scleroderma, atherosclerosis, myocardial infarction, hypercholesterolemia, cancer, rheumatoid arthritis, and obesity.
27. The method of paragraph 26, where diabetes is type 1 diabetes, type 2 diabetes, or maturity onset diabetes in the young.
28. The method of paragraph 26, wherein cancer is lung cancer or pancreatic cancer.
29. A method for identifying a test agent that modulates dimerization of sortilin, the method comprising:
(i) contacting a cell with a test agent, wherein the cell expresses a first sortilin polypeptide comprising a first label, and a second sortilin polypeptide comprising a second label;
(ii) detecting a contact level between the first and second sortilin polypeptide expressed in the cell,
wherein a change in contact level relative to a control or reference level indicates the agent modulates dimerization of sortilin.
30. The method of paragraph 29, wherein said detecting comprises analyzing the cell contacted in step (i) using Time-Resolved Fluorescence Resonance Energy Transfer (TR-FRET), and wherein a change in FRET signal relative to a control or reference level indicates the agent modulates dimerization of sortilin.
31. The method of paragraph 29 or 30, wherein an increase in FRET signal relative to a control or reference level indicates the compound inhibits dimerization of sortilin.
32. The method of paragraph 29 or 30, wherein a decrease in FRET signal relative to a control or reference level indicates the compound increases dimerization of sortilin.
33. The method of any one of paragraphs 30-32, wherein the control or reference level is a FRET signal in a cell expressing either the first sortilin polypeptide or the second sortilin polypeptide.
34. The method of any one of paragraphs 29-33, wherein said detecting comprises contacting the cell with a first ligand and a second ligand, wherein the first ligand is capable of binding with the first label and is conjugated with a with a Fluorescence Resonance Energy Transfer (FRET) donor, and wherein the second ligand is capable of binding with the second label and is conjugated with a FRET acceptor.
35. The method of paragraph 34, wherein the first or second ligand is an antibody.
36. The method of any one of paragraphs 29-35, wherein the agent inhibits dimerization of sortilin.
37. The method of any one of paragraphs 29-35, wherein the agent increases dimerization of sortilin.
38. A method for preparing dimeric soluble sortilin, the method comprising:
(i) expressing a sortilin polypeptide comprising a first label in an extracellular domain from a cell;
(ii) purifying the expressed sortilin polypeptide via affinity purification using a ligand capable of binding with the first label.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Example 1: Dimerization of Sortilin Regulates its Trafficking to Extracellular Vesicles Extracellular vesicles (EVs) play a critical role in intercellular communication by transferring microRNAs, lipids and proteins to neighboring cells. Sortilin, a sorting receptor that directs target proteins to the secretary or endocytic compartments of cells, is found in both EVs and cells. In many human diseases, including cancer and cardiovascular diseases, sortilin expression levels are atypically increased. To elucidate the relationship between cardiovascular disease, particularly vascular calcification, and sortilin expression levels, the trafficking of sortilin in both intracellular and extracellular milieu was explored. It has been demonstrated previously that sortilin promotes vascular calcification via its trafficking of tissue-nonspecific alkaline phosphatase (TNAP) to EVs. Although recent reports have noted that sortilin is regulated by multiple post-translational modifications, the precise mechanisms of sortilin trafficking still need to be elucidated. As provided herein, sortilin forms homodimers with an intermolecular disulfide bond at Cysteine 783 ($Cys^{783}$) residue, indicating that $Cys^{783}$ can be shared via palmitoylation and an intermolecular disulfide bond, as $Cys^{783}$ can be palmitoylated. See SEQ ID NO: 1 for the amino acid sequence of sortilin.

Formation of the intermolecular disulfide bond can lead to trafficking of sortilin to EVs by preventing palmitoylation, and promotes trafficking of sortilin to the Golgi apparatus. Moreover, it was observed that sortilin-derived propeptide decreased sortilin homodimers within EVs. In conclusion, sortilin is transported to EVs via the formation of homodimers with an intermolecular disulfide bond, which is endogenously regulated by its own propeptide. Therefore, inhibiting dimerization of sortilin can act as a new therapeutic strategy for the treatment of EV-associated diseases, including vascular calcification and cancer, among others.

Intercellular communication, an essential hallmark of multicellular organisms, can be mediated through direct cell-cell contact or the transfer of secreted molecules (1). In the last two decades, a new mechanism for intercellular communication has emerged that involves intercellular transfer of extracellular vesicles (EVs), such as exosomes, which have the ability to transfer their cellular content to neighboring cells and to modify the cellular microenvironment (2) (3). The role of EVs is likely to be dictated by the vesicle cargo, which can be composed of microRNAs, RNAs, lipids and/or proteins. However, the function of some of these proteins in EVs and how they affect various diseases need to be further elucidated.

Sortilin, which is ubiquitously expressed and essential for proper function of many tissue and cell types, is a sorting receptor that directs target proteins, including growth factors, signaling receptors, and enzymes, to their destined location in the secretory or endocytic compartments of cells (4). Sortilin has conversely also emerged as a major cause of malignancies in a range of diseases, including cancer (5) (6) (7) (8), Type 2 diabetes mellitus (9), hypercholesterolemia (10) (11) (12), atherosclerosis (13) (14), and neurodegenerative disorders (15) (16) like Alzheimer's disease (17) (18). The atypical increase in intracellular trafficking by sortilin, and its subsequent lysosomal degradation (15) or secretion (10) (14), has been linked to the pathogenesis of the above diseases. In addition, recent studies have shown that sortilin can convey causative molecules of diseases to the extracellular space via EVs: 1) Previous studies showed that sortilin transports tyrosine kinases to neighboring cells through exosome transfer, promoting tumorigenesis via activation of angiogenesis (6), and 2) previous research has demonstrated that sortilin promotes vascular calcification via its trafficking and loading of tissue-nonspecific alkaline phosphatase (TNAP) into EVs (19).

Therefore, the major objective is to understand the process that facilitates the transport of sortilin into EVs. Addressing this question can help to discover new therapeutic approaches for EV-associated diseases. Although multiple post-translational modifications, including phosphorylation (19), and ubiquitination (20) (21), palmitoylation (22), can regulate functions of sortilin, the mechanisms regulating sortilin trafficking have yet to be fully understood. Since the trafficking of receptors, such as G-protein coupled-receptors (23) and type I transmembrane proteins (24) (25), can be regulated by dimerization, it is contemplated that dimerization can be a major regulator of sortilin trafficking to EVs. Provided herein is the first evidence that sortilin forms homodimers, thereby facilitating its trafficking to EVs. Specifically, the results showed that: 1) sortilin forms homodimers with an intermolecular disulfide bond at $Cys^{783}$; 2) mutation of $Cys^{783}$ abolishes transport of dimerized sortilin to EVs; and 3) inhibition of palmitoylation at $Cys^{783}$ increases sortilin homodimers. The results indicate that $Cys^{783}$ can be involved in both palmitoylation and the formation of the intermolecular disulfide bond, which can regulate the trafficking of sortilin to EVs, thus preventing palmitoylation, which promotes trafficking of sortilin to the Golgi apparatus (22). Moreover, sortilin-derived propeptide decreases sortilin homodimers in EVs. Therefore, based on these findings, the mechanism regulating trafficking of sortilin via its dimerization with an intermolecular disulfide bond is regulated via ligand binding in the extracellular domain.

Sortilin Forms Homodimers on the Cell Surface

Figure 3A:
FIG. 3A-D shows the transmembrane domain of sortilin forms homodimers via noncovalent interaction.

Time-resolved fluorescence energy transfer (TR-FRET) assay was performed to detect sortilin homodimerization. Expression vectors of FLAG-sortilin and 6×His-sortilin were constructed for the TR-FRET assay (FIG. 1A). FLAG-tag and 6×His-tag were placed following propeptide and 3 amino acids (Ser-Ala-Pro) to detect the extracellular domains of FLAG-sortilin and 6×His-sortilin after propeptide cleavage (FIG. 1A). Both FLAG-sortilin and 6×His-sortilin were overexpressed in HEK293 cells. Protein expression of FLAG-sortilin and 6×His-sortilin was validated in the western blotting (FIG. 1B). This co-expression increased the FRET signal when compared to HEK293 cells overexpressing only 6×His-sortilin (FIG. 1C), indicating that sortilin forms homodimers on the cell surface. Also, an increased FRET signal was detected in homogenous TR-FRET (HTRF), a result which aligns with previous reports (26) (FIG. 3D). These results indicate that the FRET assay is effective in screening for molecules involved in sortilin dimerization.

Figures 2A, 2B, 2C, 2D:
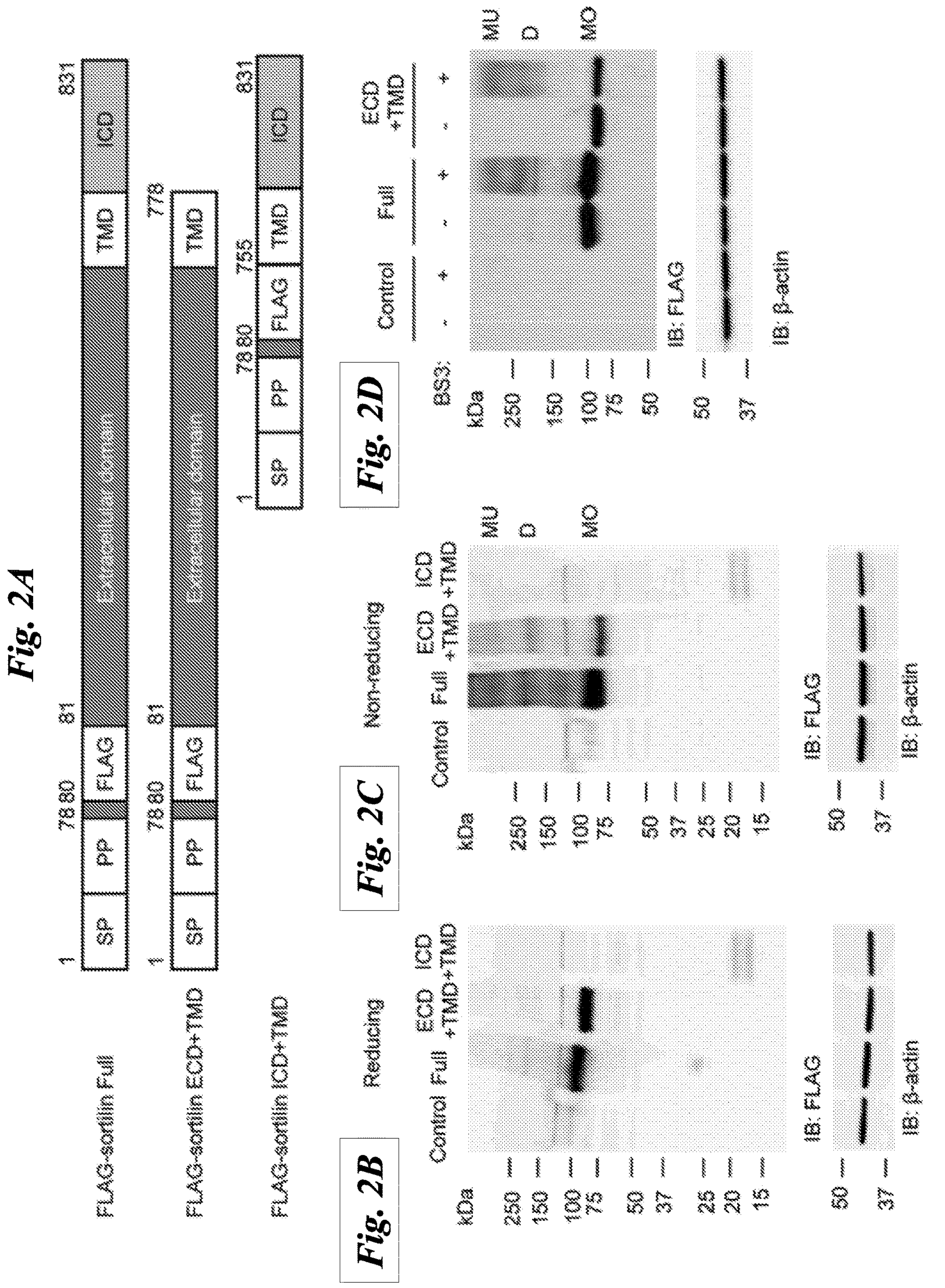
FIG. 2A-G shows sortilin forms homodimers in the extracellular and intracellular domains with intermolecular disulfide bonds in HEK293 cells.
Figures 2E, 2F, 2G:
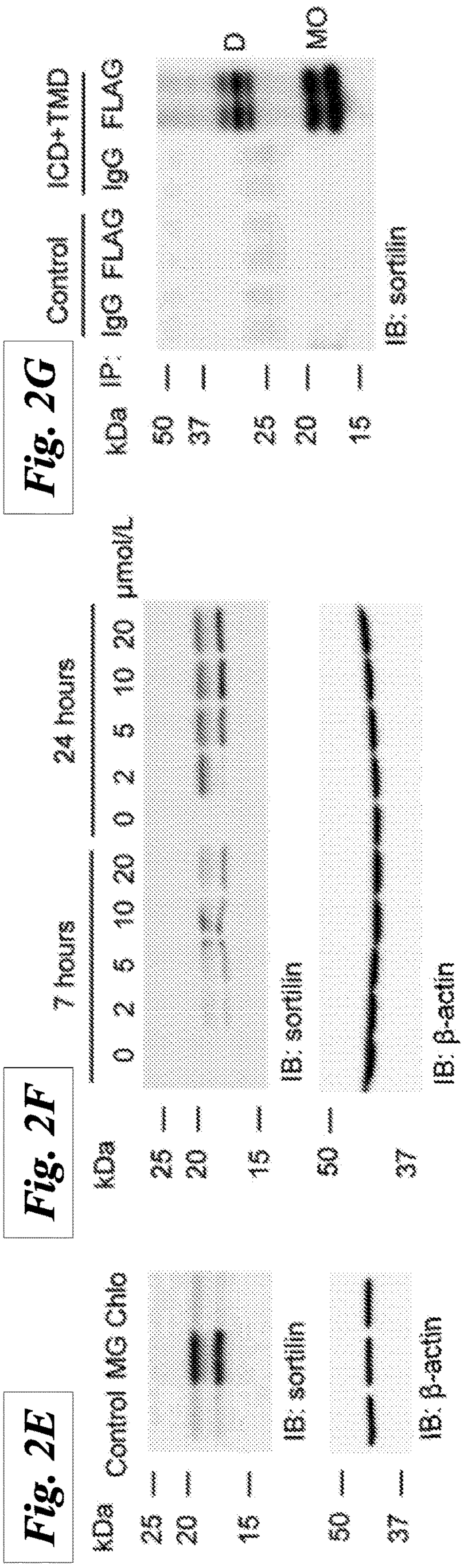

Sortilin Forms Homodimers in the Extracellular and Intracellular Domains with Intermolecular Disulfide Bonds To investigate whether the extracellular domain (ECD) or intracellular domain (ICD) is responsible for the dimerization of sortilin, expression vectors of FLAG-sortilin ECD plus transmembrane domain (TMD) and ICD+TMD were constructed and then overexpressed in HEK293 cells (FIG. 2A). In reducing western blotting, protein expressions of FLAG-sortilin Full, ECD+TMD and ICD+TMD were detected as bands of plausible molecular size (FIG. 2B). In non-reducing western blotting where disulfide bonds can be retained, FLAG-sortilin Full and ECD+TMD expressed a couple of bands (FIG. 2C). A band of 75-100 kDa was detected as monomers (FIG. 2C). Bands of approximately 200 kDa and higher molecular weight were detected as homodimers and multimers with intermolecular disulfide bonds (FIG. 2C). Next, FLAG-sortilin Full and ECD+TMD were cross-linked using water-soluble, non-cleavable cross-linker, BS3, in HEK293 cells. Both bands of homodimers and multimers appeared via the cross-linking (FIG. 2D). These data suggest that sortilin forms homodimers and multimers in the extracellular domain. Dimerization of FLAG-sortilin ICD+TMD was not clearly detected in the non-reducing western blotting using whole cell lysate (FIG. 2C) potentially due to low protein expression levels of FLAG-sortilin ICD+TMD (FIGS. 2B, 2C). Also, protein expression of FLAG-sortilin ICD+TMD was lower in HEK293 stably expressing FLAG-sortilin ICD+TMD (FLAG-sortilin ICD+TMD HEK293 cells). Therefore, it was determined whether FLAG-sortilin ICD+TMD can undergo degradation in proteasome and lysosome by adding proteasome inhibitor, MG-132, and lysosome inhibitor, chloroquine, to FLAG-sortilin ICD+TMD HEK293 cells, respectively. MG-132 increased protein expression of FLAG-sortilin ICD+TMD in a time- and concentration-dependent manner, while chloroquine did not, suggesting that FLAG-sortilin ICD+TMD is degraded in proteasome (FIGS. 2E, 2F). To detect homodimers of RAG-sortilin ICD+TMD, incubation with MG-132 was performed and immunoprecipitation with anti-FLAG antibody. In non-reducing western blotting, bands with molecular size approximately twice as high as monomers of FLAG-sortilin ICD+TMD were detected (FIG. 2G). These data indicate that sortilin forms homodimers with an intermolecular disulfide bond in the intracellular domain.

Figure 3B:
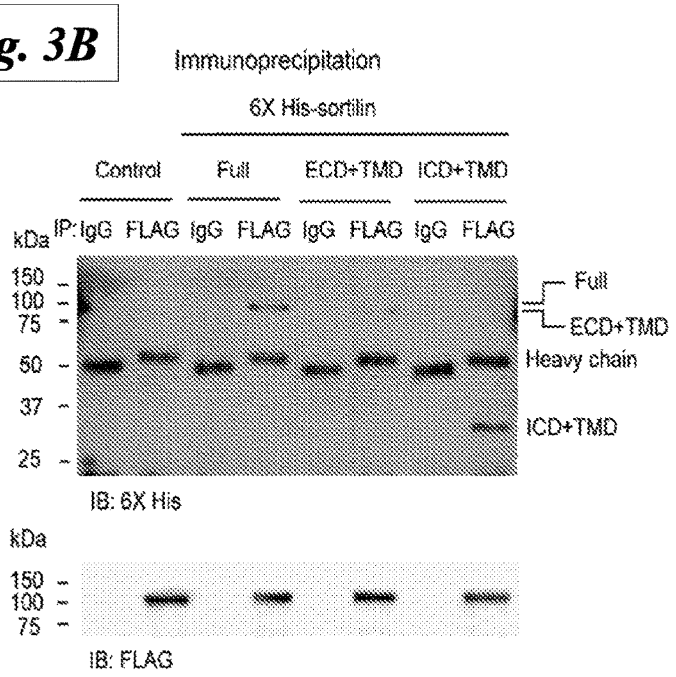
Figure 3C:
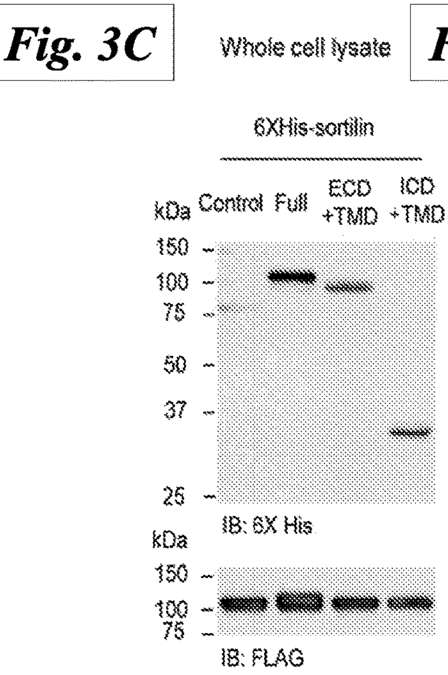
Figure 3D:
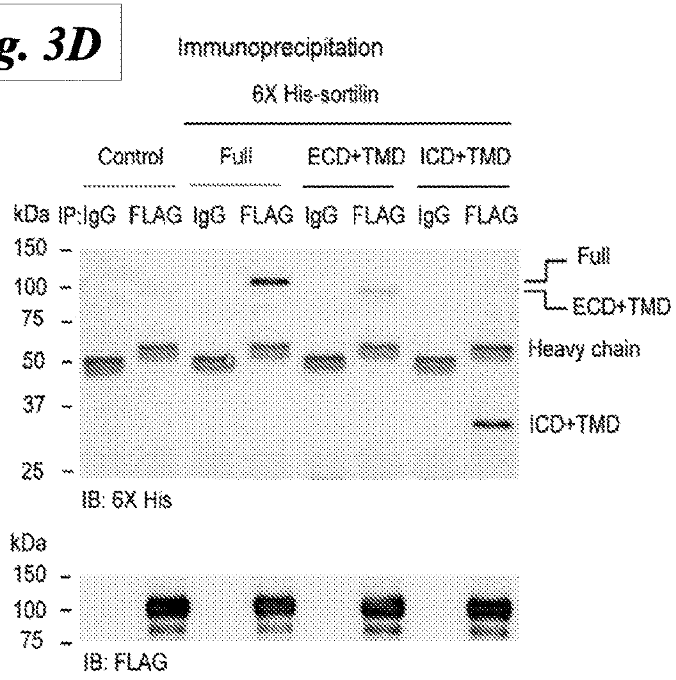

The Transmembrane Domain of Sortilin Forms Homodimers Via Noncovalent Interaction To confirm dimerization of sortilin in ECD and ICD, immunoprecipitation was performed using HEK293 cells stably overexpressing FLAG-sortilin Full (FLAG-sortilin Full HEK293 cells or FLAG-sortilin HEK293 cells) where 6×His-sortilin Full, ECD+TMD or ICD+TMD were transiently overexpressed, respectively (FIGS. 3A, 3B). 6×His-sortilin Full, ECD+TMD and ICD+TMD were precipitated with FLAG-sortilin Full (FIG. 3B). Since their constructs have a transmembrane domain, the possibility that the transmembrane domain forms dimers remained. Therefore, to investigate dimerization of a transmembrane domain, immunoprecipitation was carried out using HEK293 cells stably overexpressing FLAG-sortilin ECD+TMD (FLAG-sortilin ECD+TMD HEK293 cells) where 6×His-sortilin ICD+TMD was transiently overexpressed (FIGS. 3C, 3D). 6×His-sortilin Full and ECD+TMD were also overexpressed as a positive control (FIGS. 3C, 3D). 6×His-sortilin Full, ECD+TMD and ICD+TMD were precipitated with FLAG-sortilin ECD+TMD (FIG. 3D). Binding of FLAG-sortilin ECD+TMD and 6×His-sortilin ICD+TMD indicate that sortilin can form homodimers via noncovalent interaction in the transmembrane domain.

Figures 4A, 4B, 4C, 4D:
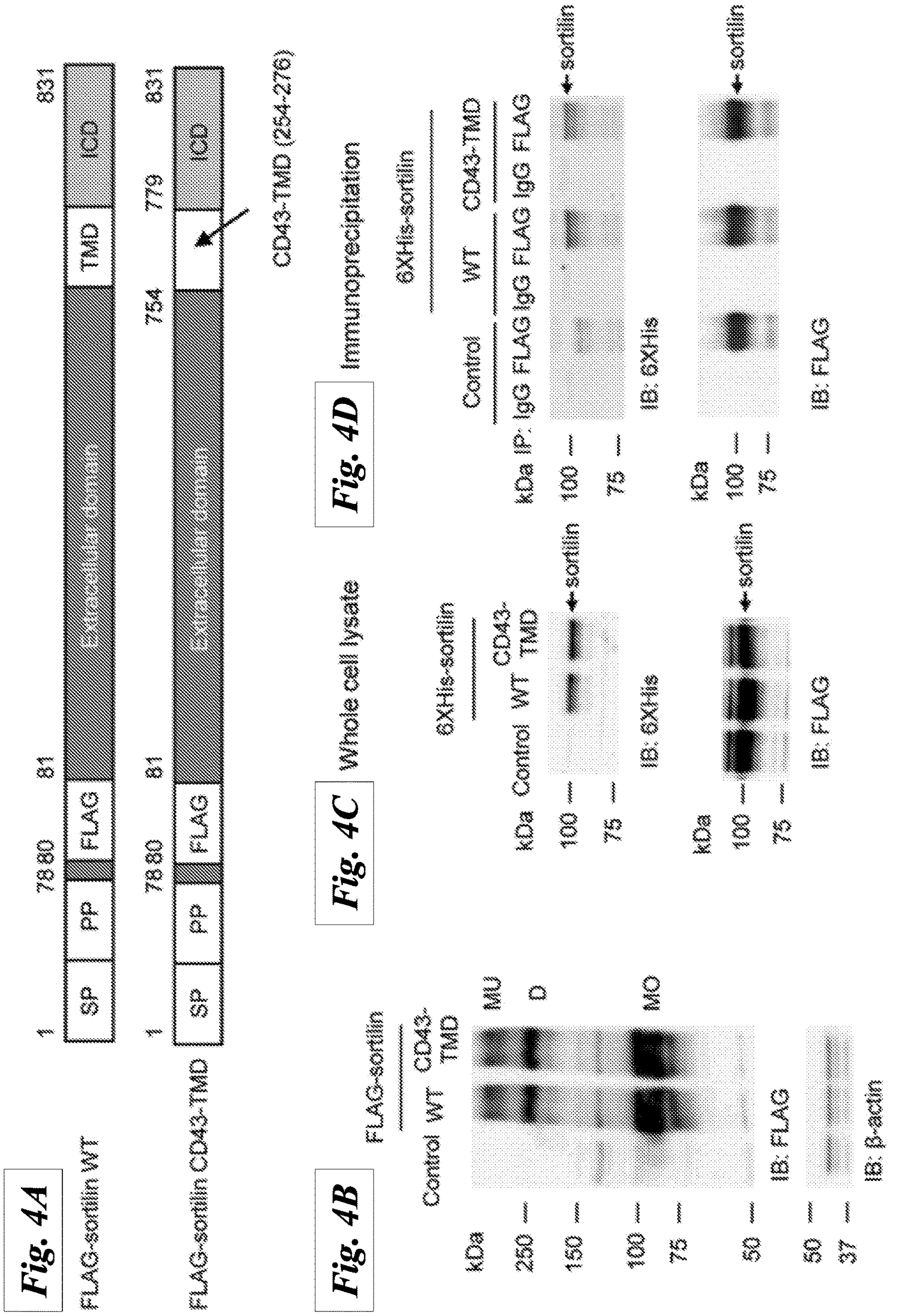
FIG. 4A-D shows that substituting the transmembrane domain of sortilin with the corresponding domain of CD43 does not decrease the dimeric form of sortilin.
Figure 4G:
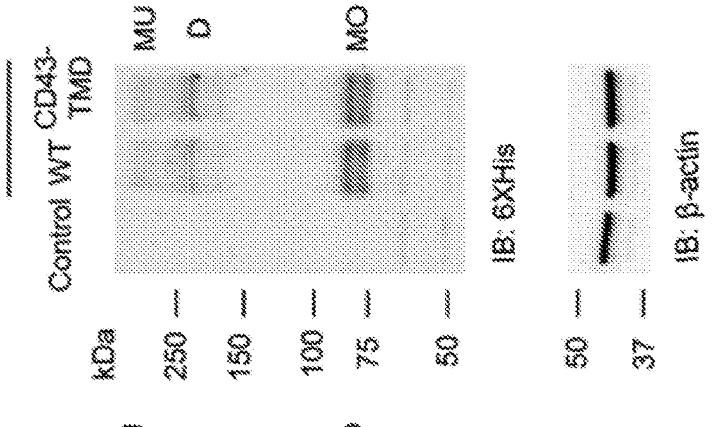
FIG. 4F-G shows that in FLAG-sortilin HEK293 cells, 6×His-sortilin WT or 6×His-sortilin CD43-TMD were overexpressed. The cell lysates were subjected to non-reducing Western blotting with anti-FLAG antibody (FIG. 4F) and anti-6×His antibody (FIG. 4G), demonstrating that substituting the transmembrane domain of sortilin with that of CD43 did not decrease dimerization (n=3). IB, immunoblotting.
Figure 4F:
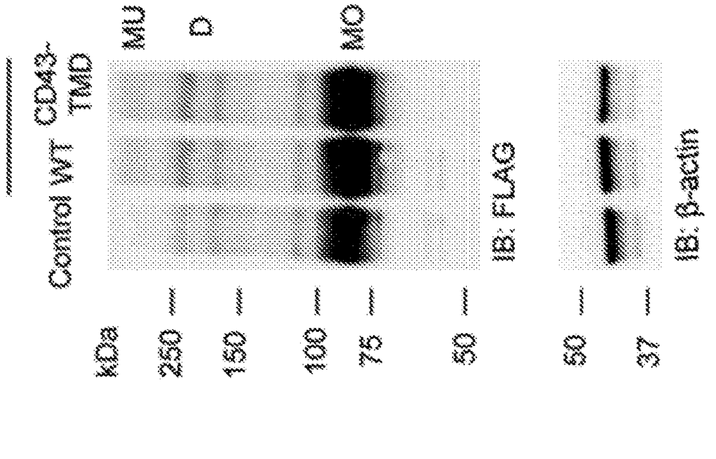
Figure 4E:
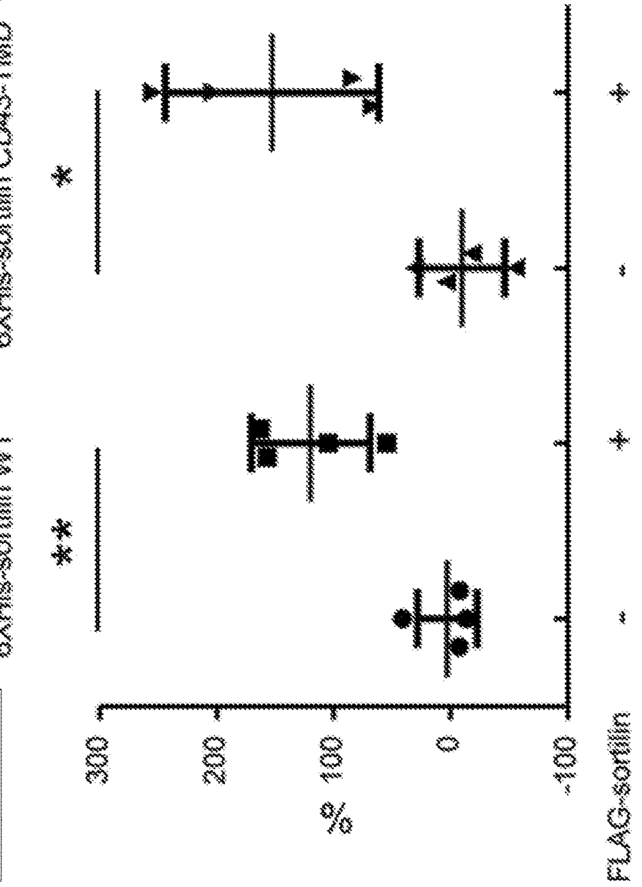
FIG. 4 E shows that in FLAG-sortilin HEK293 cells or HEK293 cells, 6×His-sortilin CD43-TMD was overexpressed. The cells were subjected to TR-FRET assay. Change of FRET signal by expression of 6×His-sortilin WT or CD43-TMD is indicated by percent change (mean S.D., n=4, one independent experiment). Error bars represent S.D. *$P<0.05$; **$P<0.01$ by t test.
Figure 10A:
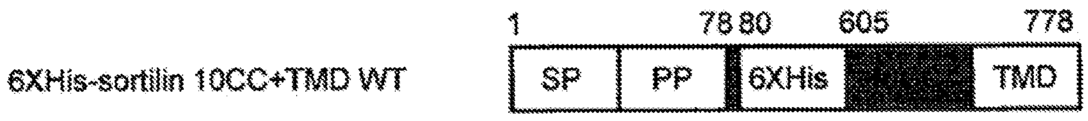
FIG. 10A-B shows the expression vector of 6×His-sortilin 10CC+TMD was constructed (FIG. 10A) and transfected in HEK293 cells. Dimerization of 6×His-sortilin 10CC+TMD was detected in the non-reducing western blotting with anti-6×His antibody (FIG. 10B) (n=3).
Figure 10B:
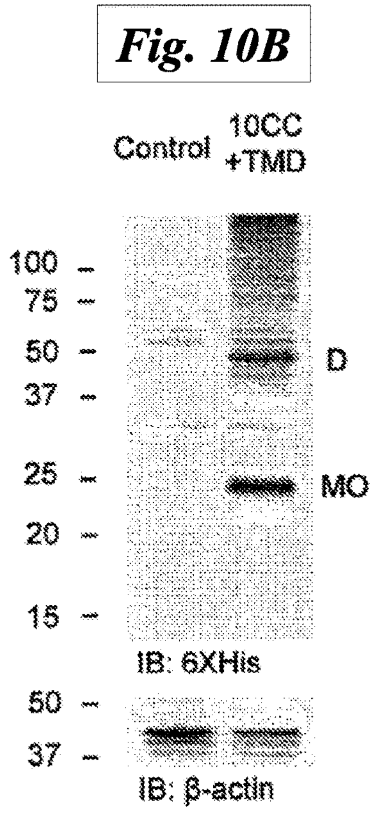

Substituting the Transmembrane Domain of Sortilin with the Corresponding Domain of CD43 does not Generate a Monomeric Form of Sortilin To investigate the contribution of the transmembrane domain of sortilin on dimerization, the transmembrane domain was replaced with that of CD43, which does not form homodimers (sortilin CD43-TMD), as was previously reported (FIG. 4A) (25). Sortilin CD43-TMD formed homodimers in the non-reducing western blotting (FIG. 4B). Also, 6×His-sortilin CD43-TMD was precipitated with FLAG-sortilin wild-type in the immunoprecipitation experiment of HEK293 cells as well as 6×His-sortilin wild-type (FIGS. 4C, 4D), and co-expression of FLAG-sortilin and 6×His-sortilin CD43-TMD increased FRET signal in HEK293 cells as well as 6×His-sortilin wild-type (FIG. 10). These data suggest that inhibiting dimerization of the transmembrane domain is not sufficient to suppress dimerization of sortilin possibly due to dimerization of the intracellular and extracellular domain.

Mutation of Cys783 Abolished Dimerization of Sortilin

Figure 5A:
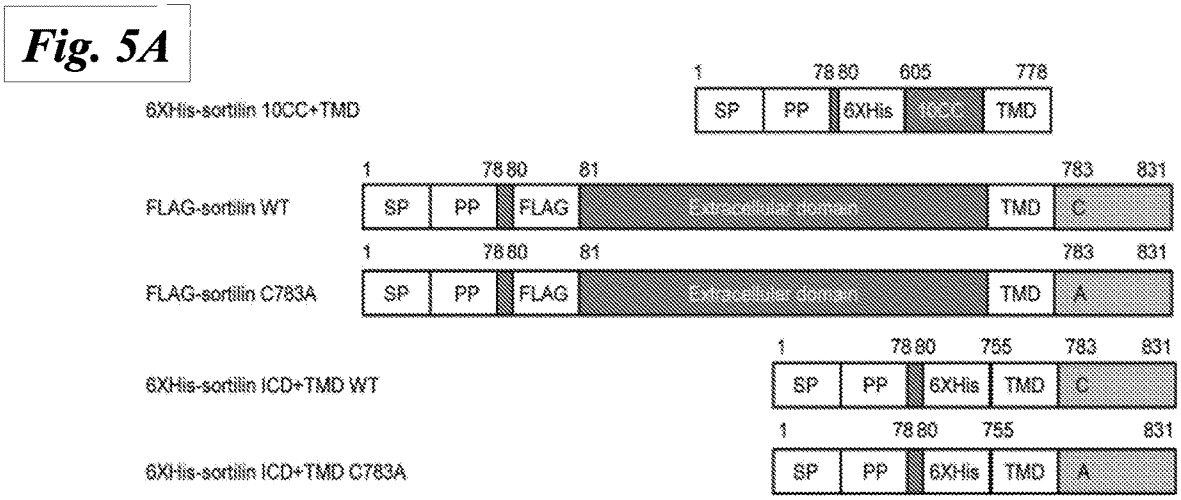
FIG. 5A-F shows that mutation of $Cys^{783}$ abolished dimerization of sortilin.
Figure 5B:
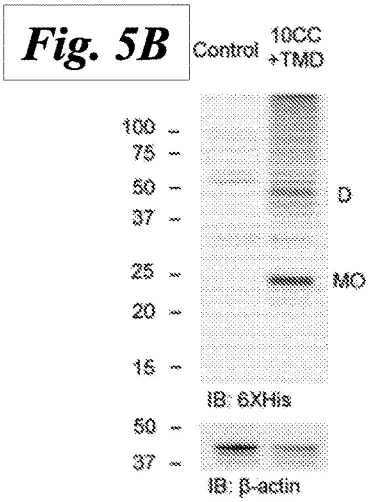
Figure 5C:
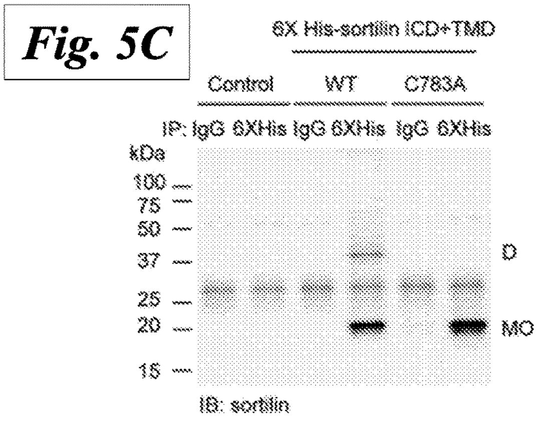
Figure 5D:
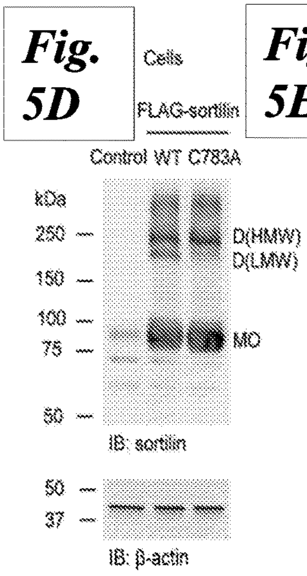
Figure 5E:
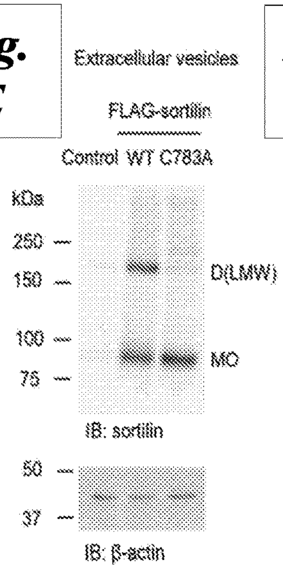
Figure 5F:
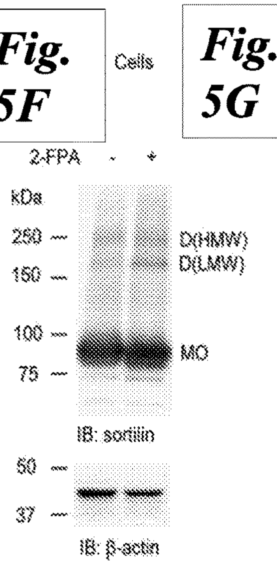
Figure 5G:
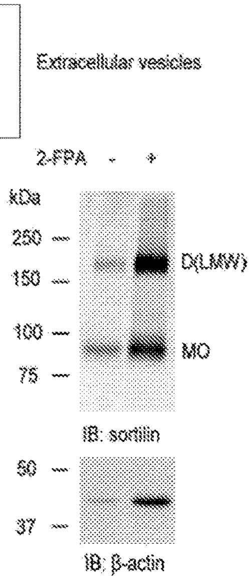

Previous reports showed that cysteines play an important role in maintaining the structure of sortilin since they form intramolecular disulfide bonds in the extracellular domain of sortilin (27). In addition, in this study, it is demonstrated that intermolecular disulfide bonds are formed within homodimers. Although the cysteines responsible for the formation of intermolecular disulfide bonds in the extracellular domain have been not yet identified, the 10CC domain formed dimers in the non-reducing western blotting (FIG. 10), indicating that intermolecular disulfide bonds can be formed within the 10CC domain. Next, the intermolecular disulfide bond was examined in the intracellular domain. Since sortilin has only one cysteine ($Cys^{783}$) in the intracellular domain, the cysteine was expected to form an intermolecular disulfide bond for dimerization in the intracellular domain. $Cys^{783}$ was replaced by alanine (C783A) in 6×His-sortilin ICD+TMD and FLAG-sortilin Full (FIG. 5A). 6×His-sortilin ICD+TMD C783A did not form homodimers in HEK293 cells (FIG. 5B). Surprisingly, FLAG-sortilin C783A decreased only homodimers of low molecular weight in HEK293 cells, although it did not change those of high molecular weight and multimers (FIG. 5C). The homodimers of low molecular weight were mainly transported to EVs, while homodimers of high molecular weight and multimers were mainly not transported to EVs (FIG. 5D). Therefore, FLAG-sortilin C783A significantly decreased transport of dimerized sortilin to EVs (FIG. 5D). Since $Cys^{783}$ was reported to be palmitoylated (22), the connection between palmitoylation and intermolecular disulfide bond was studied by incubating FLAG-sortilin HEK293 cells with an inhibitor of palmitoylation, 2-fluoropalmitic acid (2-FPA) (22), which increased only homodimers of lower molecular size in the cells (FIG. 5E). These data indicate that $Cys^{783}$ can be shared by palmitoylation and the intermolecular disulfide bond. Also, 2-FPA increased dimerization of FLAG-sortilin in the EVs (FIG. 5E), suggesting that a decrease of the homodimers in the EVs via the mutation of $Cys^{783}$ is due to a decrease in dimerization, not palmitoylation.

Binding of Sortilin-Derived Propeptide Suppresses Dimerization of Sortilin.

Figures 6A, 6B, 6C, 6D, 6E:
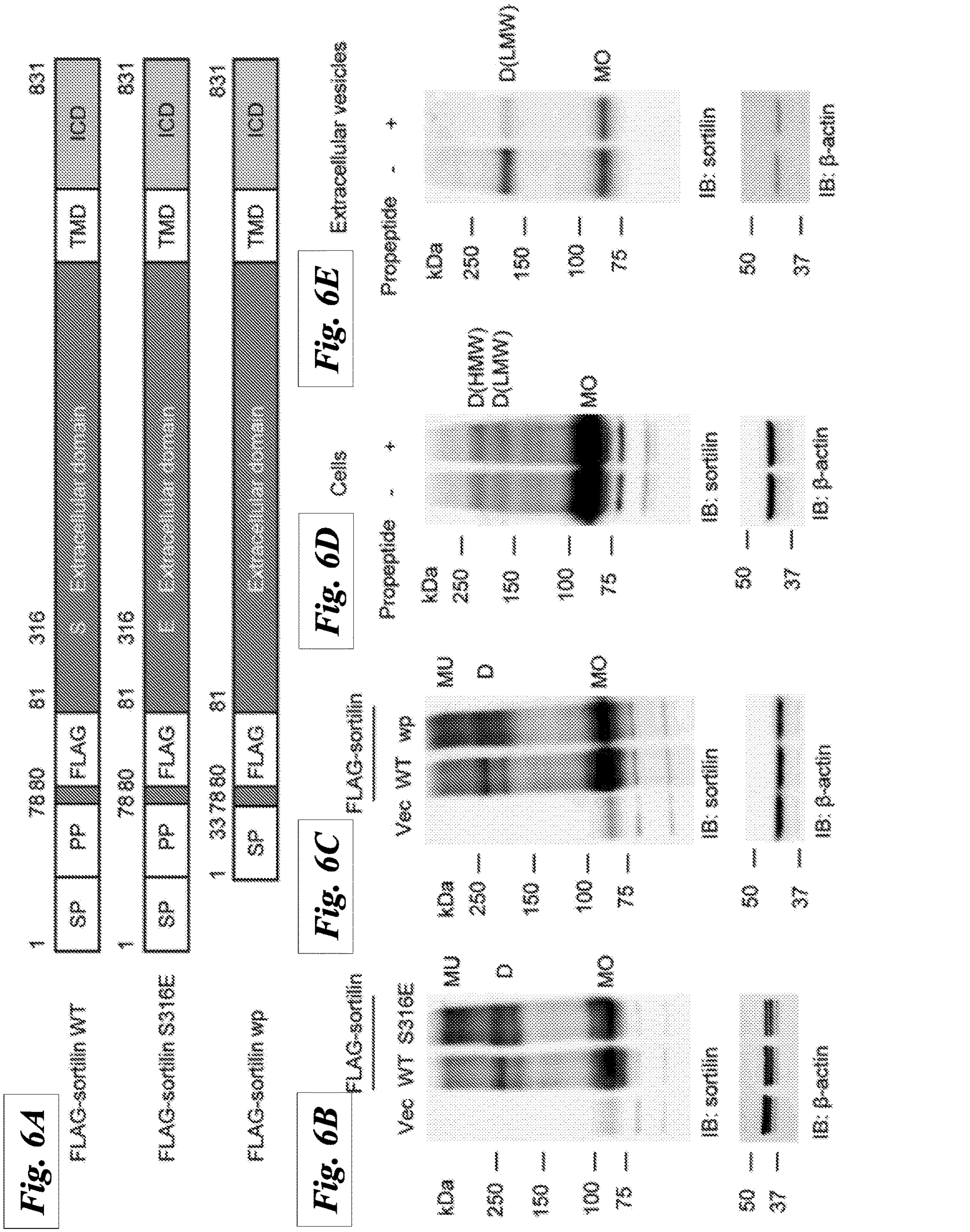
FIG. 6A-E shows that sortilin 5316E and without propeptide (wp) increases dimerization in HEK293 cells, and the addition of propeptide decreases dimerization in the extracellular vesicles of FLAG-sortilin HEK293 cells.

The structure of the Vps 10p domain in both sortilin and SorLA has been reported (28) (29). SorLA has different configuration in a ligand-free state or propeptide-bound state. Similar changes can take place in sortilin, and these different states can form monomers and homodimers of sortilin. Since the S316E mutation inhibits binding with sortilin-derived propeptide (29), a S316E mutant was used (FIG. 6A) to investigate the effects of the propeptide binding on dimerization. S316E increased dimerization in HEK293 cells concomitantly with a decrease in monomers (FIG. 6B). To further validate the effect of the propeptide binding on dimerization, sortilin without propeptide (wp) (27) was constructed (FIG. 6A) and overexpressed in HEK293 cells. Sortilin wp also increased the dimerization in HEK293 cells, concomitantly with a decrease in monomers (FIG. 6C). Also, the addition of sortilin-derived propeptide decreased dimerization in the extracellular vesicles of FLAG-sortilin HEK293 cells (FIG. 6E), though it did not affect dimerization in the cells (FIG. 6D).

Soluble Sortilin Exists as Homodimers

Figure 7A:
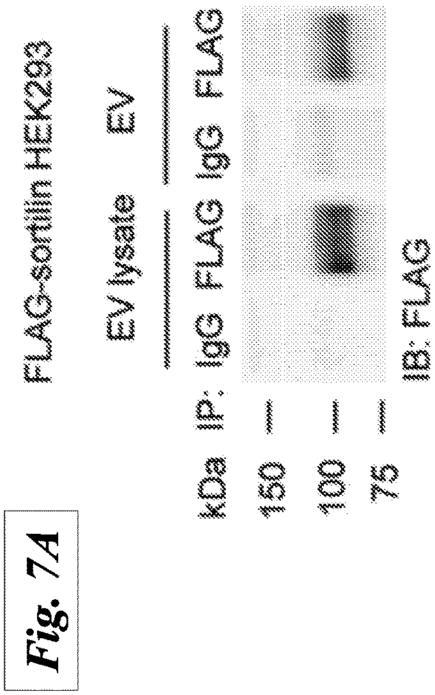
FIG. 7A-E shows that soluble sortilin forms homodimers.
Figure 7B:
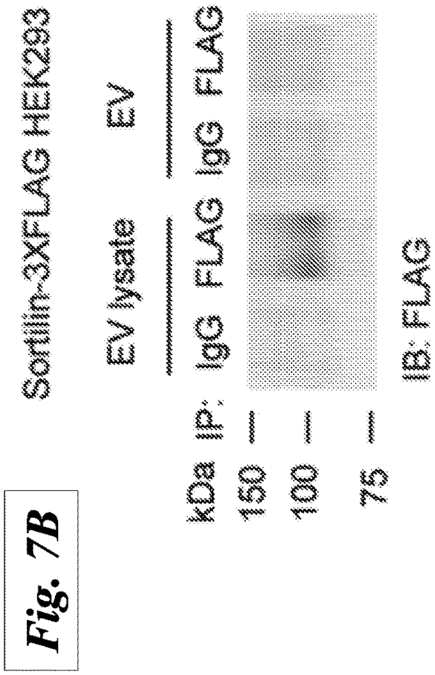
Figure 7C:
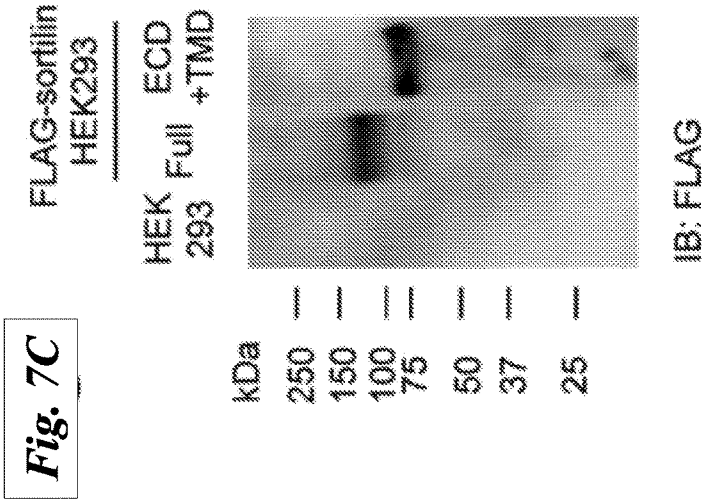
Figure 7D:
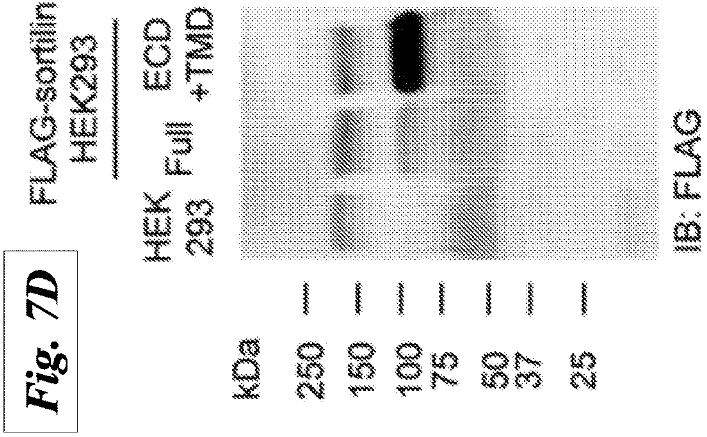
Figure 7E:
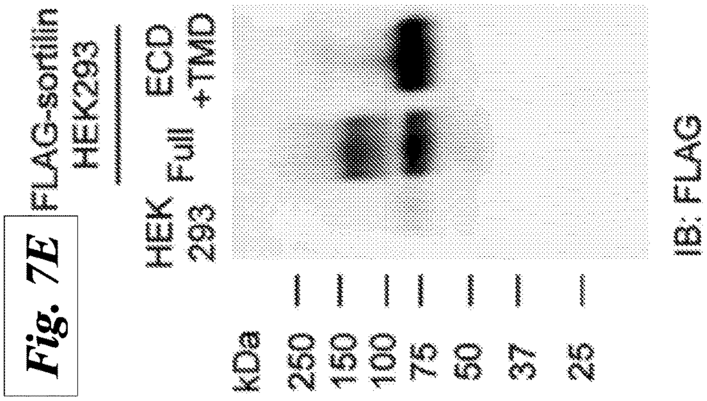

It has been reported that serum sortilin levels associate with cardiovascular risk, such as aortic calcification (30) and atherothrombosis (31), as well as depression (32). It has been also demonstrated that soluble sortilin can activate the survival of cancer cells (5) (33). Therefore, it is important to understand whether soluble sortilin can contribute to diseases via the formation of monomers and/or homodimers. In addition, it is critical to determine the orientation of sortilin on the EV membrane for the detection of soluble sortilin and sortilin in EVs. Since serum sortilin levels has been measured using antibodies against the extracellular domain of sortilin, these antibodies can detect both as long as the extracellular domain of sortilin locates outside of EVs. Therefore, to determine the orientation of sortilin on the EV membrane, an immunoprecipitation assay was performed using EVs secreted from FLAG-sortilin Full HEK293 cells and HEK293 cells stably expressing sortilin with 3×FLAG at C-terminus (sortilin-3×FLAG). FLAG-sortilin was detected in EVs and the lysate (FIG. 7A), but sortilin-3×FLAG was detected in the lysate only (FIG. 7B), suggesting that the extracellular domain of sortilin located outside of EVs. Next, to detect forms of soluble sortilin secreted from FLAG-sortilin HEK293 cells, a non-reducing western blotting was performed using EV-deprived culture medium. The molecular size of soluble sortilin was calculated as approximately 120 kDa in the non-reducing western blotting (FIG. 7C). Since this size is higher than that detected in the reducing western blotting (FIG. 7D), the band of 120 kDa was detected as homodimers. Also, forms of soluble sortilin secreted from FLAG-sortilin ECD+TMD HEK293 cells were investigated since the intracellular domain of sortilin can be cleaved (6) (34). Soluble sortilin from FLAG-sortilin ECD+TMD HEK293 cells was detected as a band at approximately 80 kDa (FIG. 7C) in the form of monomers. Next, soluble sortilin was purified using an anti-FLAG antibody affinity column using EV-deprived culture medium. Soluble sortilin secreted from FLAG-sortilin HEK293 cells was detected as bands of 80 and 120 kDa, which associate with dimers of soluble sortilin that partially changed their form to monomers during the process of purification (FIG. 7E). These data indicate that the band of 120 kDa represents the soluble sortilin dimer.

Discussion

As provided herein, sortilin promotes vascular calcification via its trafficking of tissue-nonspecific alkaline phosphatase (TNAP), a facilitator of calcification, to EVs (19). Also, other groups have reported that sortilin promotes exosome release and forms a complex with two tyrosine receptors, tropomyosin-related kinase B (TrkB) and epidermal growth factor receptor (EGFR), which can play an important role in the control of the cancer cell microenvironment and tumor angiogenesis (6). Given these results, the major objective of the study was to understand how sortilin is transported to EVs in order to potentially inhibit the atypical expression levels observed in multiple diseases, including cardiovascular disease.

Accordingly, sortilin forms homodimers with an intermolecular disulfide bond. In the intracellular domain of sortilin, $Cys^{783}$ forms an intermolecular disulfide bond to generate homodimers. Since $Cys^{783}$ has been reported to be palmitoylated (22), formation of an intermolecular disulfide bond can compete with palmitoylation at $Cys^{783}$. The palmitoylation inhibitor increased sortilin dimerization. Furthermore, dimerized sortilin with an intermolecular disulfide bond at $Cys^{783}$ acts as the main dimer transported to EVs, and loss of the intermolecular disulfide bond at $Cys^{783}$ via mutation can cease the transport of dimerized sortilin to EVs. Since the palmitoylation inhibitor increased transport of dimerized sortilin to EVs, formation of an intermolecular disulfide bond at $Cys^{783}$ residue can facilitate transport of dimerized sortilin to EVs, possibly due to the fact that palmitoylation accelerates trafficking to the Golgi apparatus (22) (FIG. 8).

The immunoprecipitation experiments showed that, in the transmembrane domain of sortilin, noncovalent interaction can occur to form homodimers. However, inhibiting binding in the transmembrane domain was not sufficient to suppress dimerization of sortilin. This can be explained by sortilin covalent binding in the intracellular and extracellular domain, while, concurrently, other type I transmembrane proteins such as PSGL-1 (25) and amyloid precursor protein (35) form homodimers through the transmembrane domain.

In the extracellular domain, 10CC domain showed intermolecular disulfide bonds. The 10CC domain has 10 cysteines, which form intramolecular disulfide bonds (27). However, the results support the possibility that some of cysteines in the 10CC domain contribute to the formation of intermolecular disulfide bonds for homodimers. Since C783A mutant decreased only homodimers of low molecular weight, homodimers with cysteines in the 10CC domain were formed, and the C783A mutant existed as homodimers of high molecular weight and multimers. To not be bound by a particular theory, it was contemplated previously that the interaction of propeptide binding site and 10CC domain occurs (29). It was further contemplated that binding of sortilin-derived propeptide affects dimerization. Since the structure of sorLA, which, similar to sortilin, has a VpslOp domain, can change in a ligand-free state or propeptide-bound state (28), and that these two different states can contribute to the formation of either monomers or homodimers of sortilin (FIG. 8). Also shown was that both sortilin 5316E and sortilin wp increased formation of homodimers, while the addition of propeptide reduced them. Since the ligands regulated dimerization of sortilin, future studies should investigate the effects of other ligands, such as progranulin (17) and neurotensin (36), in addition to sortilin-derived propeptide, on sortilin dimerization.

Here, it was demonstrated that soluble sortilin can exist as homodimers. Moreover, the intracellular domain is essential for the dimerization of soluble sortilin. Previous studies used sortilin overexpressed as recombinant protein lacking in transmembrane and intracellular domains, indicating that soluble sortilin has been present in form of monomers (33) (37). As demonstrated herein, is a method to produce dimerized soluble sortilin. Since, in the purification process of dimerized soluble sortilin, some of intermolecular disulfide bonds can be destroyed, resulting in monomer formation, the purification procedure can be improved. In addition, dimerized soluble sortilin can be used to examine physiological and pathological functions of its soluble form.

The findings of dimerized soluble sortilin have important implications in a clinical setting, since serum sortilin can act as a biomarker to detect cardiovascular and neurologic diseases (30) (31) (32). Therefore, it is important to clarify the differences between monomers and dimers of soluble sortilin, and the monomer/dimer ratio in serum for these diseases. This can allow for a more accurate diagnosis for the diseases, similar to the detection of high molecular weight adiponectin for metabolic syndrome (38) (39). Also, it was determined that the extracellular domain of sortilin located outside of EVs. This finding validates the possibility that the detection of sortilin-positive EVs can be possible using antibodies against the extracellular domain. Clarifying the association of sortilin-positive EVs with various diseases can be useful as a clinically-relevant surrogate for disease progression. In fact, the potential for using exosomal proteins in disease diagnosis and prognosis prediction has been increasing (40).

In conclusion, it was demonstrated that sortilin forms homodimers, which can play an important role in the trafficking of sortilin to the EVs and can be regulated using an intermolecular disulfide bond. In addition, sortilin-derived propeptide can control the dimerization of sortilin, and therefore the possibility of its regulation via ligand binding in the extracellular domain. Based on these findings, it is expected that molecules inhibiting sortilin dimerization, such as small molecule compounds, antibodies and peptides, can provide new therapeutic approaches to treat EV-associated diseases, including vascular calcification and cancer, by suppressing transport of sortilin and disease-causing proteins bound with sortilin to EVs.

Example 2: Experimental Procedures

Chemicals and Reagents

MG-132 (Cat #7449) and Chloroquine diphosphate salt (Cat #C6628) were purchased from Sigma-Aldrich Co. LLC. (Sigma). 2-fluoropalmitic acid (2-FPA, Cat #90380) was purchased from Cayman Chemical. Sortilin propeptide (sortilin-derived propeptide) (Cat #049-75, Lot #432841) was purchased from Phoenix Pharmaceuticals, Inc. Primers were purchased from Integrated DNA Technologies, Inc. PCR reagents were purchased from EMD Millipore Corporation.

Vectors and Constructs

Expression vectors were constructed in pcDNA3.1 (+) vector (Thermo Fisher Scientific Inc., Cat#V79020). Constructs of human sortilin (NM_002959.5) were generated by inserting FLAG (DYKDDDDK) or 6×His (HHHHHH) tag into 3 amino acids (S73A1330) behind the furin cleavage site R74WRR77 (35) using site-mutagenesis: pcDNA3.1(+) FLAG-sortilin full-length (Full), amino acids (aa) 1-831; pcDNA3.1(+) FLAG-sortilin ECD+TMD, aa1-778; pcDNA3.1(+) FLAG-sortilin ICD+TMD, aa1-831 (A81-754); pcDNA3.1(+) 6×His-sortilin full-length (Full); pcDNA3.1(+) 6×His-sortilin ECD+TMD; pcDNA3.1(+) 6×His-sortilin ICD+TMD; pcDNA3.1(+) 6×His sortilin 10CC domain+TMD, aa1-778 (681-604); pcDNA3.1(+) FLAG-sortilin C783A; pcDNA3.1(+) 6×His-sortilin ICD+TMD C783A; pcDNA3.1(+) FLAG-sortilin S316E; pcDNA3.1(+) FLAG-sortilin without propeptide, aa1-831 (34-77). Constructs of sortilin CD43-TMD were generated by overlapping PCR strategy using a CD43 expression vector (Origene, Cat #RC204195, NM_003123) (25): pcDNA3.1(+) FLAG-sortilin CD43-TMD, sortilin aa1-754, CD43 aa254-276, sortilin aa779-831; pcDNA3.1(+) 6×His-sortilin CD43-TMD. Expression vector of sortilin with 3×FLAG at C-terminus (sortilin-3×FLAG, Cat # EX-M0397-M14) was purchased from GeneCopoeia, Inc.

Western Blot Analysis

Cells, EVs and the supernatant of culture medium were lysed with IP lysis buffer (Thermo Fisher Scientific Inc., Cat #87787) containing protease inhibitor (Roche Diagnostics, Cat #04693159001). Protein concentration was measured using the bicinchoninic acid (BCA) method (Thermo Fisher Scientific Inc., Cat #23225). Laemmli buffer (Boston Bioproduct; non-reducing, Cat #BP-110NR; reducing, Cat #BP-111R) was added to the lysate, and boiled at 95° C. for 5 minutes. Total protein was separated by 4-12% SDS-PAGE and transferred to polyvinylidene difluoride (PVDF) membrane using iBlot Western blotting system (Life Technologies) or conventional wet method. Primary antibodies against human sortilin ICD (rabbit 1:1000; Abcam plc., Cat #ab16640, Lot #GR185198-1), human (3-actin (mouse 1:2000; Novus Biologicals, LLC, Cat #NB600-501, Lot #014M4759), FLAG (rabbit 1:1000; Sigma, Cat #F4725, Lot #093M4798, mouse (M2) 1:1000; Sigma, Cat #F1804, Lot #SLBJ4607V), 6×His (mouse 1:1000; Abcam plc., Cat #ab18184, Lot #GR247674-1).

Immunoprecipitation

Cells or EVs were lysed in IP lysis buffer. Anti-FLAG M2 antibody (5 μg) or mouse IgG (5 lig, R&D Systems, Cat #MAB002, Lot # IX2415091) were incubated with Dynabeads with Protein G (Thermo Fisher Scientific Inc., Cat #10004D) by rotation for overnight at 4° C. Cell lysate was incubated for 4 hours at 4° C. under rotating conditions. The bead-antibody-protein complex was washed with PBS 3 times. Then, Laemmli buffer was added to the precipitates for SDS-PAGE.

Cross-Linking Experiment

Chemical cross-linking was carried out by incubating HEK293 cells transiently overexpressing FLAG-sortilin Full, ECD+TMD, or ICD+TMD with 1 mmol/L of bis (sulfosuccinimidyl) suberate (BS3), water-soluble, non-cleavable cross-linker (Thermo Fisher Scientific Inc., Cat #21580) at room temperature for 30 minutes. Reaction was stopped with 15-minute incubation of 1 mol/L Tris-HCl (pH7.4), and cells were centrifuged at 1,000 rpm for 5 minutes to remove the buffer including BS3, and washed with PBS. Then, cells were lysed in IP lysis buffer for western blotting.

Cell Culture of HEK293 Cells and Establishment of Transfectants

HEK293 cells were purchased from American Type Culture Collection (ATCC) and maintained in Eagle's minimum essential medium (EMEM, ATCC, Cat #30-2003) supplemented with 10% fetal bovine serum (FBS), penicillin (100 U/mL), and streptomycin (100 μg/mL) at 37° C. in a humidified atmosphere of 5% CO2. For transfection in HEK293 cells, Lipofectamine 2000 reagent (Thermo Fisher Scientific Inc., Cat #11668019) was used, according to the manufacturer's protocol. HEK293 cells stably expressing FLAG-sortilin Full, ECD+TMD, ICD+TMD and sortilin-3×FLAG were obtained by transfection with pcDNA3.1(+) FLAG-sortilin Full, pcDNA3.1(+) FLAG-sortilin-ECD+TMD, pcDNA3.1(+) FLAG-sortilin ICD+TMD, and expression vector of sortilin-3×FLAG (GeneCopoeia, Inc., Cat # EX-M0397-M14), respectively. These cell lines were maintained in EMEM supplemented with 10% FBS, penicillin/streptomycin, and geneticin 800 μg/mL. Cells were incubated in the incubator with MG-132 and chloroquine during the indicated time, and with 2-FPA and sortilin propeptide for 24 hours, respectively.

Separation of Culture Medium to Supernatant and EVs

Separation of culture medium to supernatant and EVs was performed according to the protocol previously reported (41). Culture medium underwent centrifugation at 1,000 rpm for 5 minutes to remove cell debris. Then, the supernatant and EVs were separated by ultracentrifugation at 100,000 g for 40 minutes at 4° C. (Optima Max Ultracentrifuge, Beckman Coulter).

TR-FRET and Homogenous TR-FRET (HTRF)

TR-FRET and HTRF were performed as described (26). FLAG-sortilin Full HEK293 cells were harvested using dissociation solution (e.g., from Sigma Aldrich, Cat

#C5914) 24 hours after transfection of 6×His-sortilin expression vector. An incubation under the circle rotator was performed at 4° C. with 1×106 cells/mL for TR-FRET and 2×106 cells/mL for HTRF containing 1 nmol/L Anti-FLAG® (M2)-Cryptate (Cisbio Bioassays, Cat #61FG2KLA, Lot #25A) and 3 nmol/L Anti-6HIS-XL665 (Cisbio Bioassays, Cat #61HISXLA, Lot #56A) in PBS supplemented with 25% FBS. For TR-FRET, cells were centrifuged at 1,000 rpm for 5 min to remove the antibodies, and resuspended in PBS, and applied into a 96-well white plate. For HTRF, cells were applied without removing the antibodies into a 96-well white plate. Then, the plate was read (excitation: 320 nm, emission: 620 nm (cutoff 570 nm), 665 nm (cutoff 630 nm), Delay 50 ps, Integration 500 ps). The FRET signal was calculated as (the ratio of counts per seconds 665:620)×10,000, and % change of the FRET signal by 6×His-sortilin expression was expressed.

Purification of Soluble Sortilin

EV-deprived culture medium of FLAG-sortilin Full or ECD+TMD HEK293 cells were subjected to ANTI-FLAG® M2 Affinity Gel (Sigma, Cat #A2220). Soluble sortilin with FLAG-tag was eluted with 100 μg/mL FLAG-peptide (Sigma, F3290, Lot #SLBR6767V). Purified soluble sortilin was dialyzed in PBS.

Statistical Analysis

Data are presented as means±S.E. of the indicated number. Comparison was performed by analysis of variance following unpaired t-test.

REFERENCES FOR EXAMPLES 1 & 2

1. Raposo, G., and Stoorvogel, W. (2013) Extracellular vesicles: exosomes, microvesicles, and friends. J. Cell Biol. 200, 373-383.
2. Simons, M., and Raposo, G. (2009) Exosomes—vesicular carriers for intercellular communication. Curr. Opin. Cell Biol. 21, 575-581.
3. Thery, C., Ostrowski, M., and Segura, E. (2009) Membrane vesicles as conveyors of immune responses. Nat. Rev. Immunol. 9, 581-593
4. Carlo, A. S., Nykjaer, A., and Willnow, T. E. (2014) Sorting receptor sortilin-a culprit in cardiovascular and neurological diseases. J. Mol. Med. (Berl). 92, 905-911
5. Beraud-Dufour, S., Devader, C., Massa, F., Roulot, M., Coppola, T., and Mazella, J. (2016) Focal Adhesion Kinase-Dependent Role of the Soluble Form of Neurotensin Receptor-3/Sortilin in Colorectal Cancer Cell Dissociation. Int. J. Mol. Sci. 17, 1860
6. Wilson, C. M., Naves, T., Vincent, F., Melloni, B., Bonnaud, F., Lalloue, F., and Jauberteau, M. O. (2014) Sortilin mediates the release and transfer of exosomes in concert with two tyrosine kinase receptors. J. Cell. Sci. 127, 3983-3997
7. Wilson, C. M., Naves, T., Akhrass H. A., Vincent, F., Melloni, B., Bonnaud, F., Lalloue, F., and Jauberteau, M. O. (2016) A new role under sortilin's belt in cancer. Commun. Integr. Biol. 9, e1130192
8. Roselli, S., Pundavela, J., Demont, Y., Faulkner, S., Keene, S., Attia, J., Jiang, C. C., Zhang, X. D., Walker, M. M., and Hondermarck, H. (2015) Sortilin is associated with breast cancer aggressiveness and contributes to tumor cell adhesion and invasion. Oncotarget 6, 10473-10486
9. Kaddai, V., Jager, J., Gonzalez, T., Najem-Lendom, R., Bonnafous, S., Tran, A., Le
10. MarchandBrustel, Y., Gual, P., Tanti, J. F., and Cormont, M. (2009) Involvement of TNF-alpha in abnormal adipocyte and muscle sortilin expression in obese mice and humans. Diabetologia 52, 932-940
11. Gustafsen, C., Kjolby, M., Nyegaard, M., Mattheisen, M., Lundhede, J., Buttensch0n, H., Mors, 0., Bentzon, J. F., Madsen, P., Nykjaer, A., and Glerup, S. (2014) The hypercholesterolemia-risk gene SORT1 facilitates PCSK9 secretion. Cell Metab. 19, 310-318
12. Kjolby, M., Andersen, 0. M., Breiderhoff, T., Fjorback, A. W., Pedersen, K. M., Madsen, P., Jansen, P., Heeren, J., Willnow, T. E., and Nykjaer, A. (2010) Sortl, encoded by the cardiovascular risk locus 1p13.3, is a regulator of hepatic lipoprotein export. Cell Metab. 12, 213-223
13. Musunuru, K., Strong, A., Frank-Kamenetsky, M. et al. (2010) From noncoding variant to phenotype via SORT1 at the 1p13 cholesterol locus. Nature 466, 714-719
14. Patel, K. M., Strong, A., Tohyama, J., Jin, X., Morales, C. R., Billheimer, J., Millar, J., Kruth, H., and Rader, D. J. (2015) Macrophage sortilin promotes LDL uptake, foam cell formation, and atherosclerosis. Circ. Res. 116, 789-796.
15. Mortensen, M. B., Kjolby, M., Gunnersen, S., Larsen, J. V., Palmfeldt, J., Falk, E., Nykjaer, A., and Bentzon, J. F. (2014) Targeting sortilin in immune cells reduces proinflammatory cytokines and atherosclerosis. J. Clin. Invest. 124, 5317-5322
16. Hu, F., Padukkavidana, T., Vwgter, C. B., Brady, 0. A., Zheng, Y., Mackenzie, I. R., Feldman, H. H., Nykjaer, A., and Strittmatter, S. M. (2010) Sortilin-mediated endocytosis determines levels of the frontotemporal dementia protein, progranulin. Neuron 68, 654-667
17. Carrasquillo, M. M., Nicholson, A. M., Finch, N. et al. (2010) Genome-wide screen identifies rs646776 near sortilin as a regulator of progranulin levels in human plasma. Am. J. Hum. Genet. 87, 890-897
18. Carlo, A. S., Gustafsen, C., Mastrobuoni, G., Nielsen, M. S., Burgert, T., Hartl, D., Rohe, M., Nykjaer, A., Herz, J., Heeren, J., Kempa, S., Petersen, C. M., and Willnow, T. E. (2013) The pro-neurotrophin receptor sortilin is a major neuronal apolipoprotein E receptor for catabolism of amyloid-F3 peptide in the brain. J. Neurosci. 33, 358-370
19. Andersson, C. H., Hansson, O., Minthon, L., Andreasen, N., Blennow, K., Zetterberg, H., Skoog, I., Wallin, A., Nilsson, S., and Kettunen, P. (2016) A Genetic Variant of the Sortilin 1 Gene is Associated with Reduced Risk of Alzheimer's Disease. J. Alzheimers Dis. 53, 1353-1363
20. Goettsch, C., Hutcheson, J. D., Aikawa, M., Iwata, H., Pham, T., Nykjaer, A., Kjolby, M., Rogers, M., Michel, T., Shibasaki, M., Hagita, S., Kramann, R., Rader, D. J., Libby, P., Singh, S. A., and Aikawa, E. (2016) Sortilin mediates vascular calcification via its recruitment into extracellular vesicles. J. Clin. Invest. 126, 1323-1336
21. Dumaresq-Doiron, K., Jules, F., and Lefrancois, S. (2013) Sortilin turnover is mediated by ubiquitination. Biochem. Biophys. Res. Commun. 433, 90-95
22. Li, J., Bi, L., Hulke, M., Li, T. (2014) Fish oil and fenofibrate prevented phosphorylation-dependent hepatic sortilin 1 degradation in Western diet-fed mice. J. Biol. Chem. 289, 22437-22449
23. McCormick, P. J., Dunnaresq-Doiron, K., Pluviose, A. S., Pichette, V., Tosato, G., and Lefrancois, S. (2008) Palmitoylation controls recycling in lysosomal sorting and trafficking. Traffic 9, 1984-1997
24. Ward, R. J., Xu, T. R., Milligan, G. (2013) GPCR oligomerization and receptor trafficking. Methods Enzymol. 521, 69-90
25. Eggert, S., Gonzalez, A. C., Thomas, C., Schilling, S., Schwarz, S. M., Tischer, C., Adam, V., Strecker, P., Schmidt, V., Willnow, T. E., Hermey, G., Pietrzik, C. U., Koo, E. H., and Kins, S. (Aug. 10, 2017) Dimerization leads to changes in APP (amyloid precursor protein) trafficking mediated by LRP1 and SorLA. Cell. Mol. Life Sci. 10.1007/s00018-017-2625-7

26. Miner, J. J., Shao, B., Wang, Y., Chichili, G. R., Liu, Z., Klopocki, A. G., Yago, T., McDaniel, J. M., Rodgers, W., Xia, L., and McEver, R. P. (2011) Cytoplasmic domain of P-selectin glycoprotein ligand-1 facilitates dimerization and export from the endoplasmic reticulum. J. Biol. Chem. 286, 9577-9586

27. Maurel, D., Kniazeff, J., Mathis, G., Trinquet, E., Pin, J. P., and Ansanay, H. (2004) Cell surface detection of membrane protein interaction with homogeneous time-resolved fluorescence resonance energy transfer technology. Anal. Biochem. 329, 253-262

28. Westergaard, U. B., Sorensen, E. S., Hermey, G., Nielsen, M. S., Nykjaer, A., Kirkegaard, K., Jacobsen, C., Gliemann, J., Madsen, P., and Petersen, C. M. (2004) Functional organization of the sortilin VpslOp domain. J. Biol. Chem. 279, 50221-50229

29. Kitago, Y., Nagae, M., Nakata, Z., Yagi-Utsumi, M., Takagi-Niidome, S., Mihara, E., Nogi, T., Kato, K., and Takagi, J. (2015) Structural basis for amyloidogenic peptide recognition by sorLA. Nat. Struct. Mol. Biol. 22, 199-206

30. Quistgaard, E. M., Madsen, P., GrOftehauge, M. K., Nissen, P., Petersen, C. M., and Thirup, S. S. (2009) Ligands bind to Sortilin in the tunnel of a ten-bladed beta-propeller domain. Nat. Struct. Mol. Biol. 16, 96-98

31. Goettsch, C., Iwata, H., Hutcheson, J. D., O'Donnell, C. J., Chapurlat, R., Cook, N. R., Aikawa, M., Szulc, P., and Aikawa, E. (2017) Serum Sortilin Associates With Aortic Calcification and Cardiovascular Risk in Men. Arterioscler. Thromb. Vasc. Biol. 37, 1005-1011

32. Ogawa, K., Ueno, T., Iwasaki, T., Kujiraoka, T., Ishihara, M., Kunimoto, S., Takayama, T., Kanai, T., Hirayama, A., and Hattori, H. (2016) Soluble sortilin is released by activated platelets and its circulating levels are associated with cardiovascular risk factors. Atherosclerosis 249, 110-115

33. Buttenschon, H. N., Demontis, D., Kaas, M., Elfving, B., MOlgaard, S., Gustafsen, C., Kaerlev, L., Petersen, C. M., BOrglum, A. D., Mors, O., and Glerup, S. (2015) Increased serum levels of sortilin are associated with depression and correlated with BDNF and VEGF. Transl. Psychiatry 5, e677

34. Massa, F., Devader, C., Beraud-Dufour, S., Brau, F., Coppola, T., and Mazella, J. (2013) Focal adhesion kinase dependent activation of the P13 kinase pathway by the functional soluble form of neurotensin receptor-3 in HT29 cells. Int. J. Biochem. Cell Biol. 45, 952-959

35. Nyborg, A. C., Ladd, T. B., Zwizinski, C. W., Lah, J. J., and Golde, T. E. (2006) Sortilin, SorCS1b, and SorLA VpslOp sorting receptors, are novel gamma-secretase substrates. Mol. Neurodegener. 1, 3

36. Kienlen-Campard, P., Tasiaux, B., Van Flees, J., Li, M., Huysseune, S., Sato, T., Fei, J. Z., Aimoto, S., Courtoy, P. J., Smith, S. O., Constantinescu, S. N., and Octave, J. N. (2008) Amyloidogenic processing but not amyloid precursor protein (APP) intracellular C-terminal domain production requires a precisely oriented APP dimer assembled by transmembrane GXXXG motifs. J. Biol. Chem. 283, 7733-7744

37. Mazella, J., Zsurger, N., Navarro, V., Chabry, J., Kaghad, M., Caput, D., Ferrara, P., Vita, N., Gully, D., Maffrand, J. P., and Vincent, J. P. (1998) The 100-kDa neurotensin receptor is gp95/sortilin, a non-G-protein-coupled receptor. J. Biol. Chem. 273, 26273-26276

38. Massa, F., Devader, C., Lacas-Gervais, S., Beraud-Dufour, S., Coppola, T., and Mazella, J. (2014) Impairment of HT29 Cancer Cells Cohesion by the Soluble Form of Neurotensin Receptor-3. Genes Cancer 5, 240-249

39. Lara-Castro, C., Luo, N., Wallace, P., Klein, R. L., and Garvey, W. T. (2006) Adiponectin multimeric complexes and the metabolic syndrome trait cluster. Diabetes 55, 249-259

40. Waki, H., Yamauchi, T., Kamon, J., Ito, Y., Uchida, S., Kita, S., Hara, K., Hada, Y., Vasseur, F., Froguel, P., Kimura, S., Nagai, R., and Kadowaki, T. (2003) Impaired multimerization of human adiponectin mutants associated with diabetes. Molecular structure and multimer formation of adiponectin. J. Biol. Chem. 278, 40352-40363

41. Li, W., Li, C., Zhou, T., Liu, X., Liu, X., Li, X., Chen, D. (2017) Role of exosomal proteins in cancer diagnosis. Mol Cancer 16, 145

42. Hutcheson, J. D., Goettsch, C., Pham, T., lwashita, M., Aikawa, M., Singh, S. A., and Aikawa, E. (2014) Enrichment of calcifying extracellular vesicles using density-based ultracentrifugation protocol. J. Extracell. Vesicles. 3, 25129.

Example 3: Sortilin Dimerization can Increase Calcification in Human Coronary Artery Smooth Muscle Cells Extracellular vesicles (EVs) play a critical role in intercellular communication and are involved in various diseases. Sortilin promotes vascular calcification via its trafficking of tissue-nonspecific alkaline phosphatase, a facilitator of calcification, to EVs. Sortilin is synthesized with a propeptide, which is cleaved in the late Golgi network to generate the mature form. The propeptide exhibits high affinity to mature sortilin and hinders ligand binding. In HEK293 cell line, sortilin dimerization was decreased by propeptide treatment, and the sortilin mutation (S316E), which inhibits propeptide binding, increased sortilin dimerization. These results suggested that sortilin dimerization have an important role in sortilin trafficking (Itoh S et al, JBC, 2018). Moreover, sortilin forms an intermolecular disulfide bond at cysteine 783 site, and loss of the intermolecular disulfide bond by mutation (C783A) cease the transport of dimerized sortilin to EVs. To further understand the role of sortilin in vascular calcification, the effects of S316E and C783A mutations of sortilin on the dimer and multimer formation in primary human coronary artery smooth muscle cells (HCASMCs), a major source of vascular calcification, was examined. Sortilin fused with His- or Flag-tag proteins were induced by adenovirus infection, and then dimer and/or multimer of sortilin in HCASMCs and HCASMCs-derived EVs were detected using non-reducing western blotting, which maintained disulfide bounds. As a result, the S316E mutant showed an increase of multimer in HCASMCs and dimer in EVs. These results indicate that an increase of sortilin trafficking to EVs, can promote calcification. Furthermore, C783A mutant showed the decrease of sortilin dimerization in HCASMCs and EVs, suggesting that a decrease of sortilin trafficking to EVs can also occur. In conclusion, formation of dimers and multimers is fundamental for sortilin trafficking in HCASMCs-cells and HCASMC-derived EVs. Inhibition of sortilin dimerization in HCASMCs and HCASMC-derived EVs can further prevent vascular calcification.

Results

Figure 11A:
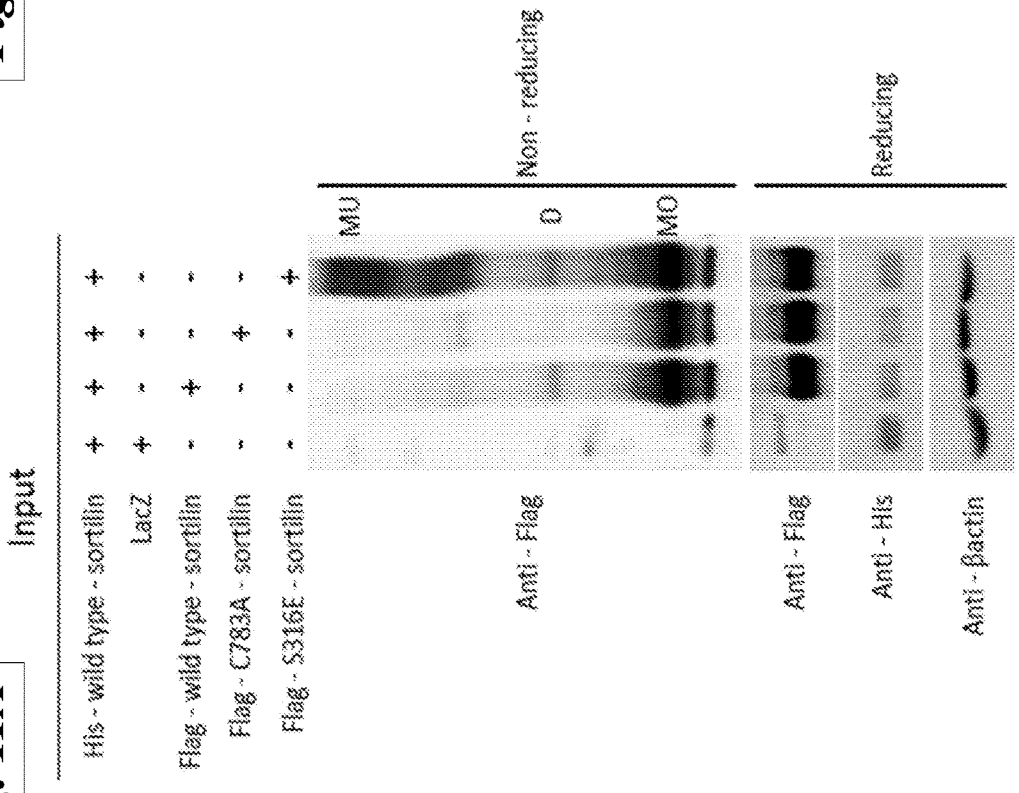
FIG. 11A-B shows HCASMCs expressing His-wild type sortilin were infected with LacZ, Flag-wild type sortilin, Flag-C783A mutant sortilin and Flag-S316E mutant sortilin.
Figure 11B:
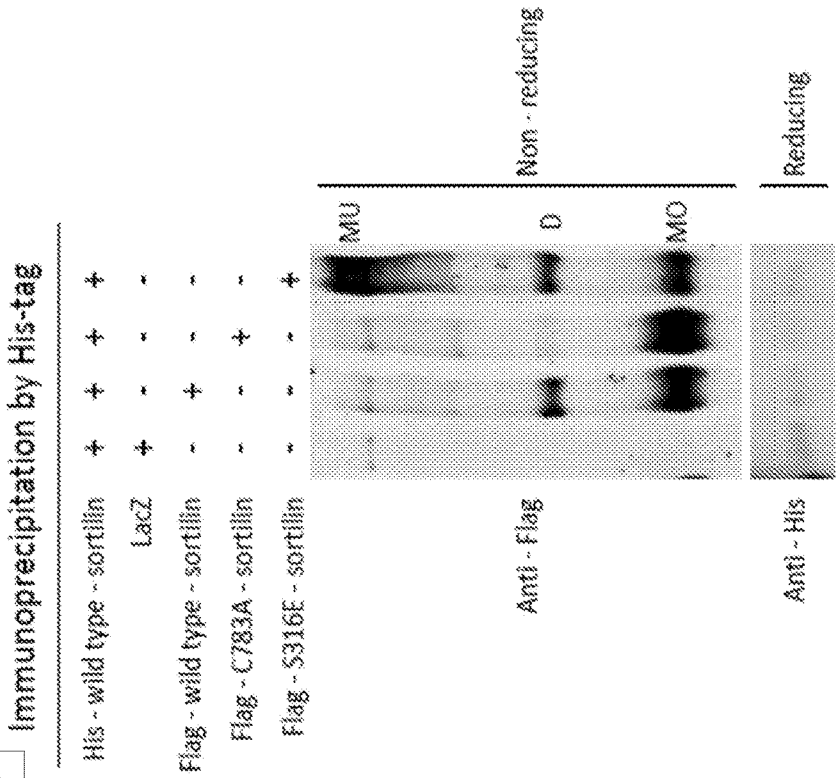

HCASMCs expressing His-wild type sortilin were infected with LacZ, Flag-wild type sortilin, Flag-C783A mutant sortilin and Flag-S316E mutant sortilin. HCASMCs were lysed 3 days after infection. Sortilin expression was detected by the non-reducing or reducing (cleavage disulfide bounds) western blotting in input sample (FIG. 11A) or immunoprecipitated sample (FIG. 11B). The results show that C783A mutant sortilin decreases dimer formation and S316E mutant increases multimer formation in HCASMC lysates (FIG. 11A-B).

Figure 12:
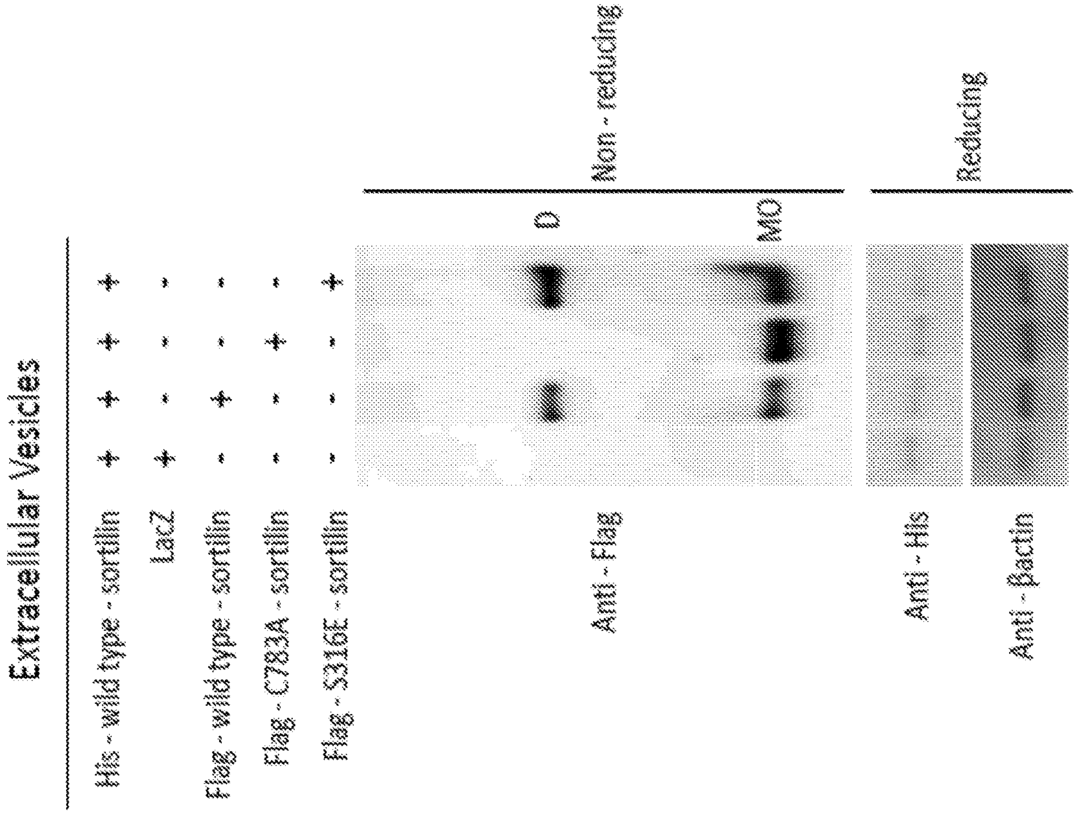
FIG. 12 shows HCASMCs expressing His-wild type sortilin were infected with LacZ, Flag-wild type sortilin, Flag-C783A mutant sortilin and Flag-S316E mutant sortilin. HCASMCs-derived EVs were isolated from culture medium 3 days after infection. Sortilin expression was detected by the non-reducing or reducing western blotting. Dimer form was decreased in C783A mutant and increased in S316E mutant. These suggest that the trafficking of sortilin to EVs is decreased in C783A mutant and increased in S316E mutant. MO=Monomer, D=dimer and MU=multimer. N=3 donors.

HCASMCs expressing His-wild type sortilin were infected with LacZ, Flag-wild type sortilin, Flag-C783A mutant sortilin and Flag-S316E mutant sortilin. HCASMCs-derived EVs were isolated from culture medium 3 days after infection. Sortilin expression was detected by the non-reducing or reducing western blotting. The results show that C783A mutant sortilin decreases dimer formation and S316E mutant increases dimer formation in HCASMCs-derived EVs (FIG. 12).

HCASMCs Culture and Adenovirus Infection

HCASMCs (PromoCell) were grown in SMC growth medium 2 (SMC-GM2, PromoCell) supplemented with epidermal growth factor (0.5 ng/ml), insulin (5 μg/ml), basic fibroblast growth factor-B (2 ng/ml) and FBS (5%). HCASMCs from 3 independent donors were used and all assays were performed at passages 8. HCASMCs were transduced with His-tagged wild type sortilin and LacZ, Flag-tagged wild type, C783A or S316E sortilin adenoviruses at MOI (multiplicity of infection) of 1000.

Methods

Immunoprecipitation:

HCASMCs were lysed with IP lysis buffer (Thermo Scientific) containing protease inhibitor (Roche). Cell lysates were incubated with Dynabeads His-Tag Isolation & Pulldown (Thermo Scientific) for 4 hours at 4° C. under rotating conditions. The bead-protein complexes were washed 3 times with IP lysis buffer. Then, precipitates were dissolved by laemmli buffer (Boston Bioproduct) for SDS-PAGE.

Isolation of HCASMCs-Derived EV from Culture Medium:

Culture medium underwent centrifugation at 1,000 rpm for 5 minutes to remove cell debris. Then, the supernatant and EVs were separated by ultracentrifugation at 100,000 g for 60 minutes at 4° C. (Beckman Coulter). EVs were lysed by IP lysis buffer.

Western Blot Analysis:

Protein was separated by SDS-PAGE and transferred by conventional wet method. Primary antibodies against Flag (Sigma, F7425), His (MBL, JM-3646) and human β-actin (Novus, #AC-15) were used. β-actin was used as loading control. Protein expression was detected using Pierce ECL Western Blotting Substrate Reagent (Thermo Scientific) and ImageQuant LAS 4000 (GE Healthcare).

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

SEQUENCES

SEQ ID NO: 1 (Sortilin full sequence-Cys783):

MERPWGAADG LSRWPHGLGL LLLLQLLPPS TLSQDRLDAP

PPPAAPLPRW SGPIGVSWGL RAAAAGGAFP RGGRWRRSAP

GEDEECGRVR DFVAKLANNT HQHVFDDLRG SVSLSWVGDS

TGVILVLTTF HVPLVIMTFG QSKLYRSEDY GKNFKDITDL

INNTFIRTEF GMAIGPENSG KVVLTAEVSG GSRGGRIFRS

SDFAKNFVQT DLPFHPLTQM MYSPQNSDYL LALSTENGLW

VSKNFGGKWE EIHKAVCLAK WGSDNTIFFT TYANGSCKAD

LGALELWRTS DLGKSFKTIG VKIYSFGLGG RFLFASVMAD

KDTTRRIHVS TDQGDTWSMA QLPSVGQEQF YSILAANDDM

VFMHVDEPGD TGFGTIFTSD DRGIVYSKSL DRHLYTTTGG

ETDFTNVTSL RGVYITSVLS EDNSIQTMIT FDQGGRWTHL

RKPENSECDA TAKNKNECSL HIHASYSISQ KLNVPMAPLS

EPNAVGIVIA HGSVGDAISV MVPDVYISDD GGYSWTKMLE

GPHYYTILDS GGIIVAIEHS SRPINVIKFS TDEGQCWQTY

TFTRDPIYFT GLASEPGARS MNISIWGFTE SFLTSQWVSY

TIDFKDILER NCEEKDYTIW LAHSTDPEDY EDGCILGYKE

QFLRLRKSSM CQNGRDYVVT KQPSICLCSL EDFLCDFGYY

RPENDSKCVE QPELKGHDLE FCLYGREEHL TTNGYRKIPG

DKCQGGVNPV REVKDLKKKC TSNFLSPEKQ NSKSNSVPII

LAIVGLMLVT VVAGVLIVKK YVCGGRFLVH RYSVLQQHAE

ANGVDGVDAL DTASHTNKSG YHDDSDEDLL E

SEQ ID NO: 2 (Sortilin propeptide):

QDRLDAPPPP AAPLPRWSGP IGVSWGLRAA AAGGAFPRGG

RWRR

SEQ ID NO: 3 (Human sortlin 1 gene: See NCBI Reference Sequence: NG_028280.1, incorporated herein by reference).

What is claimed is:

1. A method for identifying a test agent that modulates dimerization of sortilin, the method comprising:

(i) contacting a cell with a test agent, wherein the cell expresses a first sortilin polypeptide comprising a first label, and a second sortilin polypeptide comprising a second label, wherein the first and second sortilin polypeptide comprises independently the amino acid sequence of SEQ ID NO: 1; and (ii) detecting a contact level between the first and second sortilin polypeptide expressed in the cell, wherein a change in contact level relative to a control or reference level indicates the agent modulates dimerization of sortilin.

2. The method of claim 1, wherein said detecting comprises analyzing the cell contacted in step (i) using Time-Resolved Fluorescence Resonance Energy Transfer (TR-FRET), and wherein a change in FRET signal relative to a control or reference level indicates the agent modulates dimerization of sortilin.

3. The method of claim 2, wherein an increase in FRET signal relative to a control or reference level indicates the compound inhibits dimerization of sortilin.

4. The method of claim 2, wherein a decrease in FRET signal relative to a control or reference level indicates the compound increases dimerization of sortilin.

5. The method of claim 2, wherein the control or reference level is a FRET signal in a cell expressing either the first sortilin polypeptide or the second sortilin polypeptide.

6. The method of claim 2, wherein said detecting comprises contacting the cell with a first ligand and a second ligand, wherein the first ligand is capable of binding with the first label and is conjugated with a with a Fluorescence Resonance Energy Transfer (FRET) donor, and wherein the second ligand is capable of binding with the second label and is conjugated with a FRET acceptor.

7. The method of claim 6, wherein the first or second ligand is an antibody.

8. The method of claim 1, wherein the agent inhibits dimerization of sortilin.

9. The method of claim 1, wherein the agent increases dimerization of sortilin.

* * * * *

SEQUENCE LISTING

<160> NUMBER OF SEQ ID NOS: 6

<210> SEQ ID NO 1
<211> LENGTH: 831
<212> TYPE: PRT
<213> ORGANISM: Homo sapiens

<400> SEQUENCE: 1

Met Glu Arg Pro Trp Gly Ala Ala Asp Gly Leu Ser Arg Trp Pro His
1               5                   10                  15

Gly Leu Gly Leu Leu Leu Leu Leu Gln Leu Leu Pro Pro Ser Thr Leu
            20                  25                  30

Ser Gln Asp Arg Leu Asp Ala Pro Pro Pro Pro Ala Ala Pro Leu Pro
        35                  40                  45

Arg Trp Ser Gly Pro Ile Gly Val Ser Trp Gly Leu Arg Ala Ala Ala
    50                  55                  60

Ala Gly Gly Ala Phe Pro Arg Gly Gly Arg Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
            100                 105                 110

Ser Leu Ser Trp Val Gly Asp Ser Thr Gly Val Ile Leu Val Leu Thr
        115                 120                 125

Thr Phe His Val Pro Leu Val Ile Met Thr Phe Gly Gln Ser Lys Leu
    130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
            180                 185                 190

Arg Gly Gly Arg Ile Phe Arg Ser Ser Asp Phe Ala Lys Asn Phe Val
        195                 200                 205

Gln Thr Asp Leu Pro Phe His Pro Leu Thr Gln Met Met Tyr Ser Pro
    210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255

Cys Leu Ala Lys Trp Gly Ser Asp Asn Thr Ile Phe Phe Thr Thr Tyr
            260                 265                 270

Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr

```
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
    450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Met Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685

Val Glu Gln Pro Glu Leu Lys Gly His Asp Leu Glu Phe Cys Leu Tyr
    690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn Ser Val Pro Ile Ile Leu Ala Ile Val Gly Leu Met Leu
        755                 760                 765

Val Thr Val Val Ala Gly Val Leu Ile Val Lys Lys Tyr Val Cys Gly
    770                 775                 780

Gly Arg Phe Leu Val His Arg Tyr Ser Val Leu Gln Gln His Ala Glu
785                 790                 795                 800

Ala Asn Gly Val Asp Gly Val Asp Ala Leu Asp Thr Ala Ser His Thr
                805                 810                 815

Asn Lys Ser Gly Tyr His Asp Asp Ser Asp Glu Asp Leu Leu Glu
            820                 825                 830
```

-continued

<210> SEQ ID NO 2
<211> LENGTH: 44
<212> TYPE: PRT
<213> ORGANISM: Homo sapiens

<400> SEQUENCE: 2

Gln Asp Arg Leu Asp Ala Pro Pro Pro Pro Ala Ala Pro Leu Pro Arg
1               5                   10                  15

Trp Ser Gly Pro Ile Gly Val Ser Trp Gly Leu Arg Ala Ala Ala Ala
            20                  25                  30

Gly Gly Ala Phe Pro Arg Gly Gly Arg Trp Arg Arg
        35                  40

<210> SEQ ID NO 3
<211> LENGTH: 95377
<212> TYPE: DNA
<213> ORGANISM: Homo sapiens

<400> SEQUENCE: 3
cctgaggttg ggagttcgag accagcctga ccaacatgga gaatcgccgt ctctactaaa 60
aatacaaaat tagccgggtg tggtggcgca tgtctgtaat cccagctact cgagaggctg 120
aggcaggaga atcgcttgaa cccgggaggc ggaggttgcg gtgagcctag atcacgccat 180
tgcactccag cctgaacaac aagagcgaaa ctccatctca aaacaaaacc aaaaacaaac 240
aaaaaaaact tttttgttaa gttttgccac ataaacaatt ttagagaaaa tacctgacaa 300
tagttaatga ttatttgttg taggcaataa tggtctaagc actttatata tattaacatt 360
taatcctcac aactactcta tgaattagct attcttattg tcctcattgt acagatgaag 420
aaatagaggc acagagtggc caagtaacct caagtcacac acacaagctc aacttttaag 480
tatttaaata tacttcaaat atatttctaa aggagtcttt aacagaaaaa agtactgact 540
ccatgtactt tgctgctgct tttgtgatcc ctgttgaagt gacttcaaga agtgacaatg 600
atgccaggca tttggttaag tatgatgtgg tgagttaacc ttaaaataga aaatttggtc 660
aataagcatt tttattttgg agccagagag ctattttagg gacctgctgc ctggaaagga 720
tatccttggg acagcagatc ccttagttcc taatgaatag ctgcatcacc aacacagctt 780
ctcctgacca tggtagggcc atcagcaggg taactcagcc cagcttatta acccttctgt 840
tttctttcca gctagccaca gtgcagcctg gccagaattt ccacatgttc acaaaggaag 900
aacttgaaga ggttatcaag gacatttaag gaatcctgat cctcagaact tctctgggac 960
aatttcagtt ctaataatgt ccttaaattt tatttccagc tcctgttcct tggaaaatct 1020
ccattgtatg tgcatttttt aaatgatgtc tgtacataaa ggcagttctg aaataaagaa 1080
aattttaaaa tatttgttaa tagactgttc tcttctaata gtcttttttt ttttttttt 1140 tttaagagat gaggtctcac tatattgccc aggctggttt caaactcctg ggttcaagtg 1200
atcttcccgc ctctgcctcc tgaagtgcta ggattatagg cgagagccac tgtgcccagc 1260
cattgtaata cagtcttttg tttgaaatgc aaatgttagt gggccaaaag gacagtgtta 1320
ttaatatccc tattctatga agatgtctgt tctaaaactg ttttagtgat gctctataac 1380
agaatcaact atatccatta atcccatggt gttgataaat gaactagtcc agctcttccc 1440
agtggttaat agatgttaac agcactgtaa atccatttcg gccctataat ttctggagca 1500
aacgtgtatt tttgctgctt ttcttataag gagatgctac taattgacta tcagaagaac 1560
atgttttgag gtcctcctca aaacattgat gggttggaat cagccatcaa cagtgttgta 1620
ccagttcttg ggtcttgata gacaatttgg aaagagattt ccttgtttac gaagtgaagg 1680
actaagaatt aaattaatga ccttggcctc actggcaatc aattacaaat ctctatatca 1740
gtaagagaat tgtaaaattc agaagcagtt tacattagac tttggaatga atgatgaact 1800
ttccccatta gagctgccat catatgattg gtggagattg tttaaagaat cattctatct 1860
cagcctcaaa aattaccacg ggaagatggt atcagtatca ctacttaaca gatgaagaat 1920
ctaatgctgt gtgcccatgg acacacaaaa ttaagctgtt gggacttgaa cagctcaaat 1980
tttcttgttt cagatcacca gctcttgagt aatagggaaa tctggagatt tgaaaagtac 2040
ttgcactgtc cacaacatgg ctaatccata tgtggatgat gcagaattga tttaattcac 2100
taacagggac cccataatta tttgctgggc tctgggtata ttgatgtgta ggaagttgta 2160
ctatatgtta ataaattatg actatttgga taggctgaat tcatactaaa tccatactgt 2220
agttcaacaa aaaacaacat gtttatatac atttggaaac tgcaatgata ggaaacattt 2280
ggaagaaagg gattttgccc tagaataaca cataaggaaa gcagagaatt agagtatatt 2340
gttactgaat gttccagaga cttctagtga ttttaacact tattaagtat agcatgttga 2400
tggggagatt tgtttctcta aagatcactt tgttttatta aatcctaata gaaaataccc 2460
ttgaaaatcc tatctcattt attcctgtaa caaatttatt gagcacctac ctactatatg 2520
ccaagaaatg tattagccat caggcagaga gctgttcaaa tggtagatat gatctgtgct 2580
cctgtgaaac ttctagtggg gagagccaaa caataaacaa tattcctttt taactctagg 2640
ttaatgcaga aatggataaa gcccatgttg cttttgggag aggtgagttg tgtctctgaa 2700
tcacatgcat ttcatagggg gaaaaatgcc caaatactaa ggagtagctc ttagcctatg 2760
tccgttcgcc tcagcttaag ttgttttccc tcccactggc tgggcagcat atttgtgttt 2820
tacctggtaa aacagtaaat ttcgtacctt ctataattgg cattcttcaa agaggtagaa 2880
ctttgatttt tttgtagaat attaaaacaa gctttcttag gttaaagaag tgatcttact 2940
acgaacagca atggtttcat gatgtgtaat tgctttatgt tatctttctg ctatagaatg 3000
tttcctggag aaaggtacgg tttttagtaa taagataaat ttactttagt cctgcaaata 3060
aggtgaaatc ttatgtccag tatctcacaa aggagaactg acagtgccac ttttatattt 3120
aatgtcaatc tcattagaca aaaatgaaat atagttccta gggtttccaa tttaaaaagt 3180
gaaataataa atatattcac tcaaacattt tctcagtgcc atatgcaagt taccatgtcc 3240
cagaagctga tacagtttga agaaggaaat atataagtac tgtaagcctg tgataactaa 3300
aagcaacata ctaaaaagtg aaggtacaga taattggaac aaatttaata gcgtttaaaa 3360
gtgtatttgg taatttctcc aggaggtggc actgttgagt tgttttttct tttcagacag 3420
taagacaata gaccattcat ctttgtgtca cccaaacaaa gaaatattcc tttataaccc 3480
cctttcctcc ccccacctaa tcacatgcta ctggaactga ctgtcttgtg atctactccc 3540
atagttggca tagatttaaa aataatcttt tttaaattaa tctgatagta gttatggaaa 3600
ggaacaaatt gttcaccaat tttcatcagc tttatctttt cagtccagta actgagaact 3660
taaaaagact attctagtga ttttactatc ctgctcagat ggcattcaaa aacatttttc 3720
acttctcacg tcttggaaaa atttgtaaat tcgttaagtc tttttgtttg aaagttaatg 3780
tgactggaaa tattttaatg taaatatcgg gttgggtgca ttgtatcatt ttgctctaca 3840
atgactatat cctcatttgg gtttatggcc agtttataat taaaagtaat ctttacttgc 3900
tttgagtgta atgacttgca tattttgtat ctttctattt gctacctttt ctactgaaca 3960

```
atttctagct ttctgaaggg atggagtcag taagcttaag gattcagaac tggttttacc   4020
tgtgctacgt gttgtagaag ttgtgtgtgc agcttctgcg gtaaagggaa cagcgtaggg   4080
gttttatttt attcattaga ggtggatcgg ggtgctaatt tagaggacat cacatactgg   4140
aaccaaactt gtccgaagct ctcactgcag agttaaggca ctttggtaaa ataaatgtgc   4200
atctaggaaa tgatcatgtg tacagtaggc attggatcat tctcttgccc ctcttttacc   4260
tgcccctaat gcctaagcta cattcgaagt cctggaaaac ctgtaagtaa ttccgccttt   4320
ggcctacctc ccctcagaag aggaaggtga gagaggccaa acgtatggaa agactattct   4380
tcaggcttgc aggagtcacg gatgtcctga tgtctgtctc cgtaggatgt ggcccacatc   4440
agttcgcatt caccttcttg cagcaaggca gctgcttagc agacaatggg cgctccagtg   4500
agcggggttt ataaaaaccc gaagccccgg ttcatgatgg agcccccttt tccagctgag   4560
caagctcagg gatttcctgg gtaggttttt ccaggctctg cctcaccgaa ggaattttag   4620
gagtgtctct ggggaacagg agggacgtaa cccagcccca acttgagggc gctagaggtg   4680
cggcaagggg tcgcgacgcc aggagcccgg ggctcggcgg gaaggtatga gaagctccta   4740
cgtgaactcc acaagccggg cccgggagac gccgggcgag gcggggttga cctcagcagt   4800
ctctgccccg ttccagccaa tcagtcccgc atcttagcat ccgaatccag gacccccgaa   4860
gccggaggcg acgcgagcca atgaggagtg ggccggggaa gagggacagg cggccagcct   4920
atggggcgga gaggcccggc cgcgcgtatc caaggagcgc cgcgctcggc tcgggggtgt   4980
ggcgcgcgcc ggcgggggtg ggcgggcgcg ccgggcggca ggtgtcggcg tcggcggcat   5040
tcggcggcga tggagcggcc ctggggagct gcggacggcc tctcgcgctg gccccatggc   5100
ctcggcctcc tcctcctcct gcagctgctg ccgccgtcga ccctcagcca ggaccggctg   5160
gacgcgccgc cgccgcccgc tgcgccgctg ccgcgctggt ctggccccat cggggtgagc   5220
tgggggctgc gggcggccgc agccgggggc gcgtttcccc gcggcggccg ttggcgtcgc   5280
agcgcgccgg gcgaggacga ggagtgcggc cgggtccggg acttcgtcgc caagctggcc   5340
aacaacacgc accaggtgag cgggcgccgg gcccgggagc cgctcgggtg cgaggtgccg   5400
cccgcgtgcc cctcccggcc cgtgcgcccc gcgactcccg gaggagaccc cagccctgcc   5460
gcgcccgcgt cccccgggcc gcagccccga aactgcggcg ggcgggcggg cggagtcggg   5520
cccgggcggc cggcggggct gtgttttgtc ataggggagg caatcttaga cttccaccgc   5580
attctttttt ttttttttaa gttgtcaaaa tctcttgaac atcgtttttc gtctgtataa   5640
ataatcagga cccagtaacg ctgttaggcc ccaggaaggt gaaggagtaa ttaactcttg   5700
agcgcttgca gaagttgggc tgcgcagaag caaaggtgtg tcctctctgg gtcagtactt   5760
tccgggtggg agaggcggga gttcaggagg cccgaagcag cgatctggtc accgtgtttt   5820
aatagttaag gggactagct tggaaatgag atggcaatat ttatgtgatc tcttttactg   5880
cttcagattt gaccttctgt catggtacgg aagtctgact agcatgtcta tatcccgtgg   5940
tgacaagatt ttcaatagtt aagaaacgca ttgcacatat tctgctttga gccagctctt   6000
ggtcaaaaga ctttcaaaat tatgggattt ctgtccctgg ggacaagcag ctcaaccttt   6060
gcacactact ggactgacaa aactaattat taagaaagtc ctggttcctt gcttcagcac   6120
aacttgggca tctttctcct atttctctaa aattaacaat ttaatccttg ctagccacat   6180
ttgcataatg tattttcaat tctatatatt ttctcccttg cctgttttcc tctttcaaag   6240
aaaatgaatt gcacttgggg gcagagatgg gtggccaagg ctctgtgcca gcacttgtcc   6300
ttctgtaacc gtttttcagc gtcagccaag cctcagtctc cctttggact gcctggttat   6360
```

ctggaccata cttgttacct gtaatagaat tctctgatct gaggacacaa gacacaaata 6420
ttcaggaata attgtgctta gtgtatcccg agcagcagct gtgtaaaggt agccaagcta 6480
gtgctggagg gtgagacagg ttgggtagaa tgagtactgg gaagtcttcc tacttgatga 6540
gaaaaaaaaa tcgaatagac ttccttctca cagtgggga ttgagaaagg ctttacaaca 6600
ctaatgctta atttatactg gaccacttcc ttccttgagc tagctggtca cagcattctt 6660
gctccatatt tcaaattctt ctctcgctgg ttgacctaac tttaggtctg ctgctactcc 6720
tggatttaga tttactcctg tttttctttt tctcttttt tgtgagatag agtcttacct 6780
cagcctcctg agtagctggg actacaggtg tgcaccacta tgcctagcta atttttgtgt 6840
aattactatt ttttttttga gatagggtct cactctgttg cccaggctgg aatgcagtgg 6900
tgtgatcaca gctcactgca gccctgacct cctgggctca agtgatcctc tcacctcagc 6960
ctcccaagta gccgggacta ctggtacatg cacccagcta attgttcttt tctttctttc 7020
tttcttttt taagaaacag ggttttgcca tgttccccag gctggtcttg aactcctggg 7080
ctcaagtgct ccacccacct tagcctgcca cagtgctgag attagaggcg tgagccacta 7140
tgccctgcct ggatttattc cttgagtcag agtcttcctg gttagtttga attgatgtgt 7200
catttgtaat atattgattc caaagaaaga ggttgaaaaa actggctcag ggttctaag 7260
gccaaatctg tggaagagta gacctaaaac cactcattct ttgaagtcca catgtaaaga 7320
aattttcttc tatttctttc atttagctgt ttgcaataat ttttttttag tttttctctc 7380
ccagtctttt tttcagtgac cttatttaaa atagctattt tggctgggca cggtggctca 7440
tgcctgtaat cttatcaatg tgggaggcca aggcaggtgg atcacttgag gtcagaagtt 7500
caagactagc ctggccaaca tggtgaaacc ctgtctctac taaaaataca aaagttagcc 7560
agacgcggtg gcatgcgcct gtaattccag ttattctgga ggctgaggca tgacgatcac 7620
ttgaacccag gaggcagagg ttgcagcgag ccgagatcgc accgttgtac tccagcctgg 7680
gtgacagagt gagactctat ctcaaaaaaa aaaaaaaaaa aaaaaaaaaa aaagtttttg 7740
cgtttgttag tcatccgtgg tctcttcttc agagatctca tcctttctgt atctggttaa 7800
aaaaaaaaaa agtggagcct ttgtttaata tcatttacct taaaaatggt taagtagtac 7860
ttcttaacca agaattgtta tgtagtagcc tgttcttctg tttatttatt tggttttaga 7920
agtcataaaa aatcctgaac tgtattgaag agatctagta tttttggacc gtttataaaa 7980
cagtgtgaaa taaaagcatc agcatgacag aacaactttt tatcagagat attgtacttt 8040
gtacaactgg ggaaggaagg tacatgtaga atcatttttc ctacataaca tgacaggatt 8100
cgagtcccaa gaaaaagcaa aagttcatgg ttctcttatt tcttttaact tggtcctgtt 8160
tcatttcaag ccacattaat tcacatcatc aatgtatgtg aatgccctcc aaatgcctag 8220
atctgtgcta gatgctgggg tgccaagata caaagaaaag atcattcaga ctggagaatg 8280
aaaagcctca gaaggttata gcaaactact agacctgtgt ctgtggctta tgaggatata 8340
ttagcattta acctgtcttc tcaagaaagc acggtaaagc taaagcataa tagtgcgttt 8400
atattacggt ttaaggagac cggtgtcctg atgaccactc aggcttctct gtccatgaaa 8460
tccagcaggt ttttctcttt gcccaagcct ccctttttct ctctaaggtt ttttttctca 8520
tatcatttct tttcaatcta ttaatttaaa atatatttaa agtgcattgg gtttattaca 8580
cacagcatat attttttcac atagaagtcc taatgattaa gtgctttatt ttaggagttg 8640
aggcaggaga ggaaaacatt ttcctttcta gttacagtat tacaagttag ctataataga 8700

-continued

```
ctcatgggaa agtggaaata aaaaatactg gctattacta aaaaaacaaa caaaagggat   8760
gacaagaaaa cgaaggagaa agataaatag ttataacttt ccaaaaatta tgctccctaa   8820
ttttgttcta agggtttgac ttaccatggt aaggtggtat agcactgcct tatctggact   8880
gcctgcattt gaaccctggc catgtcactg tgtgatcctg ggtgagttac ttaagttttc   8940
tgtgtctcag ttcctaatct gtaaagtgaa gataagagca cttaatttgt agggtggttg   9000
tgagaattaa atgagtgtgt gttaaattat atatacataa tatatacgta tatgtatatt   9060
attgtataaa tatatatttg tattacataa tatatgcata tgtaatattg tatttgtaat   9120
gagttatagt atgtattaca acatatcaca ttgtgttgta taatctatac atatgtaata   9180
actcattaga agaatgtctg gcacataatt agcactcagc aattagctat catttataaa   9240
tgctctcttc ttagactcaa taatcttcct tttgcctgga actcaaaact gttttcatgc   9300
cacattttta actgattctt tccttcagct gcttggagta ttcatgacat gtataacctt   9360
tgtacatgcg tgaaattgag caggcctaga agactttatt gttggttact aagttggatt   9420
gcttcaaaac atttctgctg taagcacccc tttgagggta ggcatgaaac tgtcttaaag   9480
gaacagatga aatgccttgg ccagagttgt ggtggtggct gacataattt ccttacttct   9540
cattcctgtg tacagaccat ttgacaattt ccttaaaact ttttaaactt atgatgaata   9600
aagccaggaa ctcttgctta ttttctgtcc tccctctgct cctgtcacta actacttctg   9660
taaacataac ttcccaactt ctactccaac tttaaagcat ctggttcctt aaataaacag   9720
gccctgtaga gaggccgtgt tgtatggggt gtcagctctg ggaagaatgc gtgtgtttgt   9780
ttgctggctc tggcagggtt gagtccaagc tgacaggact gagtgtgcct gtcagaggct   9840
tcagggagct gccgctgaag acctcggcct gttgttgtga atcgccagac ctttgtaaca   9900
cccggaagtc tgaaggtcag tcctttaatg ccccggaact tcctaactgc ctcatttctt   9960
ccaatacttg gcctctcttc atcctacctt ccctagcacc cccagccgtc tagcttattt  10020
aatagtctct tgagttctgt ttcttccatt cagctttgga tcaaggagta ggaactctgt  10080
aggatctcct tcttggtcct ggttgagcag agtgagcgaa accttcatga agagtcttct  10140
ctcatgcaat gtatagtcag acctttagcc cctagaggga tgttaaaatg acttatgcat  10200
tggatatttc agtaagaagt atcagcagat ttgatgaagt gtaatttatc tggggaaagg  10260
ttagtcttca tctgaagttt ggttgggatg agagtagaaa gctagccagg tatgacagat  10320
ggctccaagg gaatgcagtg ttaacaatta ggtaagttct ctgctgactc aaatgtttgg  10380
ctctgtgcac agtgattttt aattagaaat ctgagtctca tgtctgcttg tggaaataat  10440
tggaagaagg cttatgttct gttcaatttc taatggctat tttctttttg tgattattaa  10500
caacaataat aggctttcta tcctgctgtt ttgatcagat ctttcatgtc agggtcacag  10560
atactattag cagtttcttc tgcactctgc cagtttccag tcaactctcg tcaacaggca  10620
ttgggttctc agtgggtgac tgcagagtct gcgttcccca actttgtccc agttggcctg  10680
ttacccttgt gtgaccatca catgctgggc agtgcttagc accaagttgt aatggtcagg  10740
acgggggagt aacgtttgtt cttctccctc cttcctacct aatcctaccc ctcaattttt  10800
tttacagaaa gtgaactatg ttttgaggct gcagaaatga ggctcagata ttttatataa  10860
ttaggagcta atattaaggc agacaaagcc atcacatttg acatgtaatt taaaatacag  10920
cttttctaga aacaacaaaa ctgtggcaat ggctctgaca atattatgaa ctagatactg  10980
catttgtaga tttctacaag tttcagttcc ctttctctcc ttttgtcatc agtgttttta  11040
ttgcatcttt tacttctatt tttaaaaact tggtgaaaac ttgttcttcc cactatgtgg  11100
```

tctcagtgat ttgtatgcag gtggatttga ggattaatgg ggcttgaaga acaagctgat 11160
caatttcagt cagttctagg cagctttttt gttcttgttt caatggtgac tgcagtcaaa 11220
gttgggttag taatatgttg ctttgagata gtttggttga atgaatgttc atgacagatt 11280
cctcatacct atgaaaattt ttaggtgaaa gatggaggct gtttttcctt ctctatcccc 11340
aatctcaatc tcaggaaacc acagtaaaaa caaaatcctt ccactcagaa cctgtcgtgt 11400
tttgccgagg aagttttctg tgaatgtaac ttattttctg ttttgtgttt tagtctctgg 11460
ccctcgattc ctcatctaca gcacaagaag ttttggacta gctttaaaat ttctttcaaa 11520
aattctatga ttcatatggg agaggccaga ggttgtgatc acaaatgttt tcctggctga 11580
ttccaaattt agaagcaaac tgtggctgtt tgacttccca gtcaaacttg aacatagcat 11640
ggatttcaca tttaggggtg ttttactacc acctccagaa cttgcttcag tgaaatatgc 11700
atgttcttaa agatagcagg agtacttttt ttcatgtagt tatgaaagac atttttctct 11760
tttattttgg gggtaatatt ttaccgtttg ttccttgttg gctgaaaaat ctaatgctaa 11820
taaaagctac tagcttgaat agtccaaaag caaacccaac agatagcagt aaattcattt 11880
ttctttttcc ctttcctata gtactctgcc aaaactgggg cttttttttct tcatcctggc 11940
tgcctgtgtg tttgaaaata gatggtcagc ttaccataaa tatattcaca tgtagaaact 12000
tatatgtgat taattggctt gatttatttt tatcagaaga aaacgtatgt atgttccttc 12060
tctggcttat gaatactatc cgtcttatgt ttgctttgga taagcatttt agtcttcctg 12120
tatgtcctaa aacgcgcgcg cgcacacaca cacacacaca cacacacaca tacacacaca 12180
cacacacact ttctaatatt gtactgaagc cagtttgcaa gtctggttcc acagtacaat 12240
tgctctgaag gaccaggaga aattgaactg ggaaggaaaa tttgtattaa cttcaataat 12300
tcccagacaa gttagttcaa atcattttta tctagtattt gctatttgtc acaaaggatt 12360
caaaacataa atatgttgta tacaaaatct caaagagatg tctcaatacc cagatttggg 12420
tcctggctct gctgcttcat agctgtgtga ttatggaaaa tcacttaact tcagtggtct 12480
ttacagttgt tttttaaact agagcagcag ctcttaggat tgtttggagg gtcaaatgag 12540
aagttttatc aacgtgtttt gttaaaggta aagtactata tagatgtcat tcatttagac 12600
acttactgag ctgcctgcca tgtactgagt ggagtccaga cctgtgcata aacaaagcaa 12660
agcactgggg ctatcttaag gatttaggtg ttcagagatg tttcactggg agtttggaag 12720
aaggcttgac cactgcagtg cagtgttctg ggaaagccct ctggctgaag agagaatcaa 12780
agtggaggtg atttttaggg agatctgtaa cggcacgaag gaagtaggaa aatccaagat 12840
atgttcaagg gatggtcaac agaaacttta ttttagggtg aggtagttga tggggagtat 12900
gactaaggtt tccaggaaaa catataggga agttaaaaaa aagatagctc ttttgtgggg 12960
gatggaaaga gaggaggggc gtgggtagtg agtttggcaa aaggacttac ttgtgaaaga 13020
gagagtttta acagatagtg ctagacatga ggctagagct ggaggaacca gaggtagaaa 13080
tggggagcca agaagagttc ccctttcaga ggccggccat tgctttggtc ttggatgtga 13140
aggtcccaga ggaaagcaga acagaaggtg aggcagacca tcctttatac ttgaagtgct 13200
aacgtttcca aaaagcactc ctaaacttct ggacctggtt gaagaagaat gtgagccaag 13260
gcatgaggaa gccaggagct gtaagacagt gatgcctatg aacagatttt tctgaacatt 13320
tgtgaacaag gataaggttg aactcttgct gataatgtgc ttaatggttt gaatcatgga 13380
ttattgggcc gattagctgg tcagagccct tttgctgatg cggctggctg acttgcttac 13440

-continued

```
tggccaagag ctgggagtag aacacagatg tcccaacatg gtgctgcatt tggaagtgtt  13500
tcataggagt gttgaaatca atgcatttgc tttagggata aggcaaagtt atgagatccc  13560
agttataagt aatatagttg tgaattctac tctttttctc aaggtcatag taccctcaac  13620
agagctcaac tagcctttct aggcctcagt ttcccgtcac ataaaatgga ggattatcat  13680
gaagttttga agggaagata tatgtgaaaa tattttgaaa ccttgaagta ccgtatgagt  13740
atgatttgta taattcctta ataaacctgc tgatgtgtca cagcccccac agggcctgct  13800
tgtcagccag gtgatcctga tagatacagc ccttgagcca aaccctgagg agcatgtgta  13860
ttaaagcaga cggatgaggc ataaatgcgt ttggtttatc acttggcaga gttggatgac  13920
aggcttgggt gggggtggca agaattaaag tgagtcaaga ttggcagaaa tgtaagacgt  13980
gtatgtagtg gttttcttct ttttttaagc ctttgtgatt atgtcaaact tttgttaata  14040
taattgatga tggtttgagg cagtagtttg ggggaacagg atctcaggta ttagatctgg  14100
attcaaactt cagtggtgac catggacaaa ttaacctctc tgaaccttag atttttcatc  14160
tatgaaatgg gagtactaat actacctctt agggtcattg tgaagatagt acaggattta  14220
gtgtatattc ttttgttgag gatttcttgt aatgattttc attacaaagc ttctgacaca  14280
ttaccagtta gatgcttaaa tatttgtaca tgtgcttaat ttttttcata tctctaatat  14340
ttctagagaa ttattatagg tactcacaag aactgcatct ggattaagac atattagccc  14400
tggctaagca gggtgactca cacctataat cccaagattt ttggagtctg aggcaagaga  14460
atcacttgag cccatgagtt tgaaaccagc ctgggcaaca tagtgagacc ccatctgtat  14520
aaaaaaattt ttttaattag cctggtatgg tagcatatgc cggtagccct agccacacaa  14580
gagtctgagg tgaggggatc acttgagccc aggagttttg aggctgtcgt gagctatgat  14640
tgcgccgctg cattccagtc tgggcaacag agcgagatac tgtcttccaa aaatacaaaa  14700
aaatttatta ggggtaggta gtggtgcaca tctagagttc cagctatttg gaaggctgag  14760
gcaggaggat agcttgagcc caggagttca aagctatagg acactgtgat cgcatctgtg  14820
aataaccact gtacgccagc ctgggcaaca tagtgaggtc ccatatctaa aaggaaaaaa  14880
aaatgtacta cttgtatcac tggactcagg atgaaaaaag aggagggtgg gagataggtt  14940
taggcagaga tcatctattc aaaatgcctt tctttctttt tctttttttt ttgagacagg  15000
gtctcgctct gttgcccagg ctggagtgca gtggcactat ctcggctcac tgcaacctcc  15060
gcctctgggg ctcaagcagt tctctgcctc agccccccaa gtagctggga ttacaggtgc  15120
ccgccaccac acccggctaa tttttgtatt tttagtagag atggggtttc accatcttgg  15180
ccaggctggt cttaaactcc tgacctcgtg atccacccac ctcggcccca aagtgttggg  15240
attgcaggcg tgagccaccg cgcccagccc aaaatgcctt tcttgaagct atgggagata  15300
gagaagaaaa taatcagatt aataatcaga aaacagtaat cagatacctg gtcatctggt  15360
tataatagct tcaagcatat atggttaaat agtttttgtt ttgttttaaa acaaaatttt  15420
aaattttaaa caaaatttaa aaatttaaga gacatggtct ttactgtgtc acccagactg  15480
gagtgcaggg gtgtaatcat ggtttgttgt aaccttgaat tcctgggctc aagtgatcct  15540
cctgcctcag cctctgcagt agctaggact acaggcacat atccctgtgc ctggctagta  15600
aataggttga aataacttaa agttatttat ttttatttat ttattttttg agactgagtc  15660
tcactgttgt cctggctgga tggagtacag tggcatgatt tcagctcact gcaacctctg  15720
cctcctgggt tcaagtgatc ctcctgcctc agcctccaaa gtagctggga ctgcagatgt  15780
gcaccaccac acctggctaa tttttgtatt tttagtagag atggggtttc accatgttgg  15840
```

```
ccaggctggt cttgaactcc tgacctcagg tgatctgcct gcctcagcct cccaaagtgc  15900
tgggattaca ggcatgagcc actgcacctg accaaattat tttttaaaga ctataattta  15960
ataacaattt ttcttcccct tcattaagct ttaatttgtt aagagttaat ggctctggtt  16020
taagttgata gctctgaaat agcaccttgc atatttcacc cctttcttta actgagcagc  16080
tgctgttagc tttgcactct actgatctct gtgaagtttc aagaaatatt agtgaaatgt  16140
gataggtact tcttaggaac tttgcttgaa agaatagcgg accagaatgt tgatggaatt  16200
atttttttatt atgtgcatat tgctttttta aacttttaac aattatttaa aaatagagat  16260
gaggtcttac tatgctgcct aggctggtct gggattcctg ggctcaagtg atccttccgc  16320
ctgggcctcc caaagtgcta ggagtatagg tgtgagccac cacacctggc ctatgtgcat  16380
atttatttaa cctactattt caccacttcc tggcctatat taaccctctg ttccagttaa  16440
agtgatcttc taaccagtcc cttcagctcc ccatatggtc tgttgcttct ccatctttgt  16500
tttcatgggt ttcttcctgt ctgaatgccc ttctagccct tgttagtttt tcctgttctc  16560
ttctataatt ttggactgtg ccatgtaata caacacttct gtcttgtgtt cagtttcatt  16620
tatagaagtt ttactcccta aatgataaac tccttaaagg tagggcccag cttgtactat  16680
gagtccttca tcacttttgc ctcccacaat gctgaagaaa gagtagtcat gaaatgtgta  16740
gtctggagtc agacagacat gagattgaaa ccttgctctg ccacttacca actttttgac  16800
tttgagcaaa ttacttaacg cctctgagcc tgctgctttc tttataaatt aacagtgagt  16860
accttaatat ataatactaa tataataagt gcttagtaaa ggttaaatat tattgttttt  16920
ctttaattca gcagttgttt gtcgagcacc tatacacatg aggcacttat caggtcctgg  16980
gaactggtgt agaacaccag acctctgcct tgatggaact ttatggacca atagagaaaa  17040
tggcactaaa tgatatataa ttataaatgt agtaattacc aagaagaaaa atagtaacca  17100
caggaataat tgacaggtct tttttagtct ggggcattag gaaagattca ctgagaaatt  17160
atttaaactg atacttgaat agaattttgc caggaagagt atctcaggca gagagaacaa  17220
catgttcata aggcctgggt ctagaaagag cttggcatac tccaggatct ggaagaaggc  17280
cagtgtggtt gtagcagagg gaatggggga aggggttagc gcccacaccc aagggagaag  17340
cagcaagcct ttatggttct ctcggctcag tcagctggca actggagcat atctctctgt  17400
cactttcttt tctttaaaat gaactaagat ataacaatta aatgcaaaaa ttatgaaatg  17460
tagctattta ttgagaaatg aattgtttca tggaagtgac tttcaaaaac taagcctacc  17520
cttttataag tgccaaaggt tttttgtttg cttgcttttt taatggaaat ctttctaata  17580
tacttctctg ccttcttggt caacagtatg agcctaggtc actaagaaga gaataaatta  17640
tgctatacca ggactgctgt ggtttgaatg tgcctcccca aattcatgtt ttaggaactt  17700
aatcgtcaat gtaacagtat taagtggtgg gtctttaaga ggtattatat catgagggca  17760
ccaactcatg aatggattaa ggcctttatc ccaggagtgg gttaattata atagggagag  17820
agtttggtcc tatttctttt ctttttgttg ttgttgttgt tgttgagaca gagtctcact  17880
ctattgtcca ggctggagtg cagtgttgtg atctcagctc actgcaacct ccgcctccca  17940
ggttcaaggg attctcgtgc ctctgcctcc caagtagctg ggattacagg tgtacgccac  18000
cacacctggc taatttttgc atttttagta gagatggggt ttcaccatgt tgcccaggct  18060
ggtttcaaac tcctgacctc aagtgatcca cctgccttgg cctcccaagt gctgcaatta  18120
caggcgtgag ctaccatgcc tggcctggtc ctatttcttt tctgtgtctc ctgtgcttgc  18180
```

ttccactttc tgccatggga tgatcctctg cagatgccta tgccatactc ttggacttca 18240
cagcctccag aactgtgagc tacataaacg tcttttcttt ataaattgcc ctgtcttgga 18300
tattctctta tagcaactga aaatggacta agacaatgac tcacagtatt ttaatgtggt 18360
atgacattta atacccacag gagctattga gatatgtggg gctatcttct cccatttcag 18420
atgtcctgga ttataaactt aatgccattg tctgcctgtt tgcttctttg ctgcagaaat 18480
gatattccct ttgtaattcc tcttgtaata tcctcttcct cttgctgttg tccctgtctg 18540
tctctacata tatcaccctc aaatttgatt tgcttcctct ctatgctgag aaagcagatt 18600
tctaatatta gacaattcta accggtttaa taaattgaat tagagtgatg gtctgcaaat 18660
ttctcttaga agtcaaatgc acagattttt aatgcatgat agtgacatca gaggtctcct 18720
tgcttctttt cggtgagtat ccgggttgct gaggcatctg aatcatggag gttgctgttg 18780
cccctctcct ttgaacactg gcttattgtg gagcagggag ctgatctcga aaacaacaaa 18840
aacccagata catagcagtt gaaaagcaaa ctgagtggct aaattattga tgagtcatag 18900
aattttaaag cttagagaga ctggaaagat tgtcattcta gcccccgcac ttcggtaatg 18960
atgtcaggtt gtgctgccca atttcacgca gcgttttgta gagctggaaa taaaatttgg 19020
gttgactgat tattagcctg gtactctcct ctgtatcatg ctccctcaga aaactctgaa 19080
taattaaata gatttggaaa cttgtacatt attttgtagt taattttttc atttccaaga 19140
atagacttca tgagaactgg gacatttgtg atcttatttc tggctcatgt tttatgattc 19200
tagcagtgcc taatttaaca gaactatatt ctgttaggat tttcttcctg cctgcaaaag 19260
catcactcag gttgtgttct aggcctcact ggagtttgga agcctaatcc tagatgggca 19320
gtctgtatgg gatcaccgat gccttgcctt tgtaattctc agttttaccc ctgaggaaat 19380
ggattcccaa cagataagat gatttgtgct taccttccca accagttagt tactgagcta 19440
ggcttaacgt tcttttgtag ttttattttc attgtgacag gctgacttct gtagattaaa 19500
agtctagtat gtttagcctt tatttttaga tttctgtaca taagatgcct gttgataggt 19560
tataatcttc agtagctcag agcatgtatt atcacagcac atggtaggca tgcagacata 19620
tttgttgaaa gagggcaggt atgtgaagaa tgccatcatt gaattcactt ccttctttgc 19680
ttgtcaaaaa ggctgctcct gatggggtca ggccatcagc aagtggcttt taagctgggc 19740
cttgccttgg gaaaactgac ccacatgcaa tagtgcaggt gttagttttt tcagtgtttt 19800
atttttgatc atgtgtgtaa ctaaacatgt aagtttctca tgactggatt tttttccaac 19860
ctacagtgac tcttgggacc aactttaaat tttccaagct tatagtaaca gtaatttaat 19920
ttggtttcta gtttaattag atgggaagat ggttgtttcc atgaagaatc ttgtgaacag 19980
aacctagggg gtattcagac gatcgtagaa atgaacattg tgctaattca tgaactctaa 20040
agtatggggg ccccctgctt taagatggta ggcaataaat gcttggatga gtcttatatc 20100
atccgttttc aaggtggatg cattttagag aaggtagtac aagctgtccc ctgctttcta 20160
acataatgaa ttcctgaaaa cctatttgac agtcagatgg caactataaa tgccagccag 20220
ttacttctgc ttcccagagc tcccctaccg agggcagtag atggctgttg gtaccatctg 20280
ggacaccaga aatcactgtt caataggtaa tggacaaaag gctctgaatg tgactctgaa 20340
aaggaagttt agtgttatca gtcattaatg atattaggag gtctacctta catcaagacc 20400
acctatgttc ctgtgcctca gtgtagcagg ggctctttga cctatcctgt aaccttctgg 20460
tatatctgtt aactagtgta atataaataa gaataaacta acatgcgtcc aggcgtggtg 20520
gttcacacct gtaatcccag cactttggga ggctgaggca gacagatcac ttgaggtcag 20580
gagtttgaaa ccatcctggc caacatggta aaaccccatc tctactaaaa atacaaaaat 20640
tagccaggca tggtggcatg cacctgtaat cttagctact gggaaggctg aggcatgaga 20700
cttgcttgaa cccagaaggt ggaggttgca gtgagctgag atcatgccat tgcactccag 20760
cctgggcaac agagtgagac tttgtcccaa aaaagaataa atagataaac tgatatggtc 20820
tatgtgtact ttttatatca ccctttcctt tatacttttt ctttccttcc tttttttttt 20880
aagtaaaaat agcttactta tatagtttta tttttaaaat gatttctgcc aattggaggt 20940
gggatgagag taatttatgc actctagaaa aactataaag aagagtgcac ccctatcaat 21000
tctataatac cacttaaaga cagttgctat tgatatttta aagggtatcc ttccagatac 21060
cttttttttt tctttttaa gggacaatct tgctctgtca tccagactag agtgcagtgg 21120
cacaatcatg gctgactgta gccttgacct cctgggctca aacagtgtat ctgggacgac 21180
aggtgcttgc caccatgcct ggctagtttt tattgttgtt gttattgttg gtttttttgga 21240
ggcaaagtct cactatgttt cccaggctgg tctcaaactc ctgagcttaa gcaattgttc 21300
tgcctcatcc tcccaaagta ctaggattat aggtgtgagc cactgtgccc ggcccctgat 21360
aacattgtaa ccataaatat gcacatatga tgtcacatgc tgttttgtag cctgcttttt 21420
actaatatgc tctgagtatc tttcaatgtc agtaaatacc tgaaacattt tagttttggg 21480
tttttaaga tttttttaaa cgtttcttct ttttttcctt gttcttgaaa catttttaat 21540
agcacctgat atattgttgt atggcataac ataatttact taacaaatct ccagttcttc 21600
atttataata tacaggtata gtaatatctc atggggttat gtggattaaa taataatgtg 21660
tgtaagatac ctaacacaga agatgacatg tggggaatgt tcaatagttg ttagctgcag 21720
taatcacccc aacatatgac atcttttata aaggtatgtg attatcccct tatgacaaat 21780
tcctaagaat aggatttgct caggcacatg atacggacgt tctcagtttt tatttgcatc 21840
accaaatagc tctccagaaa agttgcagca atttatgtac tcccacccac cgtagaagaa 21900
ggtgctctgg tccctatgcc ctcactggat acattttgtc aagtctttta atctttgcca 21960
gtctgaaagg caaaaatgtc atatttttct ttttctttct tggctcacta caacctctac 22020
ttcctgggct caaaccaccc tcccatctca gcctcctgag tagctgggac tacaggtgca 22080
caccaccata cccggctaat tttttttttt tttttttttt tttttttgt ggcgacaggg 22140
ttttgccatg ttgcccaggc tggtctcaaa ctcccaggct caagtgatcc tcccgccttg 22200
gcctcccaaa gcctgggatt acaggtgtga gccactgcac cggcctgttc tttttgtttt 22260
agagattaaa tagcttttca aatgtttatt ggccatttct ttgtccttct atgaattggg 22320
tgctcatgtt ctttccctat tttccgaaaa cctgtttgag gttttggcct gtttcctact 22380
gatttgaaaa ccctttctat attaatattt tgtcatgtta caaataattt tatattaatt 22440
gaaacccttt ctatattaat actttgtcat gttacaaata ttttttcca gttttttca 22500
gctttctctt tggtgtttg caatttaaac tttttacata gtcagagtaa atccttaagt 22560
atgagttctg atttttgtac catttttgta aaggtcttcc cattccaagg ttataaaaat 22620
attcgcttat acttctagta tcattttttg acacagggtc ccactctgtc acccaggctg 22680
gagtacagtg gtgccatcac agatcactac agcctcgaac tcccaggctc aagcaatcct 22740
cccacctcaa cctcctgagt cgctgggacc acaaactcat gctatgccac cacacctggc 22800
tattgttttt ttgtttgttt tcttttttgg tagagacagg gtctcactat gttgcccagg 22860
ctggtctcaa actcctgggc tcaagcagtc cacccacctg ggcctcccaa aatgctagga 22920
ttacaggggt gagccactgt gcctggccat ttctagtatt tttataattt aattttttta 22980
catttaaatc ttcgccctat atggaattta tttaggcatt ttaagaaggg agttaggaat 23040
tcagcttttt attttatttt ttttccaaat agccagtttt tccagtgttc ttataccact 23100
aacttgaaat gctagcttta tcatgtgcta aaagaaacct catccattcc tggatctgtt 23160
ttgctctatt gattagtcta ttcctgcgcc agtaactctg tcatgggatt aataaatttt 23220
tccaaaagtg gcaataattt catgctcatc tgctcctggt agaatcaagc tgacatttca 23280
cccagctact cttaaacttc ttggcttctg tgcttcctat cctagggtag gattaggtca 23340
tctgaatgac tgtatttgct ctgggctcct cagggtactg gcttttggac tgttaagcac 23400
agaaacagca tatttacata gttttcctta attttgacct gtttctagat catacgttta 23460
gctgactcct tagcaatatg aagtgaccag atcgtgttct ctttgtgcca aatgaagctt 23520
gtccaaccca cagcccgtgg gccacatgtg gcccagggtg gctttgaatg caacccaata 23580
caaattcgta aactttctta aaacattatg agattttttt gtatgatttt ttttttttta 23640
gctaattagc tattgttagt gttaatgtat tttatgtgtg gcccaagaca atttttctgc 23700
cagtgtgccc cagggaagcc aaaagattgg acaccccaac aatctgcctc ttaggcatgc 23760
tacattagag caacacagct attttttttt tttcttttg agacggcgtt tcactttgtc 23820
acccaggctg gagtgcagtg gcgcagtctc ggctcactgc aacctctgct tcctgggttc 23880
aagcaattct tctgcctcag cctcctcagt agctgggcct acaggtgtgt gccaccacac 23940
ccagctaatt tttgtatttt tagtagagac ggagtttcac catattggtc aggcgggtct 24000
tgaactcctg acctcaggtg atccacccgc ctcagcctcc caagatgctg ggattacagg 24060
tgtggtgtga gccatcatgc ctggcctcca gttattgttt accagaaaca aaacatgctt 24120
cacttctccc cacactctcc atttgaatta tcatttatac aactaacaca taacatcttt 24180
atatatatat atatatatat atatatatat atatatatat atatatatat atatatatat 24240
atcattcact ctaccttctg ttggctggac tctctaacat agtactagat gtttttatat 24300
gattcattat tttgatatta tagaacattc ttcggtaata ctgtgtcaga ggttttgggt 24360
tttcccttcc tatagggatt attccgcctt tcagttattt ctggcaacaa agctttatcc 24420
tctgctcata tttcatttat tcttcttact ttgccttgat tacagcaatt gagccataac 24480
ttattggctc attattttca ggcctatgta tcatcagaca cctttcctgt ctaagtgatc 24540
cagtggcctc tctcagcttt ctttgggtct ttcaagcagg agtactattt ctaaagtgtc 24600
ttcttaaata tatttccttt tcactatttt tattttcctt ctatttcaac cttaactttc 24660
tttattctga ccttgagatt cttcttatta ttattctttt aaatatagac cgggtctctc 24720
tctgttttcc agactagagt gcagtggcat gatcatagct tactgcagct tcgaattcct 24780
gggctcaagt gatcctccta cctcagcttc ctgagtagct agaactacag gtgtgtacca 24840
ccatgcctgg ctgattttta aactttttgt agcgatgggg gcggggtctc actatattgc 24900
ccaggctggt cttgaactcg tggactcaag tgacctccca cctcagcctc ccaatgtgct 24960
gggattacag gcatgaacca ccatactcag cctgaaattc ttttttttatt ttaacaagtc 25020
ttaatagcat ttactgtata ctcagcattt tactagatgg tgatattaat agattttatt 25080
tgtggtgttc tttgaaaatt ttcaagatac ttgcatatta tcttcctgtg tgttctacct 25140
gcaccgctgc cttctctcat tgccttgctc ttgcttatat ctgcctccca actctgtaaa 25200
ctctgcttaa atctcagtag tcagaccttt atttcttcac ttgaaatttg aatttctctt 25260
ctatatagac taccccctgct cagtgcctct aaacacttcg acgtgttcag ggcatcttta 25320

```
ccaatgttta gctacgtgaa gttaatggta actacaatgg gaaagagagg agtaaggtca  25380
ccatcatgtg tgaacatcta agaacacata ccagtgtata acagtgtctt ggctggctgg  25440
aagagcatag gaataaacgc tattcagcca ttatttactg agacagcagt aaccgtgtta  25500
gaaggaagat tacatacaga tcaataatgt tagttcagga caaacagcta tcatgagtta  25560
aaaaaaatac taagaaaaag aaataatgtt agtagcagga gtttgtgata gacttttaca  25620
gagatgtttg tggagcatct aataaatata agaccttgtg ctaggcctga tgggtaatac  25680
caaattatag cgtctgccat taagaattta tagcataatt tgagaggaag acaaatatgt  25740
aaatagttct acatgtatag tttacatgta catatagttt acatttatat ataaatataa  25800
atagttatag taccaggagt gtctgtgaat gctgtgagga taatgcttag gaagaggaga  25860
tcactttgag ctgtgataat tacaaaccag aatggttggt tttacagtga aagatgggac  25920
ttaggctgtc tttcagatct ttttcactgg tatagtctgt cccctgtggc tgtcaaaaag  25980
aaacacccac aatagaatgc tgaggagcaa tggacaagtg cagaaacaca gaacttttcc  26040
tttttgaaag ttgcattttt caacttttag atttaggggt acatgtgcag gtttgttacc  26100
tgggtatatt gtgcgatgct gggatacaaa tgatcccatc actcaggtag tgaacatagt  26160
acccaaaagt tagtttacca gtactcacct gcgtccctcc tctaataatc ccgtttctgt  26220
tgttgccatc tttatgtcca tgagtaccca gtgtttacct cccaatataa gtgagagcat  26280
gtggtatttg gttttctgtt tctgtgttaa tttactgagg gtaatggcct ccatgtgcat  26340
ccatgttgct gcaagggaca tgatatcatt cattttatgg ctccatagta ttacatggtg  26400
tatatagacc atattttctt tatccaatcc actgctgatg ggcacctagg ttgattccat  26460
gtctttgcta ttgtaaatag agctataatt aacatagtgc atgtgtcttt ttggtagaat  26520
gatttgtttt cttttggata tatacccagt aacaggattg ctgggtcaga tcatagttct  26580
cttttaagtt cctttttttt tttttttttt tgagatggag tctccctctg ttgcccaggc  26640
tggaatgcgg tggcgcgatc acggctcact gcaagctccg cctcccgggt tcacgccatt  26700
ctcctgcctc agcctctccg agtagctggg actacaggcg cccgccgcca cgcccggcta  26760
attttttgta tttttagtag agacggggtt tcaccgtagt ctcgatctcc tgacctcgtg  26820
atccgcccgc ctcggcctcc caaagtgctg ggattacaag cgtgagccac cacgcccggc  26880
cctttaagtt ctttgagaaa tctccaaatc gcttttcaca ggggctgaac attccctcca  26940
acagtgtata aacactccct tttctccaca gcctcaccag tatctgtttt tgtgtgtgtg  27000
tgtgtgatgt tttagtaata gtcattcttt ctagtatgag atggtatctc attgtgaaac  27060
ctgcattttt gaaaaatagt ttcacttgct atagaattac agcttgactg tttttttgcc  27120
agtactttaa atatgttact ccactgtctg gcttgcattg taggaagagt cggctatcat  27180
tctttgtttc tctgtatgta atgtcatctt ttttgtggat gcttttaaga tttttctcta  27240
ttgctgattt tagattattt gactatgata tgatgtgctt tggtgtattt ttcatcgtgt  27300
ttcttgagct tagggtttct gagcttcttg gatctctggg tttatccttt tcatcacatt  27360
tggggaaatt ttggctatta tatctttttt tttttttttt gaaacggagt ctcactgtcg  27420
cccaggctgg agtgcagtgg cgcgatctcg gctcactgca ggcaccgccc cctggggttc  27480
acgccattct cctgcctcag cctcccgcgt agctggtact acaggcgccc gccacctcgc  27540
ccggcgaatt ttttgtattt ttagtagaga cggggatggt cttgatctcc tgacctcgtg  27600
atctgcccgc cttggcctcc caaagtgctg ggattacagg cgtgagccac cgtggctatt  27660
```

atatcttaac tttttttct gtctccagcc cagcctcctc tagatgccct gattgcatat 27720
ataatcagct gcttgaagtt gttctacttc aaaaagaatg aacagagcca tcgctgagct 27780
gtagaacaac tttaagaaca tttgtagaaa ttgtagaaca tcttctgaat tgatagctct 27840
gttcattttt tgtctttttt tatctctgtg tttcactttg gatagtttct gttggtatgg 27900
cttcaggttc acactcacct cttctacagt gtctaatctc ctgttcagcc tatccagtgt 27960
ttgttttttt gtttgtttgt ttttgagacg gagtctcact ctgtcactca ggtggagttc 28020
agtcgtgcaa tcttggctca atacagcctc cacctcccag gttcaagcga ttctcctgcc 28080
tcagccttct gagtagctgg gactacaggt gtatgtcacc acgcctggct agtttttgta 28140
tttttagtag agacaagttt tcaccatgtt ggtgaggctg gtctcaaact tctgaactca 28200
ggtgatctgc ccgcctcagt ctcccaaagt gctgggatta caggcatgag ccacagcacc 28260
ctatccagtg tacttttcat ttcagtcatt gtaatactca tttctacaag tctaatttaa 28320
gtctttttct tttctttctt tctttttttt tttgagacgg tgttttcttg tcacccaagc 28380
tgtagtgcaa tggtccaatc tctgctcact gcaacctctg cctcctggat tcaagtgatt 28440
ctcctccctc agcctcttga gtagctggga ttacaggtgc ccaccaccac acttggctaa 28500
tttttagtat tttagtaatt ttcgtatttt tagtggagac gggattttac catgttggcc 28560
aggctggtct cgaactcttg acctcaagtg atccgcccac cttggcctcc caaaatgctg 28620
ggattatagg catgagccac tgggtcttta aaaaatttta agtctttaaa aaaatttttt 28680
ttctttaaca ttctcaatcc attctctaat ttcttgtgga gtacagttac aactgttgca 28740
atgtccttat ctactaatta tcttgttatt tctgagttag tttgattttt ctcttcatta 28800
tgggtcctga tttcttcttt gcgtgcctgg ttattttttaa aaatttattt taagagacag 28860
ggtcttgctc tgttgctcag gctggagtgc agtggtatga tcatagctca ctgtagcctc 28920
aaactcctgg gctcaagaga tcctcctgcc tcagcctccc aagtagcgag ggctacaagc 28980
atgtgccacc atgcctagct gatttttta aattgttttt gtggaaatgg gggtcttgct 29040
acattgccca ggctggcttt gaactcctgg cctcaagtga tcctcccacc tcggcctccc 29100
aaagggctgg gattatagac ataagctact gcacctaccc acctgatgat ttttcagttg 29160
gatattgtga gtcttagctt gttgggtgct agatattttt gtattctttt aaatattctt 29220
gaactttgtt ctggaacact ggttacttgg aaacagtttg atccttttgg gtcttgcttt 29280
taagcatttt taggcgggac cggcacagcg ttaagtctgg ggttattttt ctttaccaca 29340
gaggtaaatg tttctgagta ctctacccaa tttccttgaa ataacgaggt ttcctattat 29400
ggttgctggt aacaggaatt attcctgttc ctgtgtgagg tctgaatatt gttctctgcc 29460
gtcctttcag gtaattattt ccctggcctc aggtagtttc ctcacatgcg tgtgctgatg 29520
ggtgttcagc tgaagacttg gtggggtggc tggggaggcc ccctgctcag atctccagaa 29580 tttttttct gtgtaagtct ttcttctcta atcttctgcc ctgtgaacct ctttggcctc 29640
cccagacgat atatcagctt cctctcttca gtttaggaag aactctggac tctgcctggg 29700
tgcccctccc ctgcactgtg cctgaaattc tctccaggca gtaagccagt tagctgtagg 29760
gtcctccttg ttcagttcct tgtctttcag gaatcgtcgt cctttgtgcc tggtgtccaa 29820
tatcttggaa acagtcattt catatattct gtcgttttgg gttttttttt cttttctttt 29880
cttttttgag atggagtctt gccctgtcgc acaggctaga gtgcagtggc gcaatcttgc 29940
ctcactgcag cctccgcctc tcgggttcaa gcaattctct gcctcagcct cccgagtagc 30000
taccgcgcct ggctaatttt ttgtatcttt tttttttttt tttgagacgg agcctcgctc 30060

-continued

```
tgtcgcccag gctggagtgc agtggcgcgc tctcggctca ctgcaagctc cgcctcccag  30120
gttcacgcca ttctcctgcc tcagcctccg gagtagctgg gactacaggt gcccgccacc  30180
acgcccggct aattttttgt atctttagta gagacggggt ttcagtcgaa ctcctgacct  30240
cgtgatccgc ctgtctcggc ctcccaaagt actggggtta caggtgtgag ccaccgcgcc  30300
cggcccattc tgtgtttttg ttttgttttg ttttgttttt tattagctgt ttccggtaga  30360
aaggtaaatg tgatccctgt cactccatct tgaccagaag cagaagtcca cccagaaatg  30420
aacttttaca tttcatactc atgtctgtca tggggaagtt aagtgggcct ggccttatcc  30480
ttttacttgg gcgtcatctt tttcaaaact tcataagtag ttcttaaaga attcaatatt  30540
tattgcgtgc ccactgtgca ctatgctgtg tgttagctgc tgaaatgtat gggcttgatt  30600
cctttaccag atggacctca ggtctagtgg ggaggacagg caaggttctt gtggctacaa  30660
ttaaaagtgc tgtaatacat attttgaaag atctaagatg ccactgcagt gtagaatgac  30720
atgtacgttg tcttaaatat tagaaatgat tctggattag gattgatggc tttgtgctga  30780
cttgtgaatt ctgtctccta accatgacca ggttgtctgc cctttcctgg acatccgtat  30840
ttttttctcc cattgaagtg gcaggattga atctgtactc ttgggtccct agctctcctg  30900
gatttatctc ctttccatat gaccttttct ttctgcttaa cctttgggcc tgctgtaaca  30960
tctcatttca tttttctttt ttaactttca ccagtataag aatgttagag actgaaatat  31020
taaaaaatta attacattg ctataggtag atgagttttt cagtgagttt gcccattttc  31080
aaaagcaaat cttcattggt tatttggagt gggtgggagg gacagcttaa gggcagtaga  31140
aaaccacagt tttgctagta aatctggcct acatttccaa aggaactctt tggatgatga  31200
gtgaggtcca ttaccatttc agttgtttca gtgaagctga gagttgccgg tgacacgtga  31260
taatcctcct cattctgtag ttgagcaata ggaaaatgtg ggtaatgcca gtctgcattg  31320
actgggtcgg ctgtgtagag cattgcctga aaagtaaaag ttgcagtcct gattggctca  31380
agactgatat cttacagcct gatgaagaca accacgaatt ccagtgccat aactgatgga  31440
ctttttcttt tctcttagtt atgacaagga ccttccttgg aaagataacc tgtgtttaga  31500
tgactgtgat cttagccctt gtgatctgcc tggtgcttgt ggtagctctg gatgttcctg  31560
tttttcctga aggacctcat tgatgtcatt tcagacacta tcctcactca agagaatgtg  31620
aggttttgct atgtgtgaaa tatcatataa gacacactgc tatgtcagtt tttaagcctc  31680
tggtttcaga agctctggca gccctacttt ttctcagatg cctggcaagc ctgcatgtct  31740
gaatagccct tctttcctgc agaggctgtg agaagctctg ccgagcattt gagagttaac  31800
cattatttac ggagcaagac ctgcgtgagg cactgattgt actaacttac aaaaattgtg  31860
taagagattc ttttgacatc aaaggtactt acggtccaga ggggaaatca catacgtgaa  31920
ttcggaagcc cattcaagac tgcaagagaa aattcgaaga taaacaaaac agttcatgtt  31980
ttgagttctg tttctttaga tttctatgtg ggattggtgg cttgagtgac caagtagctg  32040
gcatcccaac catttataga catgttctat tttgaggttg agtttgtggt ttggggagga  32100
tgtgtaatca ttttcaacaa atgcttactg agtgtgcaaa gtattcctgt ggaaggcaca  32160
gggagtacca agaagtataa agttacattc cccagcttcc aaggagcttc tcatatctgg  32220
gagggcaagg catgtttaag attttaaaat cttagtaaga ttataagtct taagaaaaaa  32280
gcataatcat ccacatttat tagaaatata tactgaacta ttaaactgtc taagaaatgg  32340
ggcttgggtg gtgagcatgt ggcctggaaa agagaaggat cttcactctt tgctatatag  32400
```

-continued actctatata gtatgtaatt tctatatggt ttgaaatttt tgccaagtgc agttattacc 32460
tctttggaat ttttattttt tttatcagtt acaaaaatta tagagaacag acgattgtat 32520
taatacatat aatattaacc ttgaatatct ctatgtggta ggattatgag tgacttatct 32580
ttattatgcg ttcttataat tgtctacatc ttctttaatg aatatatatt attgtataag 32640
tagagaaagg aagtatttga aaaacaaaac ccaaaaccac ctacaatgat tattataact 32700
atattttaac atgcttacta tattttggat ataatatacc agctttccct tttttacctc 32760
cttactctca ctgcaactct agtaaggttg ttttattatt atcattatta ctattgttat 32820
taaataaaaa ggtgaaacaa aggcatttgc ttcttgcttc tgcccgttgt catttttgag 32880
tgagctagac tagaagtaaa aggaatccag ttacgaactt ttcagctata ctgtaaagga 32940
tgcccagaaa aatttaaatt atgttgattt ggttacaatt acgcctgcca gtgtgggcta 33000
tgatcttttg ttttaaagca tcctaaaaat actttgctat acctttatat ttagttctgt 33060
tggagaaagc aattagattg tcccatctcc catctcccca tctggtgcag taaagaaaac 33120
tcatctgctt ggcttacttt gtgttagaga gaatttaaat ttccaagtta tttgtgattc 33180
acattaagta gttaaatccc atccctccca aattttgtac tgggaatcca tacccacttt 33240
gtaattatga acttaattac tctgaacagt aataaagttc agatatttaa agaagccaaa 33300
gattgaagga gagtggctgt catttctaaa ttaatttttt ttccccttat agcatgtgtt 33360
tgatgatctc agaggctcag tatccttgtc ctgggttgga gatagcactg gggtaagtca 33420
tattttgagt ctgttatttc agcccagcaa gaagatgata acagatttgg ggaagggtta 33480
agcacctaat atcatttctt cctgaaactg tctttagcct caatcacaga aaacacatgt 33540
ttgcaagaca gactttcagg aagttgtagt tgtgttggtt ttgctttaga attgggaaca 33600 tctttttttgc ggggggtgg ggacggagtt tcgctcttgt tgcccaagtt ggagtgcgat 33660
ggcatgatct cagctcactg caacctccac ctcccgggtt caagcgattc tcctgcctca 33720
gcctcccaag gagctgggat tacaggcacc caccaccatg cacagctgat tttttgtatt 33780
tttagtgaag atgaggtttc accatgttgg ccaggctggt cttgaacgcc tgacctcagg 33840
tgatccacgc gcctcagcct cccaaaagtg ctgggattac aggcatgagc cactgcgcct 33900
ggccgggaac atcttctgac caccttcttc cacggtggga agatggacac cttttcagtc 33960
cttggtggct gcttagcatc aagatgagca agaagaaaga tgaaagtgct ctgtactgag 34020
aagggaagcg cacaatgctt ggggaaaccc ctatatagaa acagaaaatg tccattaaaa 34080
acatcctggc actttttcctc caaattgtat tgttcctgtg tcctttccta caggtgtgtt 34140
gagggactgt ggtgcccatg ggctcatggt tgttcatctg ttggtccctg cccctgccac 34200
aaaggaggta ctgccaggat tgggggaatg gaaggaggat cagtcagctc cttatccctc 34260
ctgatataca gctgggctcc cactaggagg acacgctgag gatacattgg cccctggtct 34320
taaatcagga cttgttgcct ggctgtctta ttatcctgct tgaacaagag caggggcaac 34380
atctcctgcc ccctggtatt ccataatgca tgtgtcatag cattgaggca catgatagtt 34440
atattagaag cctaaagaaa taaaatcttg gtgctgaaaa gcaaattgta aatttcttat 34500
tttgattaat ttttaaactt tcagtagaat ttctttaagc atagttcagt tttttctaaa 34560
atttgagttg taccctaatt tccatgattt acccatttat cttagatagt tggtatctcc 34620
aagaattttt tttttttttt tttttttgga gacagagtct tgctctgtca cccaggctgg 34680
agagcagtgg tgcaatcttg gctcacagca acgtccacct cccaggttca agcaattctc 34740
atgcctcagc ctcccaagaa gctgggacta caggcaagca ccaccacgcc cggctaattt 34800
ttgtatttta agtagagatg gggtttcacc atgttagcca ggctagtctc gaacttctga 34860
cctcaagtga tccgtccgcc tcagcctccc aaagtgctgt gattacaggc gtgagccacc 34920
gtgcccagcc atctccaaga tttctcatat ggctttctga gactccctag actcttatag 34980
taatccatcc agaatcattt cctcatgcat agtttttggt agataaggta ctgaaaaaat 35040
gaatttcatg aagaaccaac ggcaaggaga agaaaaagac agacatacat gacacagtga 35100
tctctgtgag aacacccacg ctattctaga ctctgtaagg agaaaaggga agagggttct 35160
tgcctgagag tatcttacaa taatttggat acaaaatagt taaagccttc ttttatttta 35220
atgtgtattt gagtagtcag cctcactgct tcaatggagg caatggggat catcccaaca 35280
aaatgagctg aggactttct catcattctc agccctagta actagatcct tctagacttt 35340
ggggagtact acaaagtagg gatatcaaaa gtcttttagg tgttggctta atctcgaaca 35400
catatcagca tgtgattgga atatcttttt tatttacgga atgctttttt ctctctccag 35460
gtcattctag tcttgactac cttccatgta ccactggtaa ttatgacttt tggacagtcc 35520
aagctatatc gaaggtgaga tcaataacac gcgttggagc atttcactaa gtaacattga 35580
gaatatagat tctccctttt ctagacatga tggcacgtaa cagttgatgt aaaagatctt 35640
ctagccatcc taagttttca ccagactgtc acactcagca catgtttttg ttgttgttgt 35700
tgttgttgtt ttttgagaca gggtctcact cttgtcaccc aggctggagt gcagtggcgt 35760
catcttggct cactgcagcc tccacctccc aggctcaagc catcctccca cttcagcctc 35820
ccaggtagct gggactgcag gcacacgcta ccatgcccag ctaatttttt gtattttttg 35880
tagagacagg gtttccccat gttgcctagg cttgtattga gctcctgggt tcgaatgatc 35940
cacctgcctc caaaagtgct gggattatag gcgggagcca ctgcacccgg cccttagcac 36000
actttttaac gtctactctt tttttttttt tgagcagggt ctagctctgt cactcaggct 36060
ggagagcagt ggcgcaaaca cagctcattg caacctctcc ctcccaggct caagccatcc 36120
accatcttcc cacctcagcc tcccaagtgg ctggcattac aggcacgtac ctccatgcct 36180
gggtaatttt tgtattttgg atagacaggg tttcaccatg ttgcccagtc tggtatcgag 36240
cgcctgggct caagctgtct tcccacctca gcctcccaaa gtgctaggat tacaggtgtg 36300
agccaccatg cctggcctta gcatctaatt agcaactgaa agaagtatga aaagggacct 36360
ggttccaagg aggttggttt gacctgactc aggggcagaa caataaagga agatgaagaa 36420
agagtgtata gtgctgtgtg tttgtgttca tttatatgga tatttatttg tgggaaggta 36480
gtatggggtt taaaaagtct ttctatttag tgtgagtaca aaatggtttt ttatattcct 36540
gaaatgaaaa tcttcattgt actttcccag caaatattta tacagcattt tgaggcctaa 36600
gcagattatt tttaggtaag aaggaggctc tcaggtcgga cctaccaaag tgctttgtag 36660
tgttcacact ggcgatgatg gtggtaacat gtgttctgga accacaacct atactgtgac 36720
attggtgaag ttttagagtt gtcttctcaa aggtatgact tggttaaaaa gtaggttccg 36780
ttccttagca gtaagattca agaccaacta actcctagag attgctgaat gattgtgtct 36840
tctcaatcat ttatgtctgt ctcattttcc cctagagacc taaagaagta atgacatacc 36900
agcagatgat atagaaacta ccctagggtc agggtatctc ccaggagtaa tggtactttc 36960
tcaaggttct ttatttgact gctgttcttg gcccaagtgg gagtgaaccc atgttcaagc 37020
tctgaaatgg attagcctaa cctctcttcc ccgtgaggta tgaactttga ctacatctcc 37080
tgggcatgga gccagaggtc tctgcccttc aatacattga tgttggtccc agagaggcag 37140

-continued

```
caaatacctt taggccaaca aggaattgcc atctaactac agtgtaaatt ccatgaaggc  37200
aaggttcttg actaactggg gtccccagga tctagccaaa tgcctaacat atagtaggca  37260
ggcagcaaat aataattgaa taaatgaatg aatgtcttgg cttctttata atttttagat  37320
ggttaattaa attttttaa atataggatt gactatattt tagaatcttg gtgctagaaa  37380
gcgctatagt aggtgacttt gtttattcaa tcagaacagt agttgaacca ttttagatga  37440
aaaacatcct atttggggag agaaaaatgc attttaaaat gtgtaacttt gcttcagtaa  37500
ctctttcctg tggttaagaa tgtttgctat tataaattcc ctcctcacaa aattagctgg  37560
gcatggtgtc acacacctgt ggtcccagct acttgggaga ctgaggtagg agcatctctt  37620
gggtccggga ggttgaggct gcagtagcta tgatcacatc actgcactcc aggctgggtg  37680
acagagcaat accctttctc aaaaacataa aatatctcct catgatagtt tttcttacca  37740
acctgtgttt cattataaaa gcagtataat catattatag gacatttgaa aattttaaag  37800
gaaagaaaaa agttcaccat acagccacgt gtaatcttaa tttgtttgca gtttattatc  37860
ttgaccttcc cctttgatgt tgtatcatat aattgtagag tattgggagg caatgtggaa  37920
tagcaaaatg ttgccaagct ttgttggcaa gtaggctcag gattgaatca cagcactgtc  37980
attgcaaaca gaatgaactt gggaaagtca tttaacctcc taagtctttt ttgtcatctg  38040
taaaaggaca ataataatgc ccacctcaga gccgttgtga ggtatgctct gcagtgcctg  38100
gcatggagta atagcttggt gctgttagtt gctgccatgc caatgatcag ggatggcatg  38160
tagccagcag gtactggcat tgctgtacca gttgttaaaa tgaatttgaa gccttcaggc  38220
agattgcctg cccccagatg cctccacgtc ttctacaaat gcacactgca ccccctagcc  38280
cctgccaaca tgcaaatgtt actaacacct ggcattatga cctacatcca tgctgatggg  38340
tcggtactca taccttcact ctgctggtaa cccctcattt ttttagattg acataattta  38400
cttaatcatt gttccattgg atagttaggt tgtagctgtt tttttcgctg taactaatac  38460
tactgtgatc agtatcatac atatttgtgt catagggat gtttatttct agttcactct  38520
tcagtagcaa aggaaaacct ccactctgat ggatgtcaac gtgttttaaa ggctgtttgt  38580
taaatgcctc tttctctagg ttgagttatc ttctatacct aatgcctcaa caacttaaga  38640
caatcaaaac caaaacaaga accaatactg ccatgtcact gtttaaatac caccaccatc  38700
agactcagcc tttttcagc ctgtttttgt ctagtcttgt gaaaaacccc gctttcctga  38760
catactttac tagagtgcaa ttctatttgt ttctgatata gtataatgtt accaaggtac  38820
ttttttttca tgttacccag cagtttttg tttcttttt tgtttgttta accacattga  38880
ctttgaatat taattatctc ttccctgcca tgaagtggaa actgactctg tacccacttc  38940
cagagtttag gcggaaactg taaatatgcc ttgttgcctt tccaactggg ctggcctggc  39000
ttaaagtgac tggccaacca agtcaaccat gtcaaacatg ccaaccaaga ggcaactgtt  39060
gtttcagaaa tgagaaaggg aaagaagcag tttgatcaaa atgggtcctg agtatgctga  39120
agttgcccaa ttaccgataa aagcccattg aacccactct gaagattttt ctgtttttca  39180
cagcattggt gattatatta ttcgttagac catcttcgca tactaaatct tatatggtta  39240
aaggttcatt tggatttgaa ataaaaaaca gcaaatcaca tgccacctgc tctgtgtatt  39300
acagcatgaa gtctcacaag aatagaagga agttgtctct gttgatatac agaattagag  39360
ggagtatact tctgtcttta ggccatgaaa aagaattatt gaaggatttg ggagattata  39420
tgtatgtgta tgtatgtata tgtgtgtata catatgtttc tgtatacata tgtttgtgtg  39480
tatgtacatg catacacaca catatgcata ttttccattt aagggaatca tatttgtata  39540
```

gtataaattt tgatttcctt ataaggaata ttagttttat aatggattat agagtatgtt 39600
tgtctctcac ttgcacatat gaagttaaag aaataaacta gctacaatta agatgataat 39660
ttgatttttg gcaactaaaa gatattttcc atctttttgt tttatgatgt cttgagtcca 39720
acttttcatt gtataatgta cttagtgaag caaatgtagg cattattcta caccaatgtt 39780
atatacctaa ttattaatat cacaaagact gctgggctat tttattcctg gtgtttctat 39840
tgagaattgc tcaaatttcc ctattaagag gttttgcatt aaaatatatt acatagtcaa 39900
tgtaagtttt tcagaatgtt acttgagatt tttttaaaag gataacttaa aggtatacaa 39960
tgcaaagtgc tgctagtgca gtaaaccagc ttcttcaagg catgttgtgt aacaaccttt 40020
ttaatgatat gctcagttca gttttcactg cagtagattg ttaacaatga ctgcatattt 40080
cagttacaag gttgggataa attccattta caacatatat tttcttgctt tttttttttt 40140
aaagaaaaag tatattaaaa tgtgatgatg gcattttacc tttaatacaa cttcacttct 40200
atacacgtaa agttgtcaat cagagtaaga tgaagaccca caaatacata ttcatgttcc 40260
ttctgattaa aagttctgtg attttttat ttacaatatc ttactctctt tattttccca 40320
cttgtagttt caaaatttct acagaaaaca tgtatccttt cccaataatg ataaaacaca 40380
acatagttaa ataaaaacac aaggtaatat cagacagtgg gggaaaaaga cactgaaata 40440
ttgggaatta agtttattat gaattcaaat cttgccaata ttacccagca gtagtttcag 40500
gtccatgatt attttgatac attttaataa actacattct ccctattgat cttttacctg 40560
gaaatctcag tgcagttggt tgtcattatt agtgatagtt atgttctgta aagttgtcat 40620
gaatattgaa ttagttaata gtgaaccatt gctcctaggg ggacatatag ggttaggttt 40680
ctgcaaactt ctggtcacag cactcatttt catcaaatga tcaatacata actttgtttt 40740
atgtgtgttt ctgtttaaag ataccttatt taatgtgtat tattgattca ttaacactga 40800
attcatggcc aatagcacta gaactcttgc ccaaacaagg cttgtctcat atactcgtat 40860
ttcctccatg aggcacatca aagtcttctt gtgtttagga acactaaaca gcttgttgac 40920
actgctcttg gaggctattt aaacagaaaa agtacccccc aaaaaaagca taaacttgca 40980
aaaacctaag tagaaaaaaa ctaagtagac cgtaaaaagg acacttattt atagtattag 41040
aactgaacac aaaggcaaag catcaccttg tttgacctca gctgggaatg ggtacactgg 41100
gtgactcaca tttttgctgc tctatgaatg tctataaatg actggcaagg gaccatgagt 41160
actgatttgg ggattacaaa taaatttaag aaggtaaaca aatttacaaa tatagaatcc 41220
atgaataatg aagattgtat aagctttctc aattagtaaa aaccacaaaa caataatatt 41280
tttaagagtt taccatcatc cttgttactt ttatgttata atttatagtg gcttagtcat 41340
ggcaaaatga acaaaagaaa atgggtagaa gcagaaagag tttttgaggt gcatgcttga 41400
aaaagcctac atagctgtta atgaaactta aagatgattc tggtgaaggc tcagaaagaa 41460
aagaggaggg ctgtagagaa aaattccatc ttagagaata cctaagtaat ccatggtaga 41520
atattcgtaa aaatgtggac cacaaaggcc attatgatgg gtttctggca gaaatgagga 41580
acttgttgtt ggacagtaga gaaaaagcaa tccttgttat aaagtggcag acaactaggc 41640
tgaattgtgt tcatgttcta gtgttttgtg gaaagtagaa cttgcaagca atgaaattgc 41700
atatttagct aaaacaatat ctaagtaaaa tgttgaagtt gcagcttggt tcctcctgac 41760
tgctcgtagt aaaatgtggg aaaagagaaa tgacttaaag acagaattat taagcaagaa 41820
gaaagcagta ctaaaagatt tggaaaattc tcagtctatc taaattgcac agactgcaat 41880
aataggatgt gaataattag gatgtggcca agtgaccatt tgataaagag attagcatag 41940
gtgtaaacta agaactcaat cagtcacccc aacaggaaaa ctgccagttt gaacccaatg 42000
agggaaggct ttcagatttc aaggaccaca gagctattca gttgcgtatg tgtaatcttc 42060
tttaagacaa ggccattcag ggatcaccaa ggctgcctcc tcaatttcaa aagaagggac 42120
catcacccaa agccatggga gaagggccac ccagatcctt gtgggcctac cccctttctg 42180
gcaaggctgc agagcaagaa cacaatccca gcgtgtctgg gaagaggagg gaccccctcc 42240
ccaatattgg acctgtagga cagagcatag agccaaagag aattgttttc aagctttaat 42300
atctaggcca ggcgcagtgg ctcatacttg taatcccagc actttgggag gctgaggtgg 42360
aaggattgct tggggccagg agttttgaga ccagcctggg caacatagtg agacccatct 42420
ctaccaaaaa aaaaaaaaaa aaaaaattga gtgtggtggt acatgactgt agtcctagct 42480
acttgggagg ctaaggcaga agaattgctt gagctcagga gttctaggct atagtgagct 42540
atgatctcat cattgcaccc cagcctgggt ggcagagcaa gaccctctcc ttatttattt 42600
acttttgaca cagggtctta cactgttgcc caggctggag tgcagtgtca tgatcacggc 42660
tcattgtagc tttgagctcc tgggctcaag tgatcctcct gcctcagcct cccaagtggc 42720
tgggactaca ggctggaaac caccatgctc aactaaattt tgtatacttt gtagagatgg 42780
gttttcacta tgttgccttt gggaggccga ggtgggagga tgcccagcct taagacctac 42840
tctttaaaaa taactaaata aatatatctc atgaagtttg cctgtatttt agacttattt 42900
ggagtcacct ttcgtctttt ccatttccct tttttggaat ggaaatgtct atactgtgcc 42960
tgtcccacca ttgtattttg gaagtgcata acttgtttgg tttcacaggt acacaactga 43020
ggagcagttt gcttcaagat gaatcatacc ttgagtctca cctttgtctg atatagatga 43080
tatttagatg acactttcaa ttttagactt tagagttgat gctggaacaa gttaagactt 43140
taggccagat gcggtaactc atgcctgtaa tccctgcact ttgggaggca gatgtgggaa 43200
gattacctga ggtcaggagt tcgagaccag cctggccaac atggagaaac cctgtctcta 43260
ctaaaaatac aaaaattagc tgggtgtggt ggcacatacc tgtaatccca gctacttggg 43320
aggctgaggc aggagaaccg cttgaacctg ggagacagag gttgcagtga gccgagatca 43380
tgccattgca ctccagcctg ggtaacaaga gtggaactct gtctcaaaaa aataaaataa 43440
aataaaaagg cttttgaggc tgctgggatg taatgaatgt attttgcatg tgagaaggac 43500
atgagtttgg aggaatggag tggaggggca gggtgggggt gtcaggatgc cgtacactga 43560
atgtttatgt tccctctgaa ctcatatgtt gaaattttaa cccctagtgc gatggtatta 43620
ggaggtggga ccttcggtaa gtgattaggt cataagggca gaaccttcac cagtgggatt 43680
agtcccctta taagagagac cccgagagct cccttgcccc ttctgtcatg tacggttaca 43740
gtgacaagag ggtaatctgt gaagcaggaa gcagaccctc accagacagc acatctgctg 43800
gcaccttcat cttggacttc tcagcctcca gaacagtgag aaatgaattt ctgctgttta 43860
taagccaccc agtttataat attcttttat agcagcccta gctaaaataa gctctattcc 43920
aaatatattt gtattttagc attattttct tgagttataa acatgtgcat gtttacaccg 43980
tggatacatg caaaaatgat catttatttt tggtaaccag aaaatggata ttagtgttga 44040
tgcatagaat tgttattaaa aagacttgtt tcttttttttt ttttttttta agacggagtc 44100
tcactctgtc gcccaggctg cagtgcagtg gcacgatctc ggctcactgc aacctctgcc 44160
tcccggggtc aagcaattct ctgcctcagc ctcctgagta gcagggattt caggcgcgtg 44220
ccaccatgcc tggctaattt ttgtgttttt agtagagaca gggtttcacc atcttggcca 44280

```
ggctggtctt gaactcctga ccttgtgatc cacctgcctt ggcctcccaa agtgctggga  44340
ttacaggcat gagccaccac gcccggccaa aaagacttgt ttctaaagca gttggtttca  44400
cagcatttta actgtttact tatcattcga cggctgttca taacgctatt aattatcata  44460
tggaatttga aaattagatt tatcaaagtt gcttcatcaa tttcctcttc gtgacatagg  44520
ctgatagaaa ataaagtgct aggatcacgc ctctaattct agagctttgg gaggccaagg  44580
tgggaagatt gcttgaggcc aggagtttga gaccatacat atcttcatga tatgtatgct  44640
gatagaaaat aaagctacat ttaaataaag cattatgtta aaaaatatac ccctgggccc  44700
aaagtggcct tgctagaacc ctacttaagt cccagcaggt tgatactagt tcattttctc  44760
catttattta actgactaaa gtaccagagt gctgtagcag gtgatttttt gttttgctca  44820
tgctggtttc ttttttgaa gggcagggat gtgtttgttg tgccaagttc ttaaaaagca  44880
agcaggcttg ccaacaggtt tgtggagatt ctctggggat gtcatgaagg aggaccaatt  44940
tgtaaactag tactaatcag gctgcttcaa cccctttgga agatttacag agctgttgat  45000
gatacatgca ctgtagagct gggaattgtt tatgcacatc tcttggccag ctgtcaggaa  45060
gataagagct gatctactgc aaagccaaag aaagggtaat ataatatagg actctgttgg  45120
gtggcgccca attgtatttc atttatctag gaattttctg tgtgtgtgta tgtacttaag  45180
gaaggataga gtcattcaga caacttagac atatgtagtt tgtttcagca tattatcagg  45240
gacctctaca tacacacatg gatacttccc ttctgtctcc aactttctct tagctgatct  45300
cttctgccag gtcataagcc cccagcaaga cagaggaaga ccccagtttg taagggaaaa  45360
aatcctcaca gataattaaa agttatctcc agtttagggc taaaggttca gagaattgga  45420
ctatagtttc aattttgccc ttaattaact agttgacttt tgataaattg ccttcccttg  45480
caactcctca tctgtgaaat gagggagttg gacaagatgt tcacttcagc cccttacact  45540
gctcatggtt ctgcaattct ttatttgttg aggccgctac caaaacctgt aacatcattt  45600
acatcatgta cattcaagct tcgcttaatg atggggatac attctgcgaa gtgcatcatt  45660
aggtgatttc attattgtgc aaacatcaca gagtgtactt actcacacct ggacagtata  45720
gcctgctaca caccacagct atatggtata acttcttgtt cctaggcaac aaacctgtag  45780
agcatgttac tgtactgaat actgtaggca gctgtaacac agtactaagt atctgtatat  45840
ttaaacatag aaaaggcatg gtaacaatat ggtttcataa tctggactca ccatcatata  45900
aacagtccat tggtaaccaa aacatcttca tgcaacacat aactatattc tatcattgaa  45960
gaccactgca gattacattt atctgtgtgc agaaatttgc agtgcacagc agtcttcatt  46020
gatggatact taaatttaat gaacattaag atttagcatt ttgtattgtg taagagagct  46080
atacatagta ttaaacctgt cagggttaga cagctatgga atttttgctt ttattttcca  46140
gaatctaaac atggattcga atacttctca aagatattgt tggaatgaac ttttggaaaa  46200
agcttggaaa ctctgagagt tgagattaag tttgtttgtt tttcctagct gtatttcatg  46260
tactgagtgc cttacagact tctgcctagg gatggtaact tctatgggga aaaacttcaa  46320
gaacttgcta cagcttcatt tacagctttt tcataactac tgtggattaa tagattagtt  46380
agaagccttt gggagcactt tgcatagatc tcaccttaaa ctaacctgaa taataaggga  46440
atagttgatt ctgtaactaa gtacagagga atgacaggct tcagggtcga ttcaattcag  46500
tgtcataggc tctgcttctc ggtattctga aattaccttc tctgtgctcc cattgtgaca  46560
gaatgacgat agcagtcttt actgtgtgtt cacatactgc atcattgggg tttctcaacc  46620
```

```
ttagtactct tgacattggg gccaggtaat tctttattat tgtgggactg tcctgtgcct  46680
tgtaggatgt ttggcaacat cgctggccac tacccactta atgccagtag cacctcagcc  46740
cttcattgtg ataatcaaaa atgtctgtag gaccgggcac agtggctcat gcctgtaatc  46800
ccagcacttt gggaggccga ggcgggcgga tcactttgag cttgggagtc aagaccagcc  46860
tgagcaatgt ggtgaaaccc cgtctctact taaaatacaa aaattagcca ggcgtggtga  46920
cacggacctg taattccagc tactcgggag gctgaggctg gagaatcact tgagcctggg  46980
aattgcacca ctgagctgag attgcatcac tgcactccag cctgggtaac agagtgtgat  47040
cttgtctcaa aggaaaaaaa aaaagtctgc aaacattacc aaatgtttct tgggggacaa  47100
aagcaccctg attgagaact gctggtctga aggaatatag accattttat caggtagcta  47160
tcataagtgg gaggcagtgt gcttcctaga agaccccaaa tttcccaccc accttttatc  47220
tcccattggc tcatcctgag tcactccccg attcctgaac ccccatcact ggtgagtggg  47280
tttgtggggg ggggggcggg tggaatgttc ttcggactca ccagggcacc tctggagcta  47340
ggaatgtggc tattcagggt gagccgagtc tctcagcatg attggtggaa agggagaatg  47400
aaagctgagt aggaactcag taatatccat gaccactgca ccctaaattt gccctttttt  47460
tcttcctctc agtgaggatt atgggaagaa ctttaaggat attacagatc tcatcaataa  47520
cacctttatt cggactgaat ttggcatggc tattggtcct gagaactctg gaaaggtgag  47580
actcattctt gtatacataa agcttgtgct tgataccaca tgcagagctg tcagatatta  47640
gtattggcat ggtccagtga ttcacagtaa tgtattttag tttagtattg ctatatttat  47700
atttaaaaat taaacacaat tttttaaggg tctcactctg tctcccaggc tggagtgcag  47760
tgataccgtc acggctcgct gcagccttga ccttccaggc tcaagggatc ctcccacctc  47820
agtcacttga gtagctggga ctacaggctc ttgccaccac tcctgggtaa tttttgtatt  47880
tttttgtaga gggttttgcc atgttgctca ggctggtctt gaactcctgg gctcaagcaa  47940
tccacccacc tcagcccctg aagtgctggg attacaggca tgagccactg tgcctgcctt  48000
aaacacaatt taatatcgat catataagaa tggaactctg agcacacagg tttatttgtt  48060
tttgttcccc gcccaaggtg caccaaagcc cttaataatt atgcagcagt tgcttaacat  48120
tacaatgtat ataacctatg acaacatttt agttttttgg aaaactaatc tcagttagcc  48180
taatctaggc ttaaacccac agatatgatg tcccagctca gttcagggtg ttattttttt  48240
ataagaataa gacccaaggg gtagagtgga acaactaatc agtttttata actcttctta  48300
tttctagaac taaaatttct taactaatgt ctggtgaaaa tggtgtaaga actcctgtgc  48360
ttgcatagat agtatcatac cctgaatcag atctttcctc ttcctatcag gtggtgttaa  48420
cagcagaggt gtctggagga agtcgtggag gaagaatctt tagatcatca gattttgcga  48480
agaattttgt gcaaacagat ctccctttttc atcctctcac tcagatgatg tatagccctc  48540
agaattctga ttatctttta gctctcagca ctgaagtaag tccagttgag gaacatggtt  48600
tgccttttgc attttatagt ctcaaatgta ctgtcttaga aggatccttt aggaaatgct  48660
tttaatattg gacttctttc aagtctcctt atggcatgaa gtatgtattt ttttgacgtt  48720
ttttcctatt tggtaaagga cacgatttcc acatgctatc tattccaggt aagtgtgatg  48780
cctagttgtc actgtaattt ttttaagtga ctaaatgtat ggtattggag taatgaacta  48840
gaaaacagtt taatttaatc attcttgtgc tacaagggac aagcataaat tgtcaaactc  48900
ctgatgttgt cattgttcct tttctatgat caaacaacat ctttctaatt tttttctttt  48960
ttgttatgtc ctcagtttat aaaacatact gatttctgtc tttgaccctc atgtattaaa  49020
```

```
tatccaaagt cttaaatccc tgcgctccct accacgttcc tatactttcc ccagagacca  49080
gtgtgtttcc ctaaccctcc cacttctcaa agttctctga ggaacacatt cagcttctcc  49140
tttcctggag gaccagtctc ctttactgtg gttaagggcc caaagtggct gagttgctag  49200
actataataa tcagaattat actttacatt tttatggcct tctctcatca gatagaaaca  49260
cctgaggagc tagttcaaga ggcacatccc tttgcccaaa cccagatata ataaatcaat  49320
gactactgtt gtggggtggc taatattttt agcaggctcc ccagctgagc ctgagcacca  49380
aagtttgaga gtcattgctg tactgactgt tttggggtcc aaaacaagat catcaaccgt  49440
gaacaagtca ggctgagcaa aggatgacat aggaggacga agggcactgg aagagaggtc  49500
tgggttctgg gctttctgtg gggagatttt tgagcagagg tgaggctgag gggcaccagg  49560
agggccagag ttatgttttt tttgcttttg tttttttttt tttttttttt tttgagacag  49620
agttttgctc ttcttgccca ggctggagtg caatggctca atctggtctc actgcaacct  49680
ccgcctcccg ggtacaagtg cttctcctgc ctcagcctcc agagtagctg agattacagg  49740
catgtgcacc caggcccagc taattttttt gtatttttag tagagacagg gtttcaccat  49800
gttggccagg ctggtctcga actcctgacc tcaggtgatc tgcccgcctc agcctcccaa  49860
agtgctggga ttacaggtgt gagccactgt gtccggcctc agagttagcc tagcagtgga  49920
ggccagagga aggaaactag cttgctgggg agtaagcttc agatcttaga acaacaattc  49980
ctggaaattg gcctccagcc gcttaagctg aaagcactat aagggagcaa ggagtgaaca  50040
gacccataga gctccccttt gactactgca tcttccttac caagtgtctc agggttatta  50100
aaacagcact gtcctcagga agagacagat acagtctgct tctgtacctg aaatttcttc  50160
catttaaggg taaatctgaa gtacatataa ttgggatgga gaagagggac caatttgtac  50220
taaagtgcaa atcagtggta tcaaattctg ccttgtcttt ataagtagaa ttaggtaaat  50280
tagaaatgct aggatgtgag tattaccagg ggagaaaaag ttagaggaga atggtgggtg  50340
agagtacagg agtactgaac ataaattctg cctaaataag ttacatttaa tttcagctag  50400
actaggacat ctctgtccca tctccactga ggcggagctc agtaagctca cattgccggt  50460
gtaatgttgt cagtcagaat tttgttaagt ctctgctaca tttcaaacta ttggccaatc  50520
cctccttttg agaactctaa ttgtttggct tctgtgacat tattcctttt agttccttcc  50580
ttaacctcct ttcagcctac ccttaaatgc ctactcctca tttcactgag cattctcttc  50640
cactcttacc atttagctac caccacctat aatgtataag attttcaaat ccttatctct  50700
agccctggct ttcccctaat gcatcatatt cctgtcttgc tgccccctga atatctctag  50760
ctggatgttc cacaagcacc ttaaatcaat ttaaaactga gcttcctccc tactcttctc  50820
tcagacctga tcttcttccc ttaatcctta tactagttaa tgatatcaca atgcatccta  50880
taccccaacc aggaaactag agtgaccaac ttacatgcat gtgcatgcac gtgcgtacac  50940
acacacacac acacacacac acacacacac acacacccct acctctcatc ctgccctgca  51000
ggagaagtca tcccgttcta ctatgctagc ttctaaattc ttgcagagcc tgttcctcat  51060
ggccagtgtt caagacctca ttagctctta ccgaactaat gtggcagtca ttccctgctt  51120
ttccttgcct ctagtctgga ccctctgaaa tccatctttc ccattcacgt ccaagtactc  51180
cacctaagaa agtgaaacgg actgtgtcat cctcctgctt agcacacatt cctcctgaga  51240
gcacctcata tgcaataaac cctggagtcc ttaccatggc acagaaggaa ggctctctgt  51300
gagctggcct cacctttctg cctagcgtta gttcctcatt tgcttacctt ggaatttgca  51360
```

```
ctcaggtaat gcctgatggc ttttagctcc ctgcacacac tgcagggttt atgacctcct  51420
tgcgtttgct aatactagtc tctctttgtg cagcaacacc tcatctccct gtttgccttc  51480
ttttggtccc actgctcatc atttaaaact cagtgcacct gtcttcttca ggacaccatc  51540
tctgatgcaa tgttcctcct ctcctcactt ctatactaga ccatatttta taactctgca  51600
tagtgttgaa ctttcttctt atctatgcgc cttgttaaac tgtgagcccc ttctctcagc  51660
agggagtgtg tcttattcat ctttgtatcc ccagtgcaac atctggtaca gtgcctggca  51720
cataataggc acttcatacg catttgttat tctgaacttc caagacccca aaagggccca  51780
gataaactac gtgtgtgtct gtggagctcg ggcagctctg atggagcttc agtatgtgtt  51840
tttcctgtcc tgaatgattg gatatgaaat attaaaggtc atacaagcaa ctacacagga  51900
taaagctaga attttgataa gtcatttata atctttcaga atggcctgtg ggtgtccaag  51960
aattttgggg gaaaatggga agaaatccac aaagcagtat gtttggccaa atggtgagta  52020
acagaagact ccatctgtgc agagccctaa acccttcctg atagcgctgc caaaaatcac  52080
atgaataaat attgagcact tactgtgtgc caagtactct tcagggtgcc ataagagata  52140
ttggagaggg gtgtgacaca ggccttgacc tggaggagct tctcattctg ctggaaaaga  52200
agacttagtc tcacttaaat gttagaacat aaagtataaa acaaggcagg tgactgagtt  52260
gctgctgcct gcccagggtt cattctccat gaatggtgac atcaattaaa atacaataaa  52320
atatagcttt aatttaggga tttaaatact tctccatgcc cagatttacc ctcttgtcta  52380
gagttccatt tcagtcatgt agaacatggc aaggaatcag gaagaaagct gaaagagctt  52440
ccagactcct gaagtcacat tgcgcaccac aactcattca cttttctcgg agagattccc  52500
tgcccctccg ggtgcctgct taaagaggat ggagtggagg gagctcttac ttgggagtct  52560
cgtcaccttt gttctgtcct cactctgctg ctagtcaggg gctcaacctt tctgggcttt  52620
agttttttcc ttttgtgaaa ggaggcttat ttggagaatg tggggatggc taagcaagaa  52680
ctgaattaac aggcttcatg cctccaaaat ctgattaggc tcagaatgtt gtttagagcc  52740
tctttctcct ttccctttga ctaatttcag ctaatttgtg aatcccagtt tatagcagat  52800
tggttacaga ggtaggatat gtaactgctg caataagcac gtaacagcat tagaattaca  52860
gcctgagagc tggaaggagg tggaattact ctaaaagagc agacaaaaac ttagagaata  52920
aacagtatta aattatttag tgctagatca agaaagtaca cctgtgttag taacttctaa  52980
tgggaacact gtgttatagt ttgatagaat tgatgttcat gatgatgacc cacaatccca  53040
agagtttcct gtactctagg aatcaggaaa gtgtagaata cagatttgaa atatgtctac  53100
caagattgat taaaatatta aatatattgc ttaaataaag taggcctttt ctagaaatgt  53160
tcttgttctt gagatagggt attgctcttt tgtccaggct agagtacagt ggcacaggca  53220
tggcttacca cagccttgac ctcctggact taagtgatcc ttctgcctca gcctcccaag  53280
tagctgggac tacaggcatg tgccaccatg cctagctaat tttgtattt ttattttgta  53340
gagatagggg gtctcactat gttgcccagg ctggtctcaa actcctgtgc taaagcaatc  53400
cttcctcctc agcctcccag agtactggga ttataggtat gggctaccat gcctagcccc  53460
agaaatgttt ttttaatgag gtttttatag caccactctg ttacacatgc cacatttgct  53520
ttcgttttat gtattctaat gaattgtatt tgtaccttat acagttttat caggaaggaa  53580
ggaatttttt ttttcttgag acggagtctt gctctgttgc ccaggctggg gtgctgtggt  53640
gcaatctcgg ctcactgcag tctccacctc ccaggttcaa gtgattctcc tgcctcagcc  53700
tcctgagtag ctgggattac aggcatgtgc caccacaccc agctaacttt tgtattttta  53760
```

gtagcaatgg ggtttcacca tgttggccaa gctggtctca aactcctgac ctcctgatcc 53820
gcccacctca gcctcccaaa agtgctggga ttacagggca tgagccaccg taccaggtgg 53880
aagtaatttt taagataact aagttaaatt gtttcactcc tgatggaact aaaacatgta 53940
ggtcatgtgt aaataatttt tttttctttt tttaagataa ggcctggctc tgtcacccag 54000
gctgggatgt agtggcacga tctctgctca ttgcagcctc tgcctcctgg gctcaagtga 54060
tcctcgcact tcagccttcc cagtcgctgg aactacaggc atacacctgg ctaagttttg 54120
ttaaatttta atcattaaaa ctcatcttta gccaagtgca gtggctcata cccctaatcc 54180
aagcactttg ggaggctgag atggaaggat tgcttgagac caggaattca agaccagcct 54240
gggcaacaga gtgagacccc atctctacaa aaaattaatg aaaaaaaaag ccaagcatgg 54300
tggtgcacac ctgtagtcct cgttactcaa gagaatgaga tgggaggatc actttagccg 54360
aggagttcga ggctgcagtg agctgtgatt gcaccactgc actccaaact aggtgacaga 54420
gcaagactcc gtcacttaaa taaacaaaca aaaccttatc tttaaaacta aaaagttatt 54480
ttaaaatagg attttgtttt gtatcctatg caaggttttt acttttgtaa catgtttttt 54540
tttttttgtt tagtgtctaa atatgaataa ccaggatgct gctgtttact caccttttta 54600
gatctctagt ttctaggaat ttacaaccaa aagttctgaa agaacatgct caaaaccaac 54660
accttttttt ggttgcaatc cagtaagtgc caggagggtc tgaatctagt tccctgcaaa 54720
ctccctttcc aggttacatt ttaaataatt caacctccga cctagttgtc catttgagat 54780
ggaagaacta aattatttaa ctcatacaaa gcattgaact agattctgaa gggaaacagc 54840
aaagtatagt acctgccctg aagaagctaa tttatatagt aggaaaggta aggcatatac 54900
tatgcaagta aaataaaaaa caggcaaatg catgccaagt ggctgtgcag atggtacagt 54960
gctctaaaac agagtttctc aacctcagca ctaatgacat tttggatcaa agaattcttt 55020
attgtggagg accgtcctgt gcatcataaa atgtgtagca acatccctgg cctctacccg 55080
gtagatgcca ataacacctc cgccacccac ccctcagttg tgatgatcaa aaatgtcaga 55140
ggcaaatgtt gagagggtga gtagaccagc atgactgcct gaaagagttc acgtaaagaa 55200
gtggtggact gtagacaaca catgggccgg gcagtgggga gcttgacagg cagagctgtg 55260
aaggaccagg gctcagcgcc tgagaagtgg tgcttgtcag tgcctgtgaa tgaagcttgt 55320
tagacctgct aggaagtttg tgagtaaggt caacacagtc cttcagcagt cttaaaccat 55380
ttcttttccc tgtttttgcc tcattgtagg ggatcagaca acaccatctt ctttacaacc 55440
tatgcaaatg gctcctgcag taagtatatt ttagtcccag aaaataatgt cctgttgtcc 55500
attcatggta gaattttctg ggttgtgcaa ggtagaaaca taaaaggtcc ctccattctc 55560
ctgaaattgt aatagctaaa gaaagctgtt agtggttatt aaaatcttga aagtaaaacc 55620
aaattactac actacccaga tcaagtaaaa atataggcta tacgtagagg caatatttaa 55680
tcttagcaat gtatttatgt aaagcaaata ttatgctaca gacaatagca aattgaaatg 55740
catggttatt tctacaggaa agcaagggtt gtgtttgtgt ttgcagaagc agctggcttc 55800
ccaaactctg acacaacttc aaaacagaaa gcaaaatctt tcatttactc attcaacaga 55860
tatttgagca cctgctcata tgctaaacac tgttctaagg atggagagaa gaaaacaccc 55920
aaggcctgcc ctcatggaac gtaaattcag gaaaaccaaa actccagctg ggcatgatgg 55980
ttgcatgcct gcagtcccag ctacttggga ggctgagaca gcaggattgc ttgagcccag 56040
aagttcaagg acagcttggg caatgtggca agacccccag cccttaaaag aaaagaaaag 56100

```
aaaactcaag acaatttaaa ataggataag ataattccaa actgtgccat gaagaaagta  56160
aagcagcatg ctgtggcttt tttttttttt tttttttgag acggagtctt gctctgtcgc  56220
ccaggctgga gtgcagtggc gccatctccg ctcactgcaa gctccgcctc ctgggtttac  56280
accattctcc tgcctcagcc tcctgtgtag ctgggactac agacgcctgt caccacgccc  56340
ggctaatttt ttgtattttt agtagagatg gggtttcacc gtgttagcca gggtggtctt  56400
gaactcctga cctcgtgatc cacccggctc ggcctcccaa agtgctggga ttacaggcgt  56460
gagccaccgc acccgtctgc tgtggctttg atgtttttat gaaacactgt attagaatta  56520
agtaatctct tacctttcca ttgagcataa aatctgaaat gtataaaata aaacacaaat  56580
atgaattgcc tatatctaat gctgtatcac tttttttttt tttttttatg agacggagtc  56640
ttgctctgtc atacaggctg gagcacagtg gcgcgatctc tgcccactga aaactctgca  56700
tcccgggttc acgccattct cctgcctcag cctcccgagt agctgggact acaggcgccc  56760
accaccacgc ctggctaaat ttttttgtat ttttagtaca gatggggttt catggtgtta  56820
gccagtttgg tctctatctc ctgacctcgt gatccgccca cctcagcctc ccaaagtgct  56880
gggattacag gcatgagcca ctgcgcctgg ccgctgtatc acattttatg ttgtcacttg  56940
attaacatgc atagtattta aaatgcttta gctataaaat taagattgat tctaaaacaa  57000
ctgctttgaa ctaggctcac cagtaagtga aattttaatt aatattttgt cttgtttaag  57060
aagctgacct tggggctctg gaattatgga gaacttcaga cttgggaaaa agcttcaaaa  57120
ctattggtgt gaaaatctac tcatttggtc ttgggggacg tttccttttt gcctctgtga  57180
tggctgataa ggtaggtatt gccctctccc ctttggggtc tgatatttct gcaaatatct  57240
ctcgtataga ttctctttat tacttggcat tgacagagtt tcttgtcttt ttgttatatt  57300
tagtaccact gtgagtgtta ggggtgattc tttttgcaaa ggctgattga ctgataggct  57360
actctgcact ttggccttct gtcaccatgt gaattctgtt atcttttttg ggattttttt  57420
tttttttgaa acaaagtctc tctctgttgc ctaggctgga gtgcagtgac gcaatctcgg  57480
ctcactgcac cctccgcctc ccagattaaa gcaattcacc tgcctcaacc tcccaagtaa  57540
gtgggactat aggtgtgcac caccacaccc ggataatttt tgtattttta gtagagatgg  57600
ggttttgcca tgttggccgg gctggtcttg aactcctgag ctcaggtgat ccccccgcct  57660
cagcctccca aagtgctggg attataggcg tgagccaccg cgcccggcca ggatattttg  57720
atccagtgtt tgggcattac tcagacaatg gacatctgta gaaagcaatc tcttgctcat  57780
tatccaagaa taaaaataca attagataac attaattgag tgcctactat atgctaggta  57840
ctattctaag tcccaggaat atggcagtga acaaaacaga tgaatttcct gctctcagaa  57900
cttatgttta agggggaaaa taaatactca aaaaataaat atgaaggctg ggggtagtgg  57960
ctcacacttg taatctcagg actttgggag gctgaggcgg gtggatccct tgagcccagg  58020
aattcaagac cagcctgggc aacatgacaa aaccctgtct ctacaaaaaa taagaaaatt  58080
agccaggcat ggtggcatgt gcctgtagtc tcagctactt gggaggctga ggtgggagga  58140
tcatctgagc ctggggaggt tgaggctgca gtgagctgtg atcatgccac tgcattccag  58200
cctgggtaac agcacaagac cctgtctcat aaataaatat aaatgtgagt gtgtgtgtat  58260
caggtaataa ttaaagccgc gaagaaatct aaaacagtaa gaaaacaaag tgtcaggagt  58320
cagtgctctt ttagacagac tgtttaggat gggctctctg agacctaagt gaaacaagaa  58380
cttgaccatg tggccatctg ggaggagagt aggatgaggc acagccagtg cagagaccct  58440
cagactggag catgcccgat caatccaagc aaaggggaga agggcagtat ggggggagca  58500
```

cagagaataa tagtccaaag tggggccaga gggggcctgg ccagacctta tgtggccttt 58560
gtagatcaca attaggatgt gggccttact cttcttgtgt tgggagctgt gagagggttg 58620
tgagcagggg aatgctgaga tttggcttct cttttgaaga ataggtgtgc gcagaacagc 58680
ctgacagggg cacgcgcaga agcagcggga gcgccgggag ctctctcagg agtccaagct 58740
ggggaggtgg tagcttggcc aggctcttgg cagtgggtaa gggggcaggt ggtgagactg 58800
tggatacatt tttaaacata ttactaatag gacttgctga tggatttgat gtgggttgtg 58860
agagaatgag tggaatcaag ggtaccttta agagtctgta tcctgagcgc ctgaatggtg 58920
gtgccatttt ctaggatggc aaagactgca ggaggagcag gttgtgggag aaaaatcaag 58980
aattctgttt tgggccgagc atggtggctc acgccttaat cccagccctt taggaggcta 59040
agacgagcaa atcacttgag gtcaggagtt tgagagcagc ctggccaaca tggcgaaacc 59100
ctgtctctac taaaagatac aaaaaattag ccaagcgtgg tggcgcaggc ctgtaatccc 59160
agctactcgg gaggctgatg cacaagaatc aactggactg tggagacgga ggttgcagtg 59220
agccaagatc atgccactgc actccagcct gggaaacaga gtgagactct gtctcaaaaa 59280
aaataaaaaa agaattcagt tctgcatatg agacacctat tagatatctg aatggagatg 59340
tcaagtgagc atttgggtat atgaatctcc ctaattgcta tggtatttga agccatgtga 59400
ccagatgata ccttctggag gagtaagtag gtagcaaaga ggtgggagga ctgagcaagc 59460
cctgaagcac ccacaactga aaggttggaa agagaagaat ccagcaaaga agactgagag 59520
ggagggatcc gggaggaaga gggaaatcag gaccattgag ttaggtgcat tctgagaatt 59580
atccactgga gttggcgacg tggaggttgt tggtgacctt gacaaaagca cttcattgga 59640
agttaaaagg ccgattggag tgacttcagt gagaactaga gatgaagaag taggcagtaa 59700
atacagataa ctctccaaag ccattttgta atatcctccc aataaccctg tgagctaata 59760
gtattacctc agttttatag gtgaggaaat tgagtaactt acctagggtc aaccagtagt 59820
ggaatcctgc tggaaatcag actcaaattc cagaggtagc ttcctatgct atactgcata 59880
tatggtataa tgctgtctac agaattaaaa ttttgcgatg tacttttgaa ctctggtttc 59940
tacctacagt aatgagaata agattcaaag taatgagaca tgttggtata agttgaataa 60000
gttaaatgta cttatcactg aactttaaag agtatttaat ctaaggaaac accgacatta 60060
attctcatgc tcaggctaac tgtatctagt agcgatgtta agctatttat cagagagtta 60120
agttttaatt gctttcttaa cagactcttt tcgtcagcca aatactccct aatcagtttc 60180
cttatagtaa tttccgactc tccttggcct ctttccagcc catgcctgtt cccttcatcc 60240
tggctattct gagagacttc cttagagaga aggcgtgtta catcttgact tcccttgtga 60300
tctcccaaac atgggtttca tctctatttt ctagaccctt aagtatataa ttctttaaat 60360
tatgcaagca ctgtatgaaa gggaccaaac ttttatgcag tagtcatcat tttaagaatt 60420
acctgagtgt atgcaaatgg ctataaagcc aacctaatgt tctcatcaaa tccttagctc 60480
tactgaagga ggtggactat cagagaccaa gactatacta tcttacaggg ccgcatcaga 60540
atgaagaatt caaagagaaa gccaagatag ccttacttag aatagaatgg attgttcctt 60600
tacctagaac tttgctaggg gctagaaatt gctttggtaa ttggtactat gacctttcat 60660
tcatagcaat cgtacccagt agagaaatgg ataatagtag ttatttaaaa cattcttgtt 60720
catgtccctg cccatggcat cttggcagaa aattagaaag ataaatattg acatctgttc 60780
taggatacaa caagaaggat ccacgtttca acagatcaag ggacacatg gagcatggcc 60840

-continued

```
cagctcccct ccgtgggaca ggaacagttc tattctattc tggcagcaaa tgatgacatg  60900
gtattcatgc atgtagatga acctggaggt aagagctttt tagtggctta cccttaaaag  60960
catagagatg taagctttga gcagctttta tttttacatg tcgagttttc ctcttacccc  61020
tagaaattta ttagtgccct actgattttt ctgtcctaga gatcatctgt agcccctgtt  61080
aaaaatgcca cttgttttgg tagcttgtgt gtatgttcag gtgttctaga gcagagctgc  61140
tcaaagaatg gtcagcagac tggtactgat ttgcaaacta tctgttacca gataagtaca  61200
gaaattgaga gcaagagttt ggaaactctt ctagcctttt gacaaagcaa ttttatgtct  61260
gttggatcta atgacaaaaa attaggggtt tatggctggg cgcagtggct cacacctgta  61320
atcctggcac tttgggaggc tgaggcgggc agatcacgag gtcaggagat cgagaccgtc  61380
atggctaaca cagtgaaacc ccatctctac tacaaaaaat acaaaaaatt agctggccgt  61440
ggtggcgagc acctatagtc ccagctactc aggaggctga ggcaggagaa tggcatgaac  61500
ccgggaggtg gagcttgcag tgagctgaga tcgtgccact gcactccagc ctgggcaaca  61560
gagcgagact ccatctcaaa aaaaaaaaac ttaggggcat atattttgtt taccttttca  61620
ttttctaatg attagttttt attatgtttt acaatagcat cagtttgtga catattggaa  61680
atcttacaaa ttgatccttc actacagata gtttgagaag cattgttcta gagtgtaaag  61740
atttaaaaat atgtaaacta aacatagggc ctctcccacc aaaatatatc tgggaagagt  61800
ttttctgtag catctgatta atttattcaa caaactcagc atctgccata ttccaggcac  61860
taagctgggt actagaatta aagatgggca taaagatctt gagtatcaaa ccttgattaa  61920
ttctcaggtc tgagtcttca tcatgaagag acacaattgg ctactgtgtt tggtcaggca  61980
ggtaatcgtg tgtggttaga ctattgtttt tctctttggt tccacccaag acttagtatt  62040
tttgtttgtt tgcctatttc agacactggg tttggcacaa tctttacctc agatgatcga  62100
ggcattgtct attccaagtc tttggaccga catctctaca ctaccacagg cggagagacg  62160
gactttacca acgtgacctc cctccgcggc gtctacataa caagcgtgct ctccgaaggt  62220
gagtctcggc atcgcagtgg tgtactgtgc cttcagctgc atgtggtagg atttgaggct  62280
tcggggaacc tgtcccctag taatgttgct tgccaagcca acaagcctac ccatgtacat  62340
tttttgttt cctttttttt ttttattgtg gcaatatgtc taacaaaatt tgcagttttt  62400
aacattgtat agggtacaat tcagtagcat taagcacagt cacaatgttg cacaaccatc  62460
acccctattt ccagagcttt ttcatcatcc caaatagaaa ttgcaccagg tgcacaagca  62520
ctcctcgttc cccacccagt cacccagctc tggtaaccaa cattctattt tatgtctcaa  62580
tgaatttgcc tattctaggt agctcatgta agcagaatca tacactattg gttgttgtat  62640
gtctggcttc tttcatttg catattgttt caaagttcag ccacattgca gcatgtttta  62700
gaatttcact tattgctttt taagactaga atatattcct ttgtttgaat atagcacctt  62760
ttttttcttt ttctttcttt tttttttttt tttttgagat ggaatcgctc tgttgcccag  62820
actggagtgc ggtggcgtga tctcagctca ctgcaacctt ggtctcccaa gttcaaggga  62880
ttctcctgcc tcagcctcct gagtagctgg gtttacaggt gtgtgccacc acacccagct  62940
aatttttgta tttttagtag agatggggtt tcaccatgtt ggccaggttg gtctcgagct  63000
cctgacctca ggtgatctgc ctgccttggc ctcccaaagt gctgggattc caggcgtgag  63060
ccaccatgcc cagcctgttt tttattcctc cattgatgga cacttaggct gtttccattt  63120
tcagctctta tgaatactga atgctgccat gaacattgtt atacatgtaa ctgtttaagt  63180
caatgctttc agttcctttg gggatatatg taggagtgaa atagcaggat cacatgataa  63240
```

-continued ttccatgttt ctcttttgga ggaaatacca atgggttttc cacatggttg taccatttta 63300
catgcaatac aaaaggattc caatttctct acttcattgc aaacacatta tattctccta 63360
tttttgtaac agcactccta atgggagtga aatactatct cgtttatagc tttgatttgc 63420
atttctctaa tgactaaaga tgttgaacaa ctttttatat gctcgttggc catgtgaata 63480
tcttcgttga ggaagcttct aattgagtcc tatggatggc agtgattttt aaagttgtgt 63540
tcactgatgc tcctctggtg cttatgacaa tttttgcaca tagtagatgt tcagtaatac 63600
ttgccaaatg agcctacaaa taaacggctg aacagccttg cactcaaaac catacagtga 63660
acacacttga aaaacattta agactgagcc ttaagtatga taggcaggaa tggggaggga 63720
agggcatttt cagctgaagg aagtacacat gcaaagtatc agagtcgctg ggcgcggtgg 63780
ctcacacctg taatcccagc actttgggag gctgaggcag gtggatcatg aggtcaggag 63840
atcgagacca tcctggctaa cacggcgaaa ccccgtctct actaaaaata caaaaaatta 63900
gctgggcgtg gtggtggaca cctgtagtcc cagctactca ggagactgag gcaggagaat 63960
ggcgtgaacc cgggaggctg agcttgcagt gagccaagac catgccactg cactccagcc 64020
tgggcaacag agtgagactg catctcaaaa aaaaaaaaag tatcagagtc acaggagggt 64080
ttggcctggt ggtggtggtg agacattggg tgatgccggg ggaggaggga tcaggaggac 64140
agtccagcag ggacagacca aacccatgca aattcaggct ccctatttta aataagttat 64200
gataaataga actaggagtg aggagagcaa caacaagtag aaaaaaagat gttttgaatc 64260
tatgttgttt aggtaataaa gtgagtcttc tatattggga gatgtaggcc tatgagaata 64320
agcctgaatt tgacccactt cctgctcttc ttggtaaggg tgcatagcag tagccagcca 64380
gggttcttct tgtgttctac tcaatggctc tacagagctc acctttcctt aggcccagtt 64440
atacaaataa acacattagt ctcaagtaca aagactctta aagtgtcatt ttatttatat 64500
atttattttt cggtaggagg taggggctgt ttttattttg taaagtcctg gcagtggcct 64560
acaaagtcct ggagatatgg ctcccggttt cctccctgac tcacctccag cgcttctctt 64620
tccatctgcc ctactctcat catactgtcc acctgccagt tcttaacaca gcaggtacac 64680
atgcacatgc acagattaga gtttgcaccg acagttccct ctgtttctcc agatgtccgc 64740
aaggctgata tgtctgtact catgtattac tttttgaatg agaccttccc tgactatcct 64800
attttaaatt ccagtttgcc ctcgcctcct cacacacaca ctatcaatcc acctttagct 64860
gcgcaagtat tttccatagt acttattttc tagcatacta cataatttac ttatttacta 64920
tgtctagtgc ttgtctcgcc ctaccggaat gtatttttca caatatttgt ctgtttagtt 64980
cactgataca ttaccaaagg cttacaaaag ttttcactct gggtgtagtg gctcatgcgt 65040
gtaatcctag cactttggga gaccaaagtg agtggatgac ttgaggtcag gagttggaga 65100
acagcctggc caatatggtg aaacccagtc tgtactaaaa atacaaatta gccagacctg 65160
gtggcatgca cctgtagtcc cagctactca ggaggctgag gcaggagaat cgcttgaacc 65220
cgggaggcag aggttgcagt gagccgagat ggtgccactg cgctccagcc tgggtgatag 65280
aacaagactc tgtctcaaaa aaaagagttt tcacatagta ggcactcagt agatgtttga 65340
gtaaatgaat tttccttcat ttgcttcctt gtttgctttt tcttagaaaa ctcaaaggag 65400
cccaggcaca gtggctcaca cctgtaatcc cagcacttcg ggaggctgag gcgggtgaat 65460
cacctgaggt cagaagttgg agaccagcct gaccaacatg gtgaaacccc gtctctacta 65520
aaaataccaa acattagcca ggcggcaggt gcctgtaatc ccatctactc cagaggttga 65580

```
ggcaggagaa ttgcttgaac ccaggaggca gaggttgcag tgagctgaga ttgtgccatt  65640
gcactccagc ctgggcaaca agagcgaaaa tccatctcaa taaataaata aataaataaa  65700
aataaaggaa aactcaaagg atattatctc tgaatttaaa acctgcaaca gtttatatca  65760
ttgaaaataa gaatggggaa gagacgaggg aaaaaagaaa ggtacaagaa agataggata  65820
tggagtagtg gagagacaat aattcagagt tattaatcca gaactctgca cacttactga  65880
atctcaagag tccctaaaac aaggctagtg tcatggcctt gtccgaataa agattaggat  65940
gccttcctgt ggtagatttt acttcccagg caagcaaaca gggaaggaga atggacatca  66000
gcctgttcat gttggtaagg agttaaaagg tattttttc aaagagtatc agtcctaaat  66060
aatttgtgga attaattggg tcctgttcag gtgggacacc ttcttcaaat atcttttttt  66120
ttttttttc tgagacaaga gttttgctct tgttgcccag gctagagtgc aatggcatga  66180
tcttgacccc ctgcagcccc cacctcccgg gttcaagtga ttctcctgtc ccggcctccc  66240
gagtagctgg gattacaggc ccccaccacc acacccggct aattttttgt atttttggta  66300
gagtcagggt ttcaccatgt tggccaggct ggtctcaaac tcctgacctc aggtgatcca  66360
cctgccttgg cctcccaaag tgctgggatt acaggcatga accactgcac ctggcctcaa  66420
atatcatatt taaagtgctg ctccgttacc aacaatgagc cgttttgtga ggtgttacaa  66480
gcttgtcgga ctccaggtgc tatacggtct caggagagag tcatgcagtg ataaagtgaa  66540
tctaacctag gtacttccag tgtatcagac ttaatgttgt tctcttccca ttcagataat  66600
tctatccaga ccatgatcac ttttgaccaa ggaggaaggt ggacgcacct gaggaagcct  66660
gaaaacagtg aatgtgatgc tacagcaaaa aacaagaatg aggtttgttt actctaatgt  66720
gtgcagagca cagcagcctt tccattgtgc tctgatcagt gccagccttt tggatgatga  66780
agtttcatac ttgattaggg tcctcagcat aaggtggaaa gtttggagat gagagtaatg  66840
aaattaactt agaatttcgg aagtaagaac tgaggaaagg tcaaaatact atggattatt  66900
tgtcttttaa agaagaacaa aactgagggc taacaatttg tggttcacta aactgctgaa  66960
ttaaaacaat ggccagaggg gctggtgatt agttaggggt cagcttggca gctgggagac  67020
tttagaggtt ctgcaagaag ccgcagctcc accattcata agcagtgcac agccttgctc  67080
atcggaaaca agaggaagag gatctggcct tcctttccct ctgcctaggc tcccatggcc  67140
agtgggtggt gacctgctta gtgcacaggg acgcaaggca gcccctgttg cagagagttt  67200
gggaaccgga actacgcagg tgtcactcca ggagatctaa agcctggagt gacaggcctt  67260
ggcaggcaag gaaaaaaggg aaaaaaaaaa caagcttttt atctggctct cacagaatgt  67320
gagcttgggg gacagctgga gttccttcag aaactgaagt accggtagtt cccgaaccct  67380
ccttagtatc tgtatcactg acatacactt tgcttttcta ggtggggttt tctgttttgt  67440
tttaagagcc tcaaatgatg agagaaagtg tgccttccta caccacccca acacactctc  67500
ctcctttaca ctcgcaagca ctgttgcatc tacccgactt tctgacccct gtttcccatc  67560
tgtctgcctt ggccctgccc agccactgcc ctcctcacct taagcctggg caggttcagt  67620
ggcctctgtg tttgccttgc tgcctgcagg ctccccatgc ctctccctgc ccagcgctcg  67680
ttgtggctct cttggcctgt gatgaatggc ctctgtccct gacctggtga gtaaaggttc  67740
tctcctggtg ggccctctgc caccttttca ttgtcattgc tcaccttatc cctgacacac  67800
cccttgtaac caaccccctg ccattccctg aacacccaca ctattcctgg aggaagttgg  67860
gcctgtctcc cccaacccca gttgactagg attggtggaa attctaacca ccctcagtga  67920
ccatccagtt agagctaatc attcctcttc atttcattaa tagtttgctt gaacctcttc  67980
```

tttttaaaaa aatagtagta aaatatacat aatataatat ttattatcat tttagccatt 68040
ttgaaccctt tttagagtgt taactttcat tcggctgtat acctcaacta gtttctgaca 68100
atacatttct tttttcccca gctttatgga ggcataattg acaaaaattg tatatttaca 68160
atgtacactg tgatgttttg atatatatat acattgtgaa atgattatca caatcaagct 68220
aactaacata tgcatcacct cacaattatc ttttgtgtgt gtggtgagaa catttaggat 68280
ctattctctt agcaaacttc aagtaacaat acagtattct agactgtagt caccatgtat 68340
attttccctc agaagcttat tcatcctgca taactgaaac tatgtaccct ttggccttca 68400
tctccccata ccccaagccc caaaagccac cattctactc cctgcttctg tgagtttgac 68460
atttttacat tccacttata aatgagatca tgcagtattt gtctttctgt gctgggctta 68520
ttttacttaa cataatgcct cccaggttca tgttttcaac agatgacagg atttccttct 68580
tttttaaggc tgaataatat tccattttct ttgtccattc atccatctgt agacgcttag 68640
gttgattctg tagcttggct attgtgaata atactgcagt ggacatggga gcacagatat 68700
cttttggaca taccgatttc atttctcttg aatatgaacc cagaaatggg attgctggta 68760
gttctgtcct tcattttctt ttttttcttt tttttaaaga cacagtcttg ccccgtcacc 68820
aaggctggag tacaatagca cgatcttggc tcacttcaac ctccgcctcc cgggttcagg 68880
tgattctcct gcctcagcct cccaagtaac tgagattaca ggcatgtgcc accacgcccg 68940
gctaattttt tgtgtcttta gtagtgacgg ggtttcacca tattggccag gctggtctcg 69000
aactcctgac ctcgtgatcc acccgcctct gcctcccaaa gtactgggat tgcaggcatg 69060
agccaccatg ctcggccctg ctgttattca ttttctagga aaatttctta cggtattgca 69120
taatggctgt accagtttac attcccacca acagtgtaca gggttccctt ttttccatgt 69180
ccttgccaat acttaccttt tatctctttg ataatagcca ttctaacttg ggtgagataa 69240
tatctcattg tggtttttat ttgtatttcc ctcatgatta gtgatgttgg gcattttttc 69300
gtatacctgt tggccattta tatgtcttct tttgataaat ggctgttcag gtcctttgcc 69360
catttttttag ttggattatt tgttttcttg ctactgattt gtttggatat taacccctta 69420
taagatgtat ggtttgcaag tattttctcc cattctgtgt attgtttgtc ttctctcttt 69480
tggtggtttc ctttattttg cagaagcttt ttagtttgat acaatctgat ttgtctgttt 69540
ttgttttttg ttgcctgtgc ttttagggtc gtatccaaaa agccattgcc cagatgaatg 69600
tcaagaagct tttttcccta tatttccttc tagtagtttt acagtttcaa gtcttacatt 69660
tatgtctcta atccattttg agttgatttt tgtacatgac atgaaataag gattgaggcc 69720
aggtgtggtg gctcacgcct gtaatcccag cactttggga ggccaaggag ggtggatcac 69780
gaggtcagga gatcgagacc atcctggcca acatggtgaa atcccgtctc taccaaaaat 69840
acaaaaaatta gctgggtatg gtgatgtgca cctgtagtcc cagctacttg ggagactgag 69900
gcaggagaat tgcttgaacc tgggaggcgg aggttgcagt gagccgagac cgcaccattg 69960
cactccagcc tggcgacaga gcaagactcc atctcaaaaa aaagaaagaa gggttgaaat 70020
ttattcttct gcatatagat attcagtttt cccagcaccg tttatttaag aggctgtctt 70080
tttcacattg tgtgttcttg acacccttgt caaagttaag ttgacaataa atgcatagat 70140
ttatttctgt gctctctatt ctgttccatt ggtctatttg tttttaacgc cagtaccatg 70200
ctgttttgat tactatagct caataatata ttttgaaatt aggtagcatg atacccccag 70260
ctttgttctt tttgcttgca attactttgg ttattcaggg tcttttgtgg ttccatataa 70320

```
attttaggat tttttctatt tctgtgaaaa ataccattgg aattttttt aagaggcaaa  70380
gtcttagtct gtcaccctga ctggggtcca gtggaataat cataggtcac tgcagcctca  70440
aactcctagg ctcacacaat cctcccacgt cccaagtagc taggtgtgta ccaccacacc  70500
tgtctaattt tggtactttt tggtagagat ggggtttcac catgttgccc aagctagtct  70560
tgaactcctg gcctcaagtg atcctaccac ctcagcctct cagctgggat tacagatgtg  70620
agccaccaca actggttgtt ttgttcttga tgtaccttaa gtacctaaaa cagtgcctga  70680
aatatagcag gtactcagta aacatctgat gaattaacgt gtttggattg ttctgtgttg  70740
tcacagaaag agggttattt ataaccatat aatagtaaaa aaagacagtc aaaataatag  70800
gcattacatt taatctgtag atcactttgg gtagtatgga cattttaaca atattaatta  70860
ttccaatcca ggaacatagg atatatttcc ttttttttt ttttgtcatc ttcaatttct  70920
ttcatcaatg ttttgtagtt tttagtcttt cacctccttg gttaaattta tccctaagtt  70980
tttttgttt ttttttttta agtttttttc ttgtactatt gtagatgaaa ttttcttgat  71040
ttcttttttg gatagtttgt tgttagtgta tattgtattt ttatatgttg attttatatt  71100
ctgcaacttt tttgaattta ttagttttaa catttttggt ggagtcttta aagattaagg  71160
atttttatat ataagctcat gtcacctgca gacagacaat tttacctctt tctttctggt  71220
ttggatgctt tttgttttta tttctttttc ttacttaatt gctccagcta ggacttccat  71280
tactataatg aacagaagtg gtgagaatgg gcatctttgt cttattcctg atcttagagg  71340
aaaaggttta gcttttgact gtttgagtat gatgttagct gtgggcttgt cacatatagc  71400
ctttattatg ttgaggtata tccctttat acctaattta ttgagagttt ttatcatgaa  71460
tgggtttatt atgttgaggt atatcccttt tatacctaat ttattgagag tttttatcat  71520
gaatgggtgt tgaaatttgt taagtgcttt ttctggattt atcaagatga tatgatttct  71580
atccttcatt ctattaatgt ggcatatctc atttattgat ttgcatatgt tgaaccatcc  71640
ttgcattcca cagatagatc ctacttgatc atggtatata atctgtttaa tatgctgttg  71700
aattcagttt gttagtattt tgttgagaat ttttgcatct atgttcatca gagatattga  71760
cctgtaattt tgttttcttc tagtgtcctt gtctggtttt ggtagcaggg taataccacc  71820
cttataaaat gagtttggaa gtgttccatt ctcttcaatt tttggaagag tttgagaagg  71880
atcggtctta attcttcttt gaagaaagtt tgctagaatt caccattgaa tccatcaggt  71940
cctaggcttt tcttgttggg aggtttttga ttactgattg agcctcctta ctcatattag  72000
tatgttcaga ttttctattt cttcttcatg atacagtctt ggtaagctgt atatgtctag  72060
aaattcatcc attttttct agattatcca atttgttgat gtatagttgt tcatagtagt  72120
ctcttaggat cctttgtttt ttctgtagta taagttataa tgtctcctct tacatttctg  72180
attttacttg agtcttttct ttttttctta ttctaattaa aagtttgtca cttttttatc  72240
ttgtcaaaaa aaacaactct aagtttcatt gatctttcct gttatttttc taacttctat  72300
ttcagttatt tctgctctgt tattatttcc tcccttctgc taactttggg cttagtttgt  72360
tctttttcta gttccttgag gtataaagtt aagatttttg agatttttct tttttcttaa  72420
tgtagacatt tatcaccata aactttcttc ttagaactgc ttttgctgca tcccttaagt  72480
tttaatatgt tgtgtttccc ttttcatttg tctcaagttt tttttatttc cctttgactc  72540
attggttgtt caagaatatg ttgttcaatt tccacattca tgtgaatttt ccaattttcc  72600
tcccttact gattctagtt tcataatgtt gtagttgaaa agaacttgag gccaggcaca  72660
ctggctcacg cctataatcc ttgcactttg ggaggctgag gtgggtggat cacgaggtca  72720
```

ggagttcaag accagcctgg ccgacttggt ctctactaaa aatacaaaaa aaaaatagct 72780
gggcgtggca gcgggtgcct ttaatcccag ctactcagga ggctgaggca gagaattgtt 72840
tgaacccggg aggcggagct tgcagtgagc caagatcacg ccactgcact ccagcccagg 72900
tgacagagtg agactccgtc tcaaaaaaaa aagaaaggat acttgaggtg atttcagtct 72960
tacatttgtt aaggcttgtt ttgtggccta acatatgcac tatcctggag aatattctct 73020
gtgcacttga aaagaatgta tattctgctg ctattggata gaatgttctg tatatgtctg 73080
ttaggtccat ttgtatggtg ttgttcaagt ttgctctttc cttactggtt ttctgtctgg 73140
atgatctatc attgaaagta agtattgaag tcccttacta ttattgtatt gtcgtctacc 73200
tctttcttca gttctgttaa tgtttgcttt atacatttag gtgctctaat gttgagtgca 73260
tttatattta ccaatgttat atgctcttga tgaattgaca cctttatcat tgtgtggtaa 73320
ctttctttat cccttgtgat agttttttac ttaaagtcta ttttgtctga tataaatata 73380
gccacccccg gctggacatg gtggctcacg cctgtaatcc cagctctttg ggagaccaag 73440
gcgggcggat cacgaggtca ggaaatcaag accgtcctca ctaacatggt gaaaccctgt 73500
ctctactaaa aatacaaaaa attagccggg tgtggtggca ggcgcctgta gtcccagcta 73560
cttgggaggc tgaggcagga gaatggcatg aacccaggag gcagagcttg cagtgagctg 73620
agatggcacc accgcactcc agcctgggtg gcagagcgac actccgtctc aaaaataaat 73680
aaataaatat agccacccct gctctctttt ggctaccatt tgagtggaat atcttttttt 73740
tatctctact tttagcctat gtgtcctctt acacacatag gcctttacag atggcttcag 73800
caggggaagc ccttaccagg tagctcatcc agagattctt ggggggggcaa ctgacaggtt 73860
ctgcaggtag gtgggcctgg tgccttggtc tttgggggta gcttggaggc tgggtcctct 73920
gcggcaggcc tggcagtgga atccactagg gtggaccttt taagtgggtc ttcaggtgaa 73980
acacctggag cccggtaagt agatctgcag gagccagcct ggtgcagggg tgggccctac 74040
cctgagcctg caggggctgg cctgatgcag ggtccactt ggctgggtct gtgagagtgg 74100
acctggagcc tttaagtttc ttaaagacaa gactggatct tatttcgaac caccatcaca 74160
tcttgtacgg tgtctgaagt atatcaggtg cttatcaagt ttatttgtgt agagtcagcc 74220
tttaaacatt gttcagaggc tttgatgtaa tgcaaaaata aaataaacgg agacaggtta 74280
cccatgagga aatatttgct tccagatatt gtagtacatt tcagaatcaa gagtatgcca 74340
ctgagctaca actcaacaac aaacaaatag cctgaataaa aaataggcaa agaacttgta 74400
tagacatttc tccaaacaca atatagaagt gactaacaag catataaaaa gaggctcagc 74460
atcactaatc attaggaaaa tgcaagtcaa aaccacaatg aggtatctcc tcacacagat 74520
tagggtggct actattttaa aaagtgttgg caaggatatg gagaaattgg agccctggtg 74580
cacttttggt gaaaatgtaa aatggtgcag ctgctacaga aaacagcata gtagttccta 74640
aaaaaaatta aaaataggat tatcatatcc agcaattcca cttctggatt atacatccaa 74700
aagagttgaa agcaggttct caaaaagata tttgtacaac catgtacata gcaacattat 74760
tcatgatagc caaaaggtag aagcaacttg tgtctattga cagataaatg agtaaataaa 74820
gtgtggggtg tgtgtggata cagatacaca cacacactta aataatattt agcctttaaa 74880
agggaggaaa ttctgacata tgctattaat acaacatgga tgagccttga ggacattatg 74940
ccaagtgaaa taagtcagac acaaaatgac aaatattatg tgattctact tatatgagct 75000
acctagagta gccaacacaa agtaatatgg taaaaatcat agaaaacaca aagtaaaatg 75060
gtagtttcca ggagctggga ggaggaagaa gtaggtaaca gttgcttaat tggtgattgt 75120
attttataag atgaaaaagt ttagagatgt ggttgtacaa caatgtgaat atacttaaca 75180
ctactgaact atacacctaa atagtaaata aatagttaag atagtacttt tacctaggtc 75240
tgggttaact taaagcttta ttggaagggt tttgtgaaat gattaaagaa attgtatctt 75300
tatctttggt tctaatctac gcttttgttt cttttcacag tgcagccttc atattcatgc 75360
ttcctacagc atctcccaga aactgaatgt tccaatggcc ccactctcag agccgaatgc 75420
cgtaggcatt gtcattgctc atggtaagga acctccccact caccacctcc aactggaaca 75480
gtggctgagc acactgaaac tcagccaaca ggctttgaac gctctgagaa gaaacaatgt 75540
ggatgctttt acattccttt ggtagaattt cttacattat aacaacactt tgggtttttc 75600
atcaactttt atcagagaga gcaacacaac ttctccgaag tttttggtgg ttttctttcc 75660
tactaaaaga ggcttgatgg gaaataatca gaataaattc attcaacatt attctctctg 75720
gagtaaatgc tctctgtttc attgcctatt tgtgctaatg agatggtgga ttatattgca 75780
ggtagcgtgg gggatgccat ctcagtgatg gttccagatg tgtacatctc agatgatggg 75840
ggttactcct ggacaaagat gctggaagga ccccactatt acaccatcct ggattctgga 75900
ggcatcattg tggccattga gcacagcagc cgtcctatca atgtgattaa gtatgcatga 75960
actcatctca cacacactgt ctgcatagag ggcaactggg ggaatgttct tcagtttatt 76020
ggggggatgt tacagactat aattcaaatt tttgcatttg acagaactat agataagatt 76080
ctagaaagga ttgcttttaa ttggcaactc agattaaatg gcattgtttt ttcttctgac 76140
tgcctttagc taacatattt gtcacttctt aaaaacattc tttctgggtt gggcgcagtg 76200
gctcatgcct gtaatcccag cattttggga ggccaaagca ggaggatcgc ttgaggccag 76260
gagttcaaga ccagcctggg caacataggg agaccttgtc ccttgtctct aatattattt 76320
caatcaaaaa aaaaaccata tatatatata tgtgtgtgtg tatatatgta tgtgtgtgtg 76380
tgtatatata tgtgtatata tatgtatata tatgtgtata tatatgtgta tgtgtgtata 76440
tatgtgtgta tatatatgtg tgtgtgtgtg tgtatgtata tatatatata tatatatata 76500
tatatatata tattctttct gtctacaaaa ttattatgga agcgttcaag cactctagat 76560
tgaaaatgac ttcttaagta caagttctga gctgggtgca gaggcacaca cctgtaatcc 76620
cagcactttg agaggccaag gtgggtggat tgcttgagcc caagagttca agaccagcct 76680
gggcaatgtg acaaaaccct gtctccacaa aaaaaaaaaa agaaaaatta gctgggcgtg 76740
gtggtgcacg cctttggttc cagctacttg ggaggccgag gtgggaggat cacctgagga 76800
ggtcaaggcc acagtgagct gagatcgtac cactgcactc cagcctgggt gacagagtga 76860
gatcccgtct caaaaaaaaa aaaaaaagaa gtataagttc ttataaaata atttgattgt 76920
tatttattta tttatttatt gagatggagt tttgctcttg tcacccaggc tggagtgcaa 76980
tggtgcaatc ttggctcact gcaacctctg cctcccaggt tcaaatgatt cttgcgtctc 77040
agtcacctga gcagctgaga ttacaggcat gcaccaccac acccagctaa tttttgtggt 77100
tttttgtttt gctttgtttt ttgtgttttg gtagagacgg ggttttgttg tgttggtcag 77160
gctggtctcg aactcctaac ctcaggtgat tcacctgcct cagcctccca aaattctggg 77220
attacaggcg tgagccacca cagccagcct taaatttatt aatttaaaag ccagttctta 77280
cctgggtcac tctcctgtct ttcctttgaa ataatttctg taaaggtatt tactttcata 77340
ttctctctga acaaatctct tccttatcct gttaactaca gacgttaaaa gttaaaatag 77400
ttggctgggt gcggtggctc acgcctataa tcccagcact ttgggaggcc aaggtgggaa 77460

```
gattacctga ggtcaggagt tcaagaccag cctgcccaac atgtgaaact ccatttctac  77520
taaaaataca aaaattagct ggtgtggtgg cacgttcctg taatcccagc tactcaggag  77580
gctgaggcat gagagagaat cacttgaacc caggaggcag aggttgcagt gagtcgagat  77640
cgcgccactg cactccagcc cggtgacaga gtgagactcc atctcagaaa aaaaaaaaaa  77700
aaaaaaaaaa gttaaaataa ttgtcagcca ataagccacc acctaaatgt aaggggtttt  77760
gtctggtttg ggatcaaaaa gccagagtgg ttttctgaat tcccagtaca cattgatcct  77820
ctgtcatgat ctttctgtaa ttgtggtttc aggttctcca cagacgaagg tcaatgctgg  77880
caaacctaca cgttcaccag ggaccccatc tatttcactg gcctagcttc agaacctgga  77940
gctaggtcca tgaatatcag catttggggc ttcacagaat ctttcctgac cagccagtgg  78000
gtctcctaca ccattgattt taaagatatc cttgaaagga actgtgagtg tctcctttga  78060
ccttttctac cagaaacttc caagtccatt ttcctaaata atcaatatgg tttaatttct  78120
tttagctgga atcagcagat gcatatgcat atgaaagagg attgacagat gttctgtgtg  78180
ggtgattaag taatggaatg gcatcagaaa aacaacctcc tcctcggtgc tagcactgtc  78240
caggagaaat atgagggcca catatgtcat ttaaattatt ctgtcagcta tattataaaa  78300
gtaaaaagaa aggtgatatt aataaaataa acttaatata tccaaaatat tatcatttca  78360
acattaagca atattaacgg cccagaaaat aggttcagaa aaggattcac aatgttcatt  78420
gcacagtgtt tccaaagtgt cacaagcaaa ccctaacctc actgccaaac aaagatgctg  78480
gcattatgct aagaaataag gggaatggcc aggcgcggtg gctcatgcct gtaatcctag  78540
cactttgaga ggccaagata ggcagatcac gaggtcagga gttcgaaacc agcctggcca  78600
acagggcgaa actccatctc tactaaaaat agaaaaatta gccaggtaag gtggcgggtg  78660
cctgtaaggt ggcgggtccc agctagttgg gaggctgagg caggagaatc atttgaaccc  78720
gagaggaaga ggttgcaatg agccaagatc atgccattgc actccagcct gggcgacaag  78780
agcaagactc tgtctcaaaa aaaaaagaag ggggataaag aaaaacactg gaaaaaggat  78840
gacctgtagt taagtgttgg cataatacaa taaaagactt aacgtttcta gacactctag  78900
ttgaatttgg tcctttgaga ctgtcgtggg ctcatttcct cagcgtgttg atttagtgac  78960
tcctgaagga gcagaccctt ggtttggacc tcacatttcc ataagacgtt caaatagatt  79020
taatgcctga gggtcgctgt catctaaatc cattcagtag actgtacaga agctggcttg  79080
ggagttctcc cctcagcagg cagctcccag ttacccctaa agtgtaatgt cattaaaaga  79140
tttgttaagc acctgctctt tagcaggctg tatgctggtc ttcatatccc aaaggataaa  79200
acctaatcca ctgtctttag gtcacagcct ttgagtcatt tttccagtag atgatacgac  79260
atactaagcc agaaactagg tttatcagca atatgcattt gagagccggt caactgagct  79320
agaagtctag gaaaaggatg ttttcccttc ttccttaagc caatgaacac atggtgaaat  79380
tgaacctgtg ctcttggcta attagtatct tgtcctaaac aaagagctcc ctggtcctga  79440
gtggagaata tctggttgct tacctctgac agctcctact gactgagggc gtaggtgtgc  79500
aagacacaca cagcagcctc ttagtttgga aggaacttga gagattttct atccagcttc  79560
ccacttcaaa acaaataggg tttttcctaa tcctcagatg gatgttgaga tggaaggaat  79620
actcttttgg catgaggaaa tgcgattgct agtaggctct agactagtgt aactttttgt  79680
ttgcaattcc aaaatgaagg aataggttga gtcagacatt cccactttcc ctctccttgt  79740
tcttcctata gcctggcagc tgcctcccgt gggtgggttc tgtgctgtgt actttcctga  79800
```

-continued

```
acagtgtgtc tctcctttag gtgaagagaa ggactatacc atatggctgg cacactccac  79860
agaccctgaa gattatgaag atggctgcat tttgggctac aaagaacagt ttctgcggct  79920
acgcaagtca tccgtgtgtc agaatggtcg agactatgtt gtgaccaagc agccctccat  79980
ctgcctctgt tccctggagg actttctctg gtatcagcat tcctcagatt tctctgtctc  80040
cctttccctg ttggaggagg tgaaagacag ttttcttata gggctaacaa atattgaaat  80100
ccagccgggt gcggtggctc acacctgtaa tcccagcact ttgggatgcc aaggcaggca  80160
gatcacttga ggccgggagt tcgagaccag cctggtcaac atggtgaaac cctatctcta  80220
caaaaaacaa acaaacaaaa aaaaattagc agggcatggt ggcgcacgcc tataatccca  80280
agctgctcag gtggctgaga cacaagaatc acttgaacct gggaggcaga ggttgcagtg  80340
agctgagatc atgccattgc actccagcct gggggacaga gcaagactct tgtcccaaaa  80400
aaaactgaaa ccctttcccc caagagtgga gaactgctgc ttcttatcaa ggaagctgag  80460
gcacagagaa aggaaaccag aattgttaat aatgaaacag atagcacgta ttagacagtt  80520
aattattggg cagaaccagc aacaaacccg agaaatcctg agttgacagt ggtgtgaagg  80580
agaggagtga tataagaaag aagagaataa aacaaacaaa aatctgtaga aaatgaaaag  80640
acagaaacac caaaagaagt ggtagaggag caaagaggaa attggacttt agaaaacagc  80700
ctgaggccag gcacggtggc tcatgcctgt aatcccagca ctttgggagg ccgaggcggg  80760
tggattgctt aaactcagga gtttgagacc agcttgggca atatgatgag accctgtctc  80820
aaacaaaaaa aaaaacagaa agaaagaaaa agaaaacccc ttgacagcat gagctcagca  80880
ggcagacact aggttttgga tcctctgcaa gaatcaaggc agagagatgg tggttggtcc  80940
tgagactaga ggtgacatca gtatagtcat ggtcccatca aggtttagag gccatcaaag  81000
tggactccct agagttcagg accatccaga cttaaggatt agttacttgg ctggcattgg  81060
gttagttgat tatataaggg catgagtccc tggatagctt aaatgaggta atttttgggc  81120
aaataagagg aactgcttca catcacagat gataatcttt tggaacttgt tacctgcaaa  81180
agatactgac acaagataaa agtagatcct aaaggatttg gacaaagaag gcaggcagat  81240
agcagccatg gccctttatg tcatgttctc tcaaatcgca ggtgacagta gaatataggt  81300
ctgaccaaaa tgcaggtctg acccagtgtg gtttctcctg catggctcac acctgtgtgt  81360
ggcatgatta agggtcctcc cttctctgtt tcagtaagga tcacctttgg tgttccagta  81420
gggctggagg tcatcgataa acctgtaaca ctgtaaaggg ttctctccta tcctcgactc  81480
caaatatgcc aagctcttca cctgtgcttc tgctcttctc cagcagtgcc atggtttttc  81540
agacctccat gccaccgcac atgatgctcc ctctgcctga aaagtctttc cacagtccct  81600
gcttcacccc caagtctggc gacttcccac ttagcctttc atacttagct caggtatcac  81660
cactagatgg gctttccctc atctagaccc ccagagttcc cctattacag cacttactaa  81720
attttaatta ctatttatag gtttgcttcc atcattaagc cccaaattcc ttggaagcat  81780
attctattcg ataataatat agtaatcatg atagcagcta acatttattg agcactaact  81840
ttatactagg cactatccta agcaatttac atttaacctc gcaacagaga ggacatgact  81900
gatatgcccg tgggaagtgg cagagctggg atgtgaaact ggcatcccaa ctccagagcc  81960
cacatgtttg ggaagtgggt cctttatgag tgagaagggt actcacaaaa atccagaaat  82020
ttctgattga atacctaaaa ctcttatccg aatttcctcc tgttatttga ggggtgatat  82080
cttcagcatc ttttgttctc catacccctct ctcctaaata cttaccagga aaaccttgaa  82140
atacaagcag catccatata ttccccaaat actcattgaa taccagctat gcgcaggtaa  82200
```

tgaaaagtga taatggaaaa tttgttgcaa aacagaaggt gccaggtgcc atggggattt 82260
agaaaaggaa gagaacattt catgtagagc tgaaaggaag tgggtcaaag aaggccttgt 82320
tgaggaggtg gtatgagagc tgagcgttga caaatggtag gatttgacca tgagcatctg 82380
ggaagaagca gctcatcaat gccagtggac tgctgcaagc agagacacca acagcatgat 82440
caaggaaggg tgtcctggaa gataggccat tggggaagtc acagtagtca tgataaagaa 82500
gtaagtaggg cccagaagga ggatcctcag gctaaatttt ccactgagat agtgggaagg 82560
aaggtaatgt catggacgaa tacggaaatg ataaggagag cctggcacaa aggagaaaac 82620
atgatgtatt ttgaacatct tatttctttg aggttttgtc agcatattta ggtgggatat 82680
ccagcatgta tttgaaatat aggattagaa ctcaagagag gtaaaacctg gaagttttag 82740
ttgcaaccaa aaatagttgt gatcactaag ggagagcaga tagagaaaaa gtaagagaat 82800
gcattatacc tgccccctgc ccccggcaaa agactacatt tatgggttag gaagaaagaa 82860
gagcaagcag tggcgggggc agcagagggc agagaaacag atgagtgcag ctttaccaat 82920
gccaaggttg gcaggggcac aacagtatgt cagatgctgc agaatgggtg gtctggggga 82980
atgagacccg agagggctcc actgaatttg atgattattg agccttaggg gcactgcaga 83040
cactcatttt cttttctttt cttttttttt tttttgagac ggagtctcgt gctgtcgccc 83100
aggccggagt acagtggtgc gatctcagct cactgcaacc tccacctccc gggttcaagc 83160
gattcttctg cctcagcctc ccgagtagct gggattatag gcacacacca ctgcacctgg 83220
ctaatttttt gtatttctag taaagacggg gtttcaccat gttggccagg ctggtattga 83280
actcttgact tcaggtaatc cgcctgcctc ggcctcccaa gtgctaggat tataggcatg 83340
agccaccacg cccggcccag acacttattt tcaaagttgc agaaggggtc aaagccaaaa 83400
tgcgtggaag aaaaaaataaa tgagtaaaat aggacaagta aaaaaatatt cttttgagaa 83460
atgtgggtag taagggagag gtgggttaag gaagtaattt ctaaggtcaa gacatgcagg 83520
ctaaggagac gctgccagct gagtgggaga gattgattgt tcccctcata ctcagggaag 83580
caaggcccca gggcaggtcg gaggagggga accaaggatg ctcatggagt cagccctgga 83640
gattgtcagc agacattgtt tctttggggt aaacaggaaa aggagagcag tgggtggcac 83700
tatggagaga tggggtagaa tggaggacag aaaaaggtgt tcacatggaa ggcaaagact 83760
atctaagaag ctaagaggaa cagaagtggg gaagacagaa aaatttgccg tgtactgcaa 83820
gggcaacata ataatgacat ttggaggtaa agaaaagaat tgctggctgg gcacagtgac 83880
tcatgcctgt aatcccaata cttcgggagg ctgaggcagg tggatctctt gagctcagga 83940
gtttgagatc aggctgggca atatggcaaa actctttcta cagaaaatac aaaaattagc 84000
aaggcacagt ggttcacgcc tgtaatgcca gcactttggg aggctgaggt ggacagatca 84060
cttgagccca gtagttcaaa acaagcctga gcaatttgtc aagacctcat ctttacaaag 84120
aattagacga gcatggtggt gcatgcatgt ggttccagct ccttgggagg ctgaagcgga 84180
aagatcactt gagcccagat ggttgaagct acagtgttca tgccgctgta ctccagcctg 84240
ggcaacagag cgagaccctg tctcaaaaaa aaagcgggga gggggaagaa aagaaaagaa 84300
ttgccaagta tccctgagtt gagagctgct gctgatgctg aggtttctgt gtgagtctcc 84360
acccctctgc aggctgcatc agtcacctcc ctgcgcctga gctgcctgca gtgcacagcc 84420
ttggggccct agctagtcct acccccacca ggcctgaccc ataagcttct tttccttaat 84480
aaggccctct ctggcggggc acggtggctc acacctgtaa tcccagcact tttggaggcc 84540

-continued

```
gaggtgggcg tatcacaagg tcaggagttt gagaccagcc tgaccaacat ggtgaaacgc  84600
tctctctact aaaaataaaa aattagccag gcatggtggc atgcacctgt aatcccagct  84660
actcagaagg ctgaggcagg agagtcgctt gaagccggag gcggaggttg cagtgagcca  84720
agaacacgcc actgcactcc agcctaggcg agagagtggg actccatctc aaaaaaaaaa  84780
aaaaaaggcc ctctccgtgt ctgttttcct aaatcgacct ccttcagagg tgtcacagga  84840
cttcctgagc tactttctaa caacccaaga ctggaatgtt aaccatccac taccccacat  84900
aacccttcat tgctagtcac ttaacggtct tccagctgct ttgaaaggta ctttatttgc  84960
tgactcttgc agtgattttg gctactaccg tccagaaaat gactccaagt gtgtggaaca  85020
gccagaactg aagggccacg acctggagtt ttgtctgtac ggaagagaag aacacctaac  85080
aacaaatggg tgaggtggcc ttttctccct tgtcacgatg gatgaggtgt tcttgttcag  85140
agtgaaagct gcttctctcc acactgagat ccaagcccta ctttagagca ctatttttgg  85200
cggggttggg gaggggcagg atatgaaggc ctccttcaag ggtcaactac aggaggtgag  85260
ccatgagtgc ttggtgtcag aggactcaac cccaccaaca ccacgaggca gagcaggaga  85320
acaagctcgg ccagatcctg cacccctgcc tcccgcccaa ccacccccag gaagggagga  85380
gaggcgaggg acccacaggc agaatgacag aagcgtccca tccgccatga acgtccatcg  85440
ctcgtctggc acagtttagg cacagccagg gagagctctg tctgatagga ctttctttgg  85500
tgatggaagt gttctgtaat ttgctgtgcc caatatgata gtcactagcc acacatagct  85560
gtggacacta gtgtaaccga ggaactgaaa ttttcgtttt aatcaatttt aagtagccac  85620
catattggac agtgctgctc tagacgggcc tcattacctc gctcccctga taacttcccc  85680
tctcccattt tgtaccactt gttaatgagc tttttttgggg tcagatttct ttggcacagt  85740
ctcttaggta gaaagaacag gcatgtttct gacagcaggg gacagagatg cttagtttgc  85800
ttaaggcctg aaactacaca aaatatcccc caaaacatcc ctgtggacat tccccccagg  85860
cctgaaacat gacgtaagga tgggaagctt ttcggcagct tttcaaatct tgtttccaag  85920
aaataggcag gtacccagga atacatcctt atcttctgtt accaaatctt ctttgcctgg  85980
taggtaccgg aaaattccag gggacaaatg ccagggtggg gtaaatccag ttcgagaagt  86040
aaaagacttg aaaaagaaat gcacaagcaa ctttttgagt ccggaaaaac aggtatgtta  86100
aaataggtct agttttcagg tacaaatggg attttgtgtt ctgctaagaa aaatcaaagt  86160
taaagcatca agagttttgt tactgataaa aagtggtcaa actacttctc tcaggcttcc  86220
cttatacagg aagctgttag catgaaggat gggtcatgta acccagtgat aagctcaccc  86280
tactgaaagc tcttttctta ttgagggttg ggggatgata ttctgtaaag ttgtaaaatt  86340
cttaaaatca tacagttgtg gaaatttctg aggctgagag tcatttagga aaacaaaaag  86400
gttgtctgtg ggctgggtac agtggctcac acctgtaatc ccagcacttt ggaagtccaa  86460
ggcaggcaga tcactgaggt caggagttca agaccaggct gtccaacatg gtgaaaccct  86520
gtctctgcta aaaatacaaa aattaaaatt acaaaaatta gctgggtgtg gtggtttacg  86580
cctgtagtcc cagttactcg ggaggctgag gtaggagaat catgtgaacc tgggaggtgg  86640
aggttgcagt gagccgagat cgtgctgcta cactccaacc tgggcaacag agcaagactc  86700
cgtaccaaaa aaaaaaggtt gtctgtgaag ggccatgacc tggaattgtg catgtgtgga  86760
agagaagagc actgggcaat aggtagggtg gatctctgac caagtcatgt taagtatgtt  86820
caaagtgaaa aattgagcta tggtaatggg ctggttttga tttaaatgaa gcaagttacc  86880
tgtcgggcat ggtggcttac tcctgtatag tcccagcact ttgggaggct gaggtgggga  86940
```

gatcagttga ggctatgaat tggagagcag cctgggcaac atggagaaac tccatcttta 87000
caaaaaaaat acaaaaatta gccggatgtg gtggtgtgtg cctgtagtcc cagctactca 87060
ggaggctgaa gggagagaat cacctgagcc tgggaggtca aggctgcagt gagccatgat 87120
catatcactg cactccagcc tgggtgacag agtgagatcc tgtctcaatt taaaaaaaaa 87180
aaaaaaaaaa aaaggttatg aggctgcatc caaatctgta gcactgaact acctgtggaa 87240
ctggagatgt gtaaagagga aacctcttga taatgaaaca ctagaccagc agcatgactt 87300
cagatgctca acagcaggcc cgtttcccaa ttcgtaatag gagaggtcaa gctggatcac 87360
ctgcagtccc tcctctctgc tgttctaagg gatgagggac tgacaagggg tgggattaag 87420
gagatgatgg gagaggagtg tgtgagtgtg tgtattggta agggggcgag ttcctccttc 87480
tgtgcaccct tgtcctgggc tcctggtgac tctcctcaga gtgttcgtgt gtgtgattgc 87540
acaggactcc cacccacagg gacacagctt gtcctagaat ccagctctgc ctcctctggg 87600
atacattgaa aacacacact ccctatttcc cacccagaag caggtaggtc acatgcaaac 87660
agtgatatga taaggcttat ttataataat atataaaaaa ttaagtaaac aaataaatct 87720
tggtgtcata taatggcctg cctggttctt ctgacacagc ttcttcccag ataatggccc 87780
tgttctagag tcattcagcc tactgttaca gtagtctccc tttcctactc cacccttaag 87840
ccccaagact tgtgaacagt ggtagtgtga agcaatcata cttgatctag gcagttgccc 87900
aggcttccag tgtaactttg acatttaaac cacagaattt gaaggttcaa ggcagttgga 87960
gctaagatga ctctctgcca gctataatat tctcctggta acactgagat ggttcatctt 88020
ggggggttgg aaaagagcca tcattaagcg catcaggact gcagatcatt cacaaagaga 88080
tgaggggaat gagtggctgc cttgacctca gtcctaggat atgcatgcct aaaacttttg 88140
tgtttgtgtt ttaatttctc aagaattcca agtcaaattc tgttccaatt atcctggcca 88200
tcgtgggatt gatgctggtc acagtcgtag caggagtgct cattgtgaag aaatatgtct 88260
gtgggggaag gtaaggaaca cagaagtcaa tccaaggtac tgagttcaag ccagaaggct 88320
gatctagggc atatggctga gtctactctt ggcaaaaact aggtacttgc agtactgttc 88380
ctgaaaaatc aggcccaaat cttctcatgt cgtacatttt tcatatgtca accatggact 88440
gtgctttctg tgtctgtgat gcgttcctga gtgtataaaa ctgagaaagt ccacagtcct 88500
gtaagaagtg cacccctgct gtgtaccacc gagtgttaag gaggtttctg ttcacaggtt 88560
cctggtgcat cgatactctg tgctgcagca gcatgcagag gccaatggtg tggatggtgt 88620
ggatgctttg gacacagcct cccacactaa taaaagtggt tatcatgatg actcagatga 88680
ggtgaggcta tttcttcttg aatggtagta cccccccccc caaaaaatac aagaaaataa 88740
agtctgtctt ctattcatga tcaagatatg ccagggccaa ggcgacttaa tgaccataag 88800
atttggcaag cccagaaact aggtgattgc ttttgaaata ggagtgttgt ggtctgtcgg 88860
taatatggtg catgtctttt tcaggacctc ttggaatagc tcttcagagg agctggaccc 88920
agcatggatg gtggaaccac agtacctctt acactccctg tggctccaac ttcaggaaat 88980
aaatttccca ttgcgaggga cccagctctg tttctgctgc ttccatcaaa gccaaaagga 89040
cctacactaa agaaatgcag ggtgggggtg gggaaccctg agcacttttt tacaattggc 89100
tctgagaaaa agggagacat tttaaattct ttaacttctt atttctcgtc ctgtctcttt 89160
gcaaagtatg ggcttttttg tttttgtttt ttaagggaaa cgaaatggaa ttcgaaggga 89220
ccttttcact aaccccactt ctgtgtgttc tgcatggcgc ctgccccagg gcatctgcca 89280

-continued

```
actccagtat cagctctcac agtgtacttg gtaccatccc tgggctctgc tggcgagacg  89340
aaacagctgt agagatgaaa acaggctgca gaggctggca cagcctggcc ggcttttctc  89400
catctgggga cagtcctact ccaagaacac tgcacaccag ctcctcacac agatcccact  89460
tactcttttt tttttttca gagaccacag accacagtga tttttctttt cccttgttta  89520
attaggcaat acccttgtta attgcccttt ggcaactaac ttaaccatgt gcttcccaca  89580
cagtacatca ggaaaactta cagggcaata tttttaactt ggggcaggaa gaagggagca  89640
gcagagaatt gactagatat agcacctatt aaaagagaac tcttgcttct tctgagattt  89700
ttcaagctgt gctttgtgtg tgtgccagta gacttacgca aggacagggt acaaacttag  89760
ctggaagtct gcccaggctg aatgatctct tccctagagt tgattgtcgg gtacacagtg  89820
tgaacccccg aagacggaac ctcacagtct tccatgttcc cttcttaact gtcgtgtggc  89880
tcgttgctaa atcatgacaa tggctgccta tctgctgctt cttaggttgc tgttgtacat  89940
ggaaccagga ctagagattt tttcagattt atagacttaa aaaattagaa ttttattacc  90000
aggctttcct tctcacccct tttttctgac tttgccaagt aatttgttga cacgaaaatt  90060
ttggaggaac caattgaaaa cacacttcca gtctagatga tgctttgtgt gatacattaa  90120
gttcttattt tggattaaaa gaagttttcc atttgatacc tctctaaatt aaataaatta  90180
tagaatgtag ttgggtggat tttggggtgg ccatatagta atggaaagct gcaataatta  90240
gttttaatac agcttgaata tttgctatat agaaatatag tatggaaagt ttttggtctt  90300
aatgtagcta ctgtgcgggt cacagtttct cccaatgatt atgactggga cattctttgg  90360
tagataccat ttgctactag tttattttgt ggctagaaag tcagttttgt gtgttttttt  90420
ttttttttat ttgaagtgcc aaattaactt tagtcagaat gtgagcagat ggctaagttc  90480
tctcctcccc agaatggatt aacagctgcg tggaaagtgg gggagagagt ggatggagac  90540
ttttagagat gttaaaactg cagtagaatg aaatgagtca gggagcttca gttagaaaat  90600
aaagttgagg cagtttttgt gaagataata tggttagggc tggagtgcac tagtcttttt  90660
gcttattcat tttgcatggt tttaaaatta aaaataattc cgaagataca ccagctcaca  90720
aatgaaaacg tcagcctctg ccccaccctc cctcctgccc aaagtgaatt tggtactcag  90780
aaaagaactg tttataccac tcacctttct cccagcatgt actcactgtg ggcagatgca  90840
ccaatacatg gtaatcctct tactcatttt aagacgtagg aaactcaata ttcttctcta  90900
accatatacg atagggctct tcgcttttaa tgatatctgg gatttctgtg gaacttggca  90960
aattttcaga gcaccttcac tcacataatg tcatttgaac ctcacaatgt tcttgggatg  91020
gagtcagttg ttcagggtcc ccgtgtgtgt gataagcagt gctggctggc tgtcttcaga  91080
actcttggaa atctttacac atgcgagtgc taaccacttt gagcaaggct gccttcttgt  91140
agatgacttg ctgttcttta tgacagggat cagtggcatt tgtttcctag cagtatttag  91200
cacctttttg ccaccttggt gaacagaaaa ttgtattttc ctgtctttca tggctgaaaa  91260
caaaagtaat gggaatttta aatacgtttg cagaaactgc ccctcccctc attgagggtc  91320
actgctcaag agtgcaggag tggactctcc actgatgggt ctccctcccc atcctggttt  91380
ccaccccggg ctggctagct ctgttggttt gaagactgac agccagcctg gctcattctc  91440
attattggct agttagcttt ctttatcaac ctgctcactc acaaatgtgt gccctcagcc  91500
agagagtaag aaagcccaaa tctgttacag cttctaaaaa aatagatttc taatttgtcc  91560
tactcatgtt aggagcatta tctttgaagg taaaacatag tgtatcattg tgtaaactcc  91620
caggcttgat gtagcagaag agatcatttc tggaggcttc agcaatggaa tttagcatta  91680
```

-continued

```
taagagagat tggacaaacc agtccaaagt ggtccgagtt cttaaatcca ggtagggaac  91740
tcactcttct ttcttctctg gacctaattg ggcattgggc tttagtgaga ccacagacca  91800
ggcccgtctc tcctgtaggc ttttaattca atggcaactc tatttcaaag aataaaagcc  91860
tttggagagt tgcggcagtt ctgggggcgg gctcaggaga gtccatagat cagccgtaac  91920
tggaacgtag aatctacgtc tgcctctgaa tggacttccc acctcctctc tcttgctctg  91980
atgcttgcct ctgggcctct ccatgcccaa ggtggtcttt catccttgac aggctggtaa  92040
tgtgctggcc acctccagct cctgcatcga gtctgtaaac cagagctggt tctcatggcc  92100
ttcgtcacga taccaggata cggaggggag cccagggcca tccataccca ccccagggta  92160
acggggctgg cctggcatta gtcattattt agtttccagg ccaaccatcc agatagagat  92220
tccctctttc ctttgagcag tgctctcaag agctccgtgc ctgtccacaa tgacctagag  92280
tgcatcctgc tcattgtcag tgtagcccct cgcccctata ttcatccagg atacttggaa  92340
gtgctaaaat aggaagggat tcggctttca actttgctac catcttccct gaagcaggaa  92400
aatgaacatg gacttaaatg ttctttgaaa aaaccaaagt tttaagattt gctgtgtgat  92460
gaagtgacag ggagggccgg agtcagcagg tgccagactt tctgttctgt ctgccatggg  92520
tttgtccagc tcaggtagct ctaggagcac catcctgccc tagcagagcc caggccttgc  92580
cctcatgaag catcattgaa atagcaggag catgttgatt tcttggttag gttgcattat  92640
aataacaaga gtcagaacat taattcgaaa caacttgcag tatgcatttc ttcacaccag  92700
tacattctta agtgtacttg tttataagga ataacataaa ctaatctgta cctttatata  92760
tatgtgtgtg tacatatata catatataaa ctgtatagtg tacatggtaa tgatttattg  92820
ctatgcccca gatccttaat gtagttctca tcctccgcat gccctcagcc acaagcgggt  92880
gactgactgt tccctgatga tttggcccac ctcctgtgtt tggacctcta gggaggaggg  92940
ttttggtcat actctcctta tcctcgtgca cagaaatgct cagggtcccc atgtgcctgt  93000
tgttcagccc tctctcttgt tccctttctg agcatgtggt ccttccccag gctgtgggac  93060
agctgccttc ccacgaaagt gtaaagcagt attaagatca ttactgcatg tgccctaaaa  93120
acccaagttt tctattccct taggacagaa aattgcatgt gaggtgggat aatcgagttt  93180
cagtgaccca cgtcagttac acattaaagc cagaccccat gataaaattc cacaaaatgg  93240
aaataaaact caaatttctt tagcattgtg taaataaatc tgaatgtgtt taactttgta  93300
ctggtaattt tctgtatatt tggaatattt gggttaaaaa taaaacagac tggactttgt  93360
tacctgacct actgaaatga ctaagctaca gtttgttgat atactttttc cagttttctt  93420
gcttcagaat cagactccag caaccagaga acaagccatt taaagagcca ggactgtaca  93480
tttatagcat gaaatgtatt cggtcatcta tgaggaaaac gtctcacaaa aatgtgagcc  93540
ataaattacc taattttctt gttcttcatt ttcttgctct tagtgctcat acagatcttc  93600
ctcccgtggg tgtgtatacg accagctttc ttgttcttcc tcctagaaag tctaggcacc  93660
caccccacat accttcacag gtttcagttg ctacactctt ccttctggac acagcaacag  93720
ataattactc cttgaattct gtgttctttt gagcaggttt gacccctggc ggcactgaga  93780
agttcagctt tgtaacttcc catctgctcc tcttacattt ctcttgctgt tcttacgggc  93840
cctttcttgt ccctttcatt taaggacctt tggagagttg cagccttcct ctcttgcaaa  93900
gcatttaaga gaggttcctg cccacccgtc tggaaccgtt agccatccta ccctgctagc  93960
ctggggcaat attccatgta atactccagc accttggtct gaagatgaca gggcaaagcc  94020
```

```
cttgttcctg aggcccatct gatgggcgag ttcctacccc aggacattat ctaagatcgt  94080

tgttttattt gaaggaattc tatctaacat ggtattccaa gatttcctgc gccagagtca  94140

ctaggttggt ttttttaggt gcagatttct ggatagcacc ccagacctat tgaattagac  94200

tttctgatgg gcaaacctta ggaacctgca tcttaaagtt gattctttac accttcgctc  94260

caacaaaggg ctaagactca gcctgggcca atttcctcac caaaagatgg gttacgtgtt  94320

gtgtaaaagg gggtgtattt ggggtctcct ggctaggaga ctgtccacac ttacggggcc  94380

ttggctgggt caagcaggaa aaatagttca gaaagacctt caagctagtt ctgatatggc  94440

aaaaacccag tcttctgcca accaaatcaa ccccataggc catccaaggc cccaataaac  94500

agattgtcct gggccttagc tcctatacca gttacaaaga ggctgagctt ctgtcacccc  94560

aagataacac aggctcctgg gatcttacca attaccccaa aattgaaggc aaaaatgagt  94620

aagaagtcag tccatttgtt caactgcacc catttttttt ccatgaaaaa aatacagggg  94680

tgagtagggg gctgtgggaa ccctatactt tccactcagc tttgccgtga ctctcaaact  94740

gctctaaaat taaagcattt taaaatgcag agggatgctg gcttctggag ataagaaggt  94800

aggagtatga taggtggcag tgtccatggc atgtacaaca cgtatagaaa gatggtttgc  94860

taagtctgga aatcatgtag gacctgtagt atgtgactag cacctgctgt gagctggcca  94920

ctttcctata gattgtatca ttttatcctc aacacaatca tggcatcatc ccttgtttca  94980

tagactggga cttgagactc cgagtcggcc atttgcccag agtcccagct ggtgagtgag  95040

tggtacagcc agaagtcaca cgcaggtctc tgagctcgcc tccctccacc actgctgcct  95100

ctccctttat ttgtacttca tctaataggc aaggcagcca ttgacagctc tcaaaggggg  95160

aagtgctggc ctgacctaaa aatagcttac atttatcaag cacttagtcg gctacactct  95220

gctaagcact ttacagagat tacctcttta atcctcacaa cgaccctatg gttataatta  95280

tctccatttt acagatgagg aaacagactg aagagagact gtgaggtgtt gtgagtcaca  95340

cagctagttg gtgacagagc cccaagtggc acctggg                          95377
```

```
<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 4

His His His His His His
1               5


<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Tyr Lys Asp Asp Asp Asp Lys
1               5


<210> SEQ ID NO 6
<211> LENGTH: 4
<212> TYPE: PRT
<213> ORGANISM: Homo sapiens
```

-continued

<400> SEQUENCE: 6

```
Arg Trp Arg Arg
1
```